(12) United States Patent
Wescott et al.

(10) Patent No.: US 11,352,347 B2
(45) Date of Patent: Jun. 7, 2022

(54) DANTROLENE PRODRUGS AND METHODS OF THEIR USE

(71) Applicant: EAGLE RESEARCH LABS LIMITED, Qormi (MT)

(72) Inventors: Charles Wescott, Woodcliff Lake, NJ (US); Adrian Hepner, Ramsey, NJ (US); Alyssa Larson, Needham, MA (US)

(73) Assignee: Eagle Research Labs Limited, Qormi (MT)

( * ) Notice: Subject to any disclaimer, the term of this patent is extended or adjusted under 35 U.S.C. 154(b) by 0 days.

(21) Appl. No.: 16/755,255

(22) PCT Filed: Oct. 19, 2018

(86) PCT No.: PCT/US2018/056713
§ 371 (c)(1),
(2) Date: Apr. 10, 2020

(87) PCT Pub. No.: WO2019/079721
PCT Pub. Date: Apr. 25, 2019

(65) Prior Publication Data
US 2020/0239455 A1 Jul. 30, 2020

Related U.S. Application Data

(60) Provisional application No. 62/575,124, filed on Oct. 20, 2017, provisional application No. 62/674,422, filed on May 21, 2018.

(51) Int. Cl.
*C07D 405/12* (2006.01)
*A61K 9/00* (2006.01)

(52) U.S. Cl.
CPC .......... *C07D 405/12* (2013.01); *A61K 9/0019* (2013.01); *A61K 9/0043* (2013.01); *A61K 9/0053* (2013.01)

(58) Field of Classification Search
CPC .................................................. C07D 405/12
See application file for complete search history.

(56) References Cited

U.S. PATENT DOCUMENTS

| | | | |
|---|---|---|---|
| 3,415,821 A | 12/1968 | Stewert et al. | |
| 4,137,402 A | 1/1979 | White et al. | |
| 8,536,213 B2* | 9/2013 | Riggs-Sauthier | A61K 47/60 514/390 |
| 2009/0306163 A1 | 12/2009 | Lipkin | |
| 2013/0338204 A1 | 12/2013 | Riggs-Sauthier et al. | |
| 2014/0275112 A1 | 9/2014 | Stutzmann et al. | |
| 2014/0336120 A1 | 11/2014 | Mangat et al. | |
| 2016/0024038 A1 | 1/2016 | Stutsmann et al. | |
| 2016/0101085 A1 | 4/2016 | Nanthakumar | |
| 2016/0303085 A1 | 10/2016 | Eros et al. | |

FOREIGN PATENT DOCUMENTS

| | | |
|---|---|---|
| WO | 2009/067175 A2 | 5/2009 |
| WO | 2015/182625 A1 | 12/2015 |
| WO | 2016/077706 A1 | 5/2016 |

OTHER PUBLICATIONS

Acta Poloniae Pharmaceutica—Drug Research, vol. 49, No. 5, pp. 67-69 (1992).
Ellis, K.O. et al., Synthesis and Comparative Skeletal Muscle Relaxant Activity of Some 2,4-Imidazolidinediones and Their Corresponding 5-Hydroxy-2,4-imidazolidinediones, J. Medicinal. Chem., vol. 21, No. 1, pp. 127-130 (Jan. 1978).
Hosoya, T. et al., Dantrolene Analogues Revisited: General Syntehesis and Specific Functions Capable of Discriminating Two Kinds of Ca2+ Release from Sarcoplasmic Reticulum of Mouse Skeletal Muscle, Bioorganic & Medicinal Chem., 11, pp. 663-673 (2003).
Ikemoto, T., et al., Effects of dantrolene and its derivatives on Ca2+ release from the sarcoplasmic reticulum of mouse skeletal muscle fibres, British J. Pharma. 134, pp. 729-736 (2001).
Jornada et al., The Prodrug Approach: A Successful Tool For Improving Drug Solubility, Molecules, Dec. 29, 2015.
Murasawa, S. et al., Small-molecular inhibitors of Ca2+-induced mitochondrial permeability transition (MPT) derived from muscle relaxant dantrolene, Bioorganic & Medicinal Chem., vol. 20, Issue 21, pp. 6384-6393 (Nov. 2012).
Rayburn, L. et al., Conformational Studies of Ortho-and Meta-Isomers and Methyl, Dimethyl, and Chloro Ortho-Substituted Analogues of Dantrolene Using Ab Initio SCF-MO Procedures, Proc. Ark. Acad. Sci., vol. 49, Article 30, pp. 138-142 (1995).
Snyder et al., 1-[5(-Arylfurfurylidene)amino]hydantoins—A New Class of Muscle Relaxants, J. Medicinal Chemistry, (Sep. 1967), 10, 5, pp. 807-810.
Snyder H R et al: "1-[(5-arylfurfurylidene)amino]hydantoins. A new class of muscle relaxants", Journal of Medicinal Chemistry, American Chemical Society, vol. 10, 1967, pp. 807-809, XP002514379.
Wessels F L et al: "Synthesis and skeletal muscle relaxant activity of 3-(aminoacyl)-1-[[[5-(substituted phenyl)-2-D1 furanyl]methylene]amino]-2,4-imidazolidinediones", Journal of Pharmaceutical Sciences, vol. 101, NR. 8, pp. 2675-2680, vol. 70, 1981, pp. 1088-1090, XP002256510.

\* cited by examiner

*Primary Examiner* — Rei Tsang Shiao
(74) *Attorney, Agent, or Firm* — BakerHostetler

(57) ABSTRACT

The disclosure is directed to dantrolene prodrugs, compositions thereof, and methods of their use in the treatment of disease.

24 Claims, 17 Drawing Sheets

DANTROLENE PRODRUGS AND METHODS OF THEIR USE

CROSS REFERENCE TO RELATED APPLICATIONS

This application is a National Stage Application filed under 35 U.S.C. 371 of International Application No. PCT/US2018/056713 filed Oct. 19, 2018, which claims the benefit of U.S Provisional Application No. 62/575,124, filed Oct. 20, 2017, and U.S. Provisional Application No. 62/674,422, filed May 21, 2018, the entireties of which are incorporated by reference herein.

TECHNICAL FIELD

The disclosure is directed to dantrolene prodrugs, compositions thereof, and methods of their use in the treatment of disease.

BACKGROUND

Prodrugs typically are alternative forms of active drugs, reversibly modified or derivatized with a chemical group that renders the prodrug inactive, or confers solubility, stability, or bioavailability, or alters some other property of the active drug. Typically, the chemical group of a prodrug is cleaved from the prodrug by heat, cavitation, pressure, pH change, reduction-oxidation, and/or enzymatic activity acting on the prodrug, thereby releasing the active drug. Cleavage of the chemical group of the prodrug may occur prior to drug delivery to a subject, but generally occurs in vivo by enzymatic processes in the subject.

Dantrolene (1-{[5-(4-nitrophenyl)-2-furyl]methylideneamino}imidazolidine-2,4-dione), has the structure of formula (1):

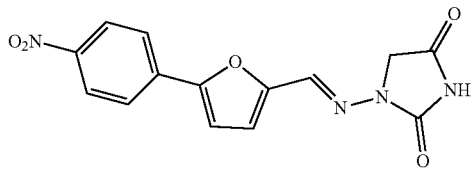 [SMILES: O=C1CN(/N=C/c2ccc(-c3ccc([N+](=O)[O-])cc3)o2)C(=O)N1]

Dantrolene is the rescue agent of choice in the treatment of malignant hyperthermia ("MH") and is widely available in most locations where anesthetics are delivered. First synthesized in 1967, dantrolene was used initially in the treatment of muscle spasms in 1975, and later received FDA approval in 1979 for treating MH. Dantrolene is recognized as a powerful muscle relaxant and as a treatment against nerve spasticity. Since its initial discovery, dantrolene has been explored for the prophylaxis and treatment of other life-threatening conditions such as overdose from recreational drugs such as "ecstasy" (N-methyl-3,4-methylenedioxyphenylisopropylamine), heat stroke, neuroleptic malignant syndrome, and ischemic damage to the peripheral nervous system, and may be of importance in the prevention of sudden infant death syndrome (SIDS).

Dantrolene is very poorly soluble in water. Dantrolene's poor solubility greatly impairs its administration. For example, DANTRIUM™ is dantrolene sodium supplied in 20 mg vials which must be reconstituted with 60 mL of sterile water prior to intravenous administration. The recommended dose of dantrolene for treating MEI is from 1 mg/kg to about 10 mg/kg. As such, a subject weighing 80 kg would require a rapid infusion of up to 2400 mL to treat the MH.

In addition to its poor solubility, dantrolene solutions have a high pH. DANTRIUM™'s pH is about 9.5. RYANODEX®, an improved dantrolene sodium formulation that can be reconstituted to 50 mg/mL, greatly improves the speed with which dantrolene sodium can be administered. But reconstituted RYANODEX® also has a high pH—about 10.3. Because of their high pHs, currently dantrolene formulations cannot be administered subcutaneously or intramuscularly—only intravenously. Indeed, care must be taken to prevent extravasation into the surrounding tissues to avoid tissue necrosis.

While a dantrolene prodrug might be helpful in addressing the drug's solubility and pH challenges, identifying a suitable prodrug moiety is complicated by several factors that are inherent in the dantrolene molecule. For example, it is speculated that dantrolene's poor solubility is attributable to its extended aromatic system, which can engage in hydrophobic pi stacking behavior. Even dantrolene's charged nitro moiety cannot improve the compound's solubility in water.

Dantrolene includes a hydantoin moiety, which is present in other pharmaceutical compounds, such as, for example, phenytoin. But while prodrug strategies to improve the water solubility of other hydantoin-containing compounds has been reported, it is unclear whether similar strategies could be successfully applied to dantrolene, considering its unique chemical structure and physical properties.

There is a need for new formulations of dantrolene that are of a suitable concentration and pH, making them appropriate for intramuscular or subcutaneous use, as well as oral, transmucosal (e.g., intranasal), and intraosseous administration.

SUMMARY

The disclosure is directed to compounds of formula I

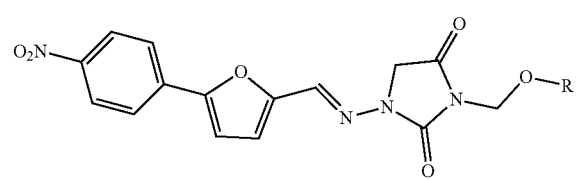

wherein R is —P(O)(OH)$_2$ or —P(O)(OR$_1$)(OR$_2$); R$_1$ is H, —C$_{1-26}$alkyl, aryl, C$_{1-6}$alkC(O)O—C$_{1-26}$alkyl, —C$_1$alkOC(O)C$_{1-26}$alkyl, or C$_1$alkOC(O)OC$_{1-26}$alkyl; and R$_2$ is —C$_{1-26}$alkyl, aryl, C$_{1-6}$alkC(O)O—C$_{1-26}$alkyl, —C$_1$alkOC(O)C$_{1-26}$alkyl, or C$_1$alkOC(O)OC$_{1-26}$alkyl, as well as pharmaceutically acceptable salts thereof. Pharmaceutical compositions comprising the compounds of formula I are also described, as well as methods of their use.

The disclosure is also directed to compounds of formula II

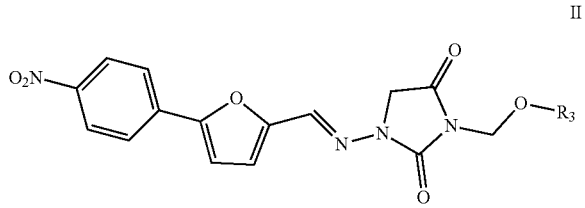

wherein $R_3$ is H, —C(O)—Z—N($R_4$)($R_5$), —C(O)Z—C(O)—OH, or —C(O)—NH—Y—CH$_2$—OC(O)—Z—C(O)—OH; Z is $C_{1-6}$alk; Y is arylene; $C_{1-6}$alkyl; $R_5$ is H or $C_{1-6}$alkyl; or $R_4$ and $R_5$, together with the nitrogen to which they are attached, form a heterocycloalkyl; as well as pharmaceutically acceptable salts thereof. Pharmaceutical compositions comprising the compounds of formula II are also described, as well as methods of their use.

DETAILED DESCRIPTION OF ILLUSTRATIVE EMBODIMENTS

Figure 1:
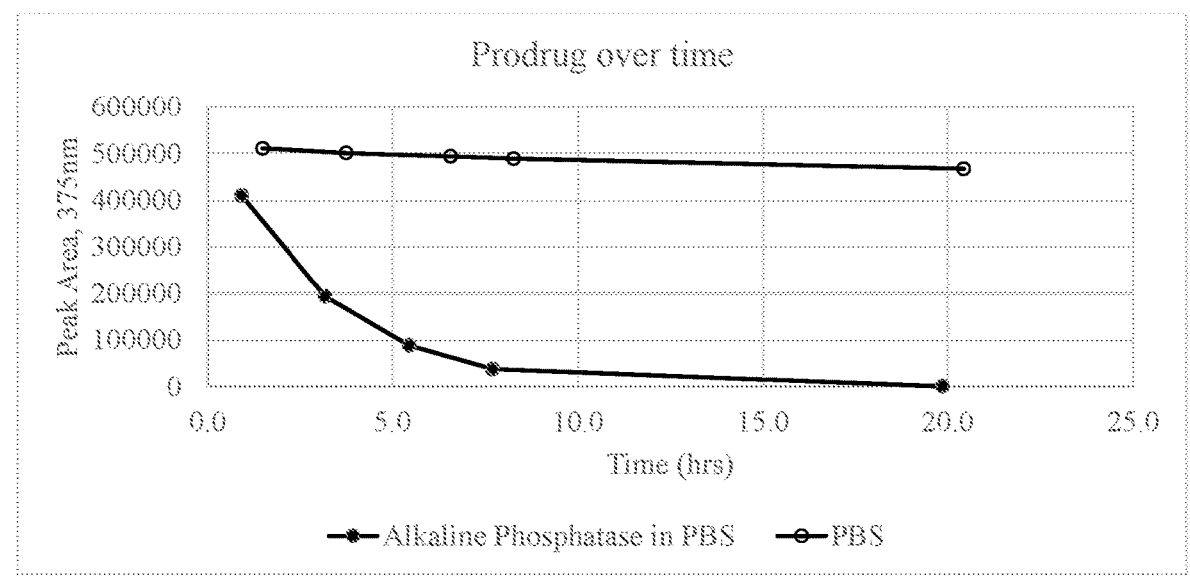
FIG. 1 depicts peak area over time for the conversion of a prodrug of the disclosure to dantrolene by alkaline phosphatase at 25° C.

The present disclosure may be understood more readily by reference to the following detailed description taken in connection with the accompanying figures and examples, which form a part of this disclosure. It is to be understood that this disclosure is not limited to the specific compositions, devices, methods, applications, conditions, or parameters described and/or shown herein, and that the terminology used herein is for the purpose of describing particular embodiments by way of example only and is not intended to be limiting of the claimed disclosure.

As used in the specification including the appended claims, the singular forms "a," "an," and "the" include the plural, and reference to a particular numerical value includes at least that particular value, unless the context clearly dictates otherwise.

When a range of values is expressed, an exemplary embodiment includes from the one particular value and/or to the other particular value. All ranges are inclusive and combinable. Further, reference to values stated in ranges includes each and every value within that range. When values are expressed as approximations, by use of the preposition "about," it will be understood that the particular value forms another embodiment. The term "about" as used herein when referring to a measurable value such as an amount, a temporal duration, and the like, is meant to encompass reasonable variations of the value, such as, for example, ±10% from the specified value. For example, the phrase "about 50%" can include ±10% of 50, or from 45% to 55%, inclusive of 50%.

It is to be appreciated that certain features of the disclosure which are, for clarity, described herein in the context of separate embodiments, may also be provided in combination in a single embodiment. Conversely, various features of the disclosure that are, for brevity, described in the context of a single embodiment, may also be provided separately or in any subcombination.

As used herein, whether by itself or in conjunction with another term or terms, it should be understood that the phrases "method of treating" and "method of treatment" may be used interchangeably with the phrase "for use in the treatment of" a particular disease.

As used herein, whether by itself or in conjunction with another term or terms, "pharmaceutically acceptable" indicates that the designated entity such as, for example, a pharmaceutically acceptable excipient, is generally chemically and/or physically compatible with other ingredients in a composition, and/or is generally physiologically compatible with the recipient thereof.

As used herein, "pharmaceutical composition" refers to a composition prepared by combining any of the formulations including suspensions, or dispersions described herein with one or more pharmaceutically acceptable excipients.

"Pharmaceutically acceptable excipient" refers to a diluent, adjuvant, excipient or carrier with which a compound of the disclosure is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients are enumerated in, for example, Remington's Pharmaceutical Sciences, $17^{th}$ ed., Mack Publishing Co. (1985).

As used herein, whether by themselves or in conjunction with another term or terms, "subject(s)," "individual(s)," and "patient(s)", refer to mammals, including humans. The term human(s) refers to and includes, a human child, adolescent, or adult.

As used herein, whether by themselves or in conjunction with another term or terms, "treats," "treating," "treated," and "treatment," refer to and include ameliorative, palliative, and/or curative uses and results, or any combination thereof. In other embodiments, the methods described herein can be used prophylactically. It should be understood that "prophylaxis" or a prophylactic use or result do not refer to nor require absolute or total prevention (i.e., a 100% preventative or protective use or result). As used herein, prophylaxis or a prophylactic use or result refers to uses and results in which administration of a compound or composition diminishes or reduces the severity of a particular condition, symptom, disorder, or disease described herein; diminishes or reduces the likelihood of experiencing a particular condition, symptom, disorder, or disease described herein; or delays the onset or relapse (reoccurrence) of a particular condition, symptom, disorder, or disease described herein; or any combination of the foregoing.

As used herein, whether used alone or in conjunction with another term or terms, "therapeutic" and "therapeutically effective amount" refer to an amount of a compound or composition that (a) treats a particular condition, symptom, disorder, or disease described herein; (b) attenuates, ameliorates, or eliminates one or more symptoms of a particular condition, disorder, or disease described herein; (c) delays the onset or relapse (reoccurrence) of a particular condition, symptom, disorder, or disease described herein. It should be understood that the terms "therapeutic" and "therapeutically effective" encompass any one of the aforementioned effects (a)-(c), either alone or in combination with any of the others (a)-(c).

The term "$C_1$-$C_6$alk" refers to an aliphatic linker having 1, 2, 3, 4, 5, or 6 carbon atoms and includes, for example, —$CH_2$—, —$CH(CH_3)$—, —$CH(CH_3)$—$CH_2$—, and —$C(CH_3)_2$—. The term "—$C_0$alk-" refers to a bond.

The term "alkyl" refers to a straight- or branched-chain hydrocarbon group having from 1 to 12 carbon atoms ("$C_1$-$C_{12}$"), preferably 1 to 6 carbons atoms ("$C_1$-$C_6$"), in the group. Examples of alkyl groups include methyl (Me, $C_1$alkyl), ethyl (Et, $C_2$alkyl), n-propyl ($C_3$alkyl), isopropyl ($C_3$alkyl), butyl ($C_4$alkyl), isobutyl ($C_4$alkyl), sec-butyl ($C_4$alkyl), tert-butyl ($C_4$alkyl), pentyl ($C_5$alkyl), isopentyl ($C_5$alkyl), tert-pentyl ($C_5$alkyl), hexyl ($C_6$alkyl), isohexyl ($C_6$alkyl), and the like.

The term "heterocycloalkyl" refers to any three to ten membered monocyclic or bicyclic, saturated ring structure containing at least one heteroatom selected from the group consisting of O, N and S. Examples of suitable heterocycloalkyl groups include, but are not limited to, azepanyl, aziridinyl, azetidinyl, pyrrolidinyl, piperazinyl, piperidinyl, morpholinyl, thiomorpholinyl, and the like.

The term "aryl" when used alone or as part of a substituent group refers to a mono- or bicyclic-aromatic hydrocarbon ring structure having 6 or 10 carbon atoms in the ring. Preferred aryl moieties include phenyl and naphthyl.

The term "arylene" refers to a mono- or bicyclic-aromatic hydrocarbon ring structure having 6 or 10 carbon atoms in the ring. Preferred arylene moieties include phenylene and naphthylene. Compounds of the disclosure may be chiral and as a result, can exist as a single enantiomer or mixture of enantiomers. All enantiomers and mixtures thereof are contemplated by this disclosure.

Isotopic variants of the compound of formula I and II are also within the scope of the disclosure. As used herein, the term "isotopic variant" refers to a compound that contains proportions of isotopes at one or more of the atoms that constitute such compound, in greater than natural abundance. For example, an "isotopic variant" of a compound can be radiolabeled, that is, contain one or more radioactive isotopes, or can be labeled with non-radioactive isotopes such as for example, deuterium ($^2$H or D), carbon-11 ($^{11}$C), carbon-13 ($^{13}$C), nitrogen-15 ($^{15}$N), fluoride-18 ($^{18}$F), or the like. It will be understood that, in a compound where such isotopic substitution is made, the following atoms, where present, may vary, so that for example, any hydrogen may be $^2$H/D, any carbon may be $^{11}$C or $^{13}$C, any nitrogen may be $^{15}$N, or any fluoride (if present) may be $^{18}$F, and that the presence and placement of such atoms may be determined within the skill of the art.

Compounds of formula I and II convert to dantrolene in vivo. In some aspects, the compounds of formula I and II convert to dantrolene in vivo with a half-life of about 1 second or less to about 1 minute to 90 minutes. In some aspects, the compounds of formula I and II convert to dantrolene in vivo with a half-life of less than 1 second. In other aspects, the compounds of formula I and II convert to dantrolene in vivo with a half-life of seconds, that is, with a half-life of less than one minute, for example, with a half-life of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or about 59 seconds. In other aspects, the compounds of formula I and II convert to dantrolene in vivo with a half-life of about 1 to about 5 minutes, for example, about 1, 2, 3, 4, or about 5 minutes. In other aspects, the compounds of formula I and II convert to dantrolene in vivo with a half-life of about 1 to about 10 minutes. In other aspects, the compounds of formula I and II convert to dantrolene in vivo with a half-life of about 5 to about 10 minutes. In some aspects, the compounds of formula I and II convert to dantrolene in vivo with a half-life of about 1 minute to 60 minutes. In some aspects, the compounds of formula I and II convert to dantrolene in vivo with a half-life of about 1 minute to 45 minutes. In some aspects, the compounds of formula I and II convert to dantrolene in vivo with a half-life of about 1 minute to 30 minutes. In some aspects, the compounds of formula I and II convert to dantrolene in vivo with a half-life of about 1 minute to 20 minutes. In some aspects, the compounds of formula I and II convert to dantrolene in vivo with a half-life of about 1, 2, 3, 4, 5, 10, 15, 20, 25, 30, 35, 40, 45, 50, 55, 60, 65, 70, 75, 80, 85, or about 90 minutes.

The disclosure is directed to dantrolene prodrugs of formula I:

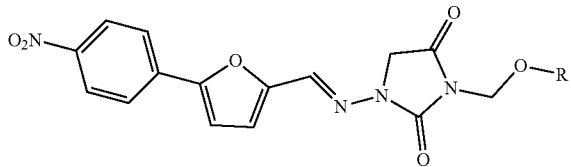

wherein R is

—P(O)(OH)$_2$ or —P(O)(OR$_1$)(OR$_2$);

R$_1$ is H, —C$_{1-26}$alkyl, aryl, C$_{1-6}$alkC(O)O—C$_{1-26}$alkyl, —C$_1$alkOC(O)C$_{1-26}$alkyl, or C$_1$alkOC(O)OC$_{1-26}$alkyl; and R$_2$ is —C$_{1-26}$alkyl, aryl, C$_{1-6}$alkC(O)O—C$_{1-26}$alkyl, —C$_1$alkOC(O)C$_{1-26}$alkyl, or C$_1$alkOC(O)OC$_{1-26}$alkyl;

or a pharmaceutically acceptable salt thereof.

In some aspects, the dantrolene prodrugs of the disclosure are those wherein R is —P(O)(OH)$_2$ and are of formula I-A:

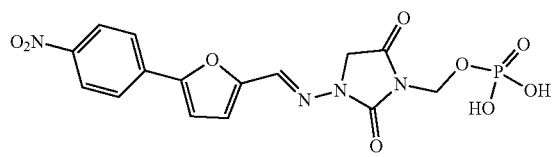

Pharmaceutically acceptable salts of compounds of formula I-A are also within the scope of the disclosure. Preferred salts include, for example, sodium salts of compounds of formula I-A. Lithium, magnesium, calcium, and potassium salts of the compounds of formula I-A are also within the scope of the disclosure. Alternative salt forms include ammonium, choline, and tromethamine salts. A preferred salt of the compound of formula I-A is the monosodium salt. Another preferred salt of the compound of formula I-A is the disodium salt. Another preferred salt of the compound of formula I-A is the monotromethamine salt. Another preferred salt of the compound of formula I-A is the ditromethanine salt. Also within the scope of the disclosure are pharmaceutically acceptable organic salts of compounds of formula I-A.

In some aspects, the dantrolene prodrugs of the disclosure are those wherein R is —P(O)(OR$_1$)(OR$_2$) and are of formula I-B:

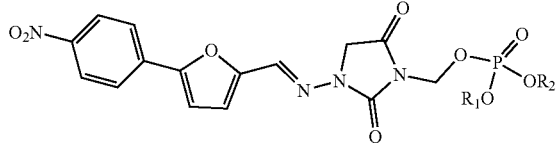

In some aspects, R$_1$ is H. In these aspects, R$_2$ is —C$_{1-26}$alkyl, aryl, C$_{1-6}$alkC(O)O—C$_{1-26}$alkyl, —C$_1$alkOC(O)C$_{1-26}$alkyl, or C$_1$alkOC(O)OC$_{1-26}$alkyl. Pharmaceutically acceptable salts of such compounds of formula I—B are also within the scope of the disclosure. Preferred salts include, for example, sodium salts of compounds of formula I-B. Other salts include the lithium, magnesium, calcium, and potassium salts of the compounds of formula I-B. Alternative salt forms include ammonium, choline, and tromethamine salts. Also within the scope of the disclosure are pharmaceutically acceptable organic salts of compounds of formula I-B.

In some aspects of compounds of formula I-B, R$_1$ is H and R$_2$ is —C$_{1-26}$alkyl. For example, in some aspects, R$_1$ is H and R$_2$ is —C$_{1-6}$alkyl. In other aspects, R$_1$ is H and R$_2$ is —C$_{1-12}$alkyl. In other aspects, R$_1$ is H and R$_2$ is —C$_{13-26}$alkyl. In other aspects, R$_1$ is H and R$_2$ is —C$_{18-26}$alkyl. In other aspects, R$_1$ is H and R$_2$ is —C$_{20-26}$alkyl. In some aspects, R$_1$ is H and R$_2$ is —C$_1$alkyl. In some aspects, R$_1$ is H and R$_2$ is —C$_2$alkyl. In some aspects, R$_1$ is H and R$_2$ is —C$_3$alkyl. In some aspects, R$_1$ is H and R$_2$ is —C$_4$alkyl. In some aspects, R$_1$ is H and R$_2$ is —C$_5$alkyl. In some aspects, R$_1$ is H and R$_2$ is —C$_6$alkyl. In some aspects, R$_1$ is H and R$_2$ is —C$_7$alkyl. In some aspects, R$_1$ is H and R$_2$ is —C$_8$alkyl. In some aspects, R$_1$ is H and R$_2$ is —C$_9$alkyl. In some aspects, R$_1$ is H and R$_2$ is —C$_{10}$alkyl. In some aspects, R$_1$ is H and R$_2$ is —C$_{11}$alkyl. In some aspects, R$_1$ is H and R$_2$ is —C$_{12}$alkyl. In some aspects, R$_1$ is H and R$_2$ is —C$_{13}$alkyl. In some aspects, R$_1$ is H and R$_2$ is —C$_{14}$alkyl. In some aspects, R$_1$ is H and R$_2$ is —C$_{15}$alkyl. In some aspects, R$_1$ is H and R$_2$ is —C$_{16}$alkyl. In some aspects, R$_1$ is H and R$_2$ is —C$_{17}$alkyl. In some aspects, R$_1$ is H and R$_2$ is —C$_{18}$alkyl. In some aspects, R$_1$ is H and R$_2$ is —C$_{19}$alkyl. In some aspects, R$_1$ is H and R$_2$ is —C$_{20}$alkyl. In some aspects, R$_1$ is H and R$_2$ is —C$_{21}$alkyl. In some aspects, R$_1$ is H and R$_2$ is —C$_{22}$alkyl. In some aspects, R$_1$ is H and R$_2$ is —C$_{23}$alkyl. In some aspects, R$_1$ is H and R$_2$ is —C$_{24}$alkyl. In some aspects, R$_1$ is H and R$_2$ is —C$_{25}$alkyl. In some aspects, R$_1$ is H and R$_2$ is C$_{26}$alkyl.

In some aspects of compounds of formula I-B, R$_1$ is H and R$_2$ is aryl. For example, in some aspects, In some aspects of compounds of formula I-B, R$_1$ is H and R$_2$ is phenyl.

In some aspects of compounds of formula I-B, R$_1$ is H and R$_2$ is C$_{1-6}$alkC(O)O—C$_{1-26}$alkyl. For example, in some aspects, R$_1$ is H and R$_2$ is C$_1$alkC(O)O—C$_{1-26}$alkyl. In other aspects, R$_1$ is H and R$_2$ is C$_2$alkC(O)O—C$_{1-26}$alkyl. In other aspects, R$_1$ is H and R$_2$ is C$_3$alkC(O)O—C$_{1-26}$alkyl. In other aspects, R$_1$ is H and R$_2$ is C$_4$alkC(O)O—C$_{1-26}$alkyl. In other aspects, R$_1$ is H and R$_2$ is C$_5$alkC(O)O—C$_{1-26}$alkyl. In other aspects, R$_1$ is H and R$_2$ is C$_6$alkC(O)O—C$_{1-26}$alkyl. In other aspects, R$_1$ is H and R$_2$ is C$_{1-6}$alkC(O)O—C$_{1-26}$alkyl. In other aspects, R$_1$ is H and R$_2$ is C$_{1-6}$alkC(O)O—C$_{1-12}$alkyl. In other aspects, R$_1$ is H and R$_2$ is C$_{1-6}$alkC(O)O—C$_{13-26}$alkyl.

In other aspects, $R_1$ is H and $R_2$ is $C_{1-6}$alkC(O)O—$C_{18-26}$alkyl. In other aspects, $R_1$ is H and $R_2$ is $C_{1-6}$alkC(O)O—$C_{20-26}$alkyl.

In some aspects of compounds of formula I-B, $R_1$ is H and $R_2$ is —$C_1$alkOC(O)$C_{1-26}$alkyl. For example, in some aspects, $R_1$ is H and $R_2$ is —$C_1$alkOC(O)$C_{1-6}$alkyl. In other aspects, $R_1$ is H and $R_2$ is —$C_1$alkOC(O)$C_{1-12}$alkyl. $R_1$ is H and $R_2$ is —$C_1$alkOC(O)$C_{13-16}$alkyl. $R_1$ is H and $R_2$ is —$C_1$alkOC(O)$C_{18-26}$alkyl. $R_1$ is H and $R_2$ is —$C_1$alkOC(O)$C_{20-26}$alkyl.

In some aspects of compounds of formula I-B, $R_1$ is H and $R_2$ is —$C_1$alkOC(O)O$C_{1-26}$alkyl. For example, in some aspects, $R_1$ is H and $R_2$ is —$C_1$alkOC(O)O$C_{1-6}$alkyl. In other aspects, $R_1$ is H and $R_2$ is —$C_1$alkOC(O)O$C_{1-12}$alkyl. In some aspects, $R_1$ is H and $R_2$ is —$C_1$alkOC(O)O$C_{13-16}$alkyl. In some aspects, $R_1$ is H and $R_2$ is —$C_1$alkOC(O)O$C_{18-26}$alkyl. In some aspects, $R_1$ is H and $R_2$ is —$C_1$alkOC(O)O$C_{20-26}$alkyl.

In other aspects of compounds of formula I-B, $R_1$ is —$C_{1-26}$alkyl, aryl, $C_{1-6}$alkC(O)O—$C_{1-26}$alkyl, —$C_1$alkOC(O)$C_{1-26}$alkyl, or $C_1$alkOC(O)O$C_{1-26}$alkyl and $R_2$ is —$C_{1-26}$alkyl, aryl, $C_{1-6}$alkC(O)O—$C_{1-26}$alkyl, —$C_1$alkOC(O)$C_{1-26}$alkyl, or $C_1$alkOC(O)O$C_{1-26}$alkyl.

In some aspects of compounds of formula I-B, $R_1$ is —$C_{1-26}$alkyl and $R_2$ is —$C_{1-26}$alkyl, aryl, $C_{1-6}$alkC(O)O—$C_{1-26}$alkyl, —$C_1$alkOC(O)$C_{1-26}$alkyl, or $C_1$alkOC(O)O$C_{1-26}$alkyl. For example, in these aspects, $R_1$ can be —$C_{1-6}$alkyl. In other aspects, $R_1$ is —$C_{1-12}$alkyl. In other aspects, $R_1$ is —$C_{13-26}$alkyl. In other aspects, $R_1$ is —$C_{18-26}$alkyl. In other aspects, $R_1$ is —$C_{20-26}$alkyl. In some aspects, $R_1$ is —$C_1$alkyl. In some aspects, $R_1$ is —$C_2$alkyl. In some aspects, $R_1$ is —$C_3$alkyl. In some aspects, $R_1$ is —$C_4$alkyl. In some aspects, $R_1$ is —$C_5$alkyl. In some aspects, $R_1$ is —$C_6$alkyl. In some aspects, $R_1$ is —$C_7$alkyl. In some aspects, $R_1$ is —$C_8$alkyl. In some aspects, $R_1$ is —$C_9$alkyl. In some aspects, $R_1$ is —$C_{10}$alkyl. In some aspects, $R_1$ is —$C_{11}$alkyl. In some aspects, $R_1$ is —$C_{12}$alkyl. In some aspects, $R_1$ is —$C_{13}$alkyl. In some aspects, $R_1$ is —$C_{14}$alkyl. In some aspects, $R_1$ is —$C_{15}$alkyl. In some aspects, $R_1$ is —$C_{16}$alkyl. In some aspects, $R_1$ is —$C_{17}$alkyl. In some aspects, $R_1$ —$C_{18}$alkyl. In some aspects, $R_1$ is —$C_{19}$alkyl. In some aspects, $R_1$ is —$C_{20}$alkyl. In some aspects, $R_1$ is —$C_{21}$alkyl. In some aspects, $R_1$ is —$C_{22}$alkyl. In some aspects, $R_1$ is —$C_{23}$alkyl. In some aspects, $R_1$ is —$C_{24}$alkyl. In some aspects, $R_1$ is —$C_{25}$alkyl. In some aspects, $R_1$ is —$C_{26}$alkyl.

In some aspects of compounds of formula I-B, $R_1$ is aryl and $R_2$ is —$C_{1-26}$alkyl, aryl, $C_{1-6}$alkC(O)O—$C_{1-26}$alkyl, —$C_1$alkOC(O)$C_{1-26}$alkyl, or $C_1$alkOC(O)O$C_{1-26}$alkyl. For example, in some aspects, $R_1$ is phenyl and $R_2$ is —$C_{1-26}$alkyl, aryl, $C_{1-6}$alkC(O)O—$C_{1-26}$alkyl, —$C_1$alkOC(O)$C_{1-26}$alkyl, or $C_1$alkOC(O)O$C_{1-26}$alkyl.

In some aspects of compounds of formula I-B, $R_1$ is $C_{1-6}$alkC(O)O—$C_{1-26}$alkyl and $R_2$ is —$C_{1-26}$alkyl, aryl, $C_{1-6}$alkC(O)O—$C_{1-26}$alkyl, —$C_1$alkOC(O)$C_{1-26}$alkyl, or $C_1$alkOC(O)O$C_{1-26}$alkyl. For example, in some aspects, $R_1$ is $C_1$alkC(O)O—$C_{1-26}$alkyl. In other aspects, $R_1$ is $C_2$alkC(O)O—$C_{1-26}$alkyl. In other aspects, $R_1$ is $C_3$alkC(O)O—$C_{1-26}$alkyl. In other aspects, $R_1$ is $C_4$alkC(O)O—$C_{1-26}$alkyl. In other aspects, $R_1$ is $C_5$alkC(O)O—$C_{1-26}$alkyl. In other aspects, $R_1$ is $C_6$alkC(O)O—$C_{1-26}$alkyl. In other aspects, $R_1$ is $C_{1-6}$alkC(O)O—$C_{1-6}$alkyl. In other aspects, $R_1$ is $C_{1-6}$alkC(O)O—$C_{1-12}$alkyl. In other aspects, $R_1$ is $C_{1-6}$alkC(O)O—$C_{13-26}$alkyl. In other aspects, $R_1$ is $C_{1-6}$alkC(O)O—$C_{18-26}$alkyl. In other aspects, $R_1$ is $C_{1-6}$alkC(O)O—$C_{20-26}$alkyl.

In some aspects of compounds of formula I-B, $R_1$ is —$C_1$alkOC(O)$C_{1-26}$alkyl and $R_2$ is —$C_{1-26}$alkyl, aryl, $C_{1-6}$alkC(O)O—$C_{1-26}$alkyl, —$C_1$alkOC(O)$C_{1-26}$alkyl, or $C_1$alkOC(O)O$C_{1-26}$alkyl. For example, in some aspects, $R_1$ is $C_1$alkOC(O)$C_{1-6}$alkyl. In other aspects, $R_1$ is —$C_1$alkOC(O)$C_{1-12}$alkyl. In other aspects, $R_1$ is —$C_1$alkOC(O)$C_{13-16}$alkyl. In other aspects, $R_1$ is —$C_1$alkOC(O)$C_{18-26}$alkyl. In other aspects, $R_1$ is —$C_1$alkOC(O)$C_{20-26}$alkyl.

In some aspects of compounds of formula I-B, $R_1$ is —$C_1$alkOC(O)O$C_{1-26}$alkyl and $R_2$ is —$C_{1-26}$alkyl, aryl, $C_{1-6}$alkC(O)O—$C_{1-26}$alkyl, —$C_1$alkOC(O)$C_{1-26}$alkyl, or $C_1$alkOC(O)O$C_{1-26}$alkyl. For example, in some aspects, $R_1$ is $C_1$alkOC(O)O$C_{1-6}$alkyl. In other aspects, $R_1$ is —$C_1$alkOC(O)O$C_{1-12}$alkyl. In other aspects, $R_1$ is —$C_1$alkOC(O)O$C_{13-16}$alkyl. In other aspects, $R_1$ is —$C_1$alkOC(O)O$C_{18-26}$alkyl. In other aspects, $R_1$ is —$C_1$alkOC(O)O$C_{20-26}$alkyl.

In some aspects, $R_1$ is —$C_{1-26}$alkyl and $R_2$ is —$C_{1-26}$alkyl. For example, in some aspects $R_1$ and $R_2$ are each independently —$C_{1-6}$alkyl, —$C_{1-12}$alkyl, —$C_{13-26}$alkyl, —$C_{18-26}$alkyl, —$C_{20-26}$alkyl, —$C_1$alkyl, —$C_2$alkyl, —$C_3$alkyl, —$C_4$alkyl, —$C_5$alkyl, —$C_6$alkyl, —$C_7$alkyl, —$C_8$alkyl, —$C_9$alkyl, —$C_{10}$alkyl, —$C_{11}$alkyl, —$C_{12}$alkyl, —$C_{13}$alkyl, —$C_{14}$alkyl, —$C_{15}$alkyl, —$C_{16}$alkyl, —$C_{17}$alkyl, —$C_{18}$alkyl, —$C_{19}$alkyl, —$C_{20}$alkyl, —$C_{21}$alkyl, —$C_{22}$alkyl, —$C_{23}$alkyl, —$C_{24}$alkyl, —$C_{25}$alkyl, or —$C_{26}$alkyl.

In some aspects, $R_1$ is aryl (e.g., phenyl) and $R_2$ is aryl (e.g., phenyl).

In some aspects, $R_1$ is $C_{1-6}$alkC(O)O—$C_{1-26}$alkyl and $R_2$ is $C_{1-6}$alkC(O)O—$C_{1-26}$alkyl. For example, in some aspects, $R_1$ and $R_2$ are each independently $C_1$alkC(O)O—$C_{1-26}$alkyl, $C_2$alkC(O)O—$C_{1-26}$alkyl, $C_3$alkC(O)O—$C_{1-26}$alkyl, $C_4$alkC(O)O—$C_{1-26}$alkyl, $C_5$alkC(O)O—$C_{1-26}$alkyl, $C_6$alkC(O)O—$C_{1-26}$alkyl, $C_{1-6}$alkC(O)O—$C_{1-6}$alkyl, $C_{1-6}$alkC(O)O—$C_{1-12}$alkyl, $C_{1-6}$alkC(O)O—$C_{13-26}$alkyl, $C_{1-6}$alkC(O)O—$C_{18-26}$alkyl, or $C_{1-6}$alkC(O)O—$C_{20-26}$alkyl.

In some aspects, $R_1$ is —$C_1$alkOC(O)$C_{1-26}$alkyl and $R_2$ is —$C_1$alkOC(O)$C_{1-26}$alkyl. For example, in some aspects, $R_1$ and $R_2$ are each independently $C_1$alkOC(O)$C_{1-6}$alkyl, —$C_1$alkOC(O)$C_{1-12}$alkyl, —$C_1$alkOC(O)$C_{13-16}$alkyl, —$C_1$alkOC(O)$C_{18-26}$alkyl, or —$C_1$alkOC(O)$C_{20-26}$alkyl.

In some aspects, $R_1$ is —$C_1$alkOC(O)O$C_{1-26}$alkyl and $R_2$ is —$C_1$alkOC(O)O$C_{1-26}$alkyl. For example, in some aspects, $R_1$ and $R_2$ are each independently $C_1$alkOC(O)O$C_{1-6}$alkyl, —$C_1$alkOC(O)O$C_{1-12}$alkyl, —$C_1$alkOC(O)O$C_{13-16}$alkyl, —$C_1$alkOC(O)O$C_{18-26}$alkyl, or —$C_1$alkOC(O)O$C_{20-26}$alkyl.

Compounds of formula I, which includes compounds of formula I-A and I-B, can be present as pharmaceutically acceptable salts, where applicable. These salts include sodium salts. Potassium, lithium, calcium, and magnesium salts are also envisioned. Alternative salt forms include ammonium, choline, and tromethamine salts.

Also within the scope of the disclosure are to dantrolene prodrugs of formula II

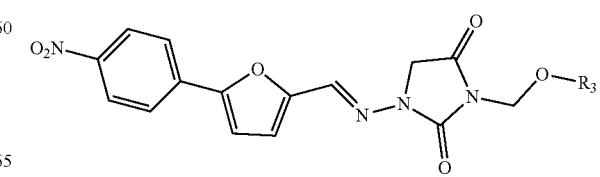

II wherein

R$_3$ is H, —C(O)—Z—N(R$_4$)(R$_5$), —C(O)Z—C(O)—OH, or —C(O)—Y—CH$_2$—OC(O)—Z—C(O)—OH;

Z is C$_{1-6}$alk;

Y is aryl;

R$_4$ is H or C$_{1-6}$alkyl;

R$_5$ is H or C$_{1-6}$alkyl;

or R$_4$ and R$_5$, together with the nitrogen to which they are attached, form a heterocycloalkyl;

or a pharmaceutically acceptable salt thereof.

In preferred aspects, R$_3$ is H and the compound of formula II is a compound of formula II-A

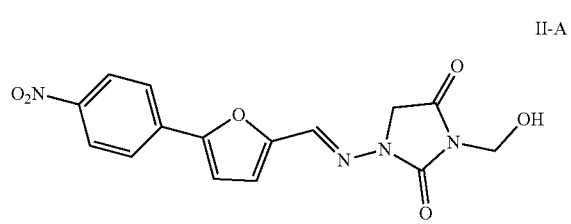 [SMILES: O=C1CN(/N=C/c2ccc(-c3ccc([N+](=O)[O-])cc3)o2)C(=O)N1CO]

II-A or a pharmaceutically acceptable salt thereof.

In other aspects of formula II, R$_3$ is C(O)—Z—N(R$_4$)(R$_5$) and the compound of formula II is a compound of formula II-B

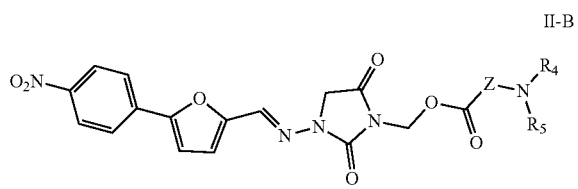

II-B wherein

Z is C$_{1-6}$alk;

R$_4$ is H or C$_{1-6}$alkyl;

R$_5$ is H or C$_{1-6}$alkyl;

or R$_4$ and R$_5$, together with the nitrogen to which they are attached, form a heterocycloalkyl;

or a pharmaceutically acceptable salt thereof.

In these aspects of formula II-B, Z can be C$_1$alk, C$_2$alk, C$_3$alk, C$_4$alk, C$_5$alk, or C$_6$alk. In some aspects, Z is C$_{1-2}$alk. In some aspects, Z is C$_1$alk.

In these aspects of formula II-B, R$_4$ is H. In other aspects, R$_4$ is C$_{1-6}$alkyl, for example, C$_1$alkyl, C$_2$alkyl, C$_3$alkyl, C$_4$alkyl, C$_5$alkyl, or C$_6$alkyl. In preferred aspects, R$_4$ is methyl, ethyl, or isopropyl.

In these aspects of formula II-B, R$_5$ is H. In other aspects, R$_5$ is C$_{1-6}$alkyl, for example, C$_1$alkyl, C$_2$alkyl, C$_3$alkyl, C$_4$alkyl, C$_5$alkyl, or C$_6$alkyl. In preferred aspects, R$_5$ is methyl, ethyl, or isopropyl.

In some of these aspects of formula II-B, R$_4$ is H and R$_5$ is H. In other aspects, R$_4$ is H and R$_5$ is C$_{1-6}$alkyl, for example, C$_1$alkyl, C$_2$alkyl, C$_3$alkyl, C$_4$alkyl, C$_5$alkyl, or C$_6$alkyl. In yet other aspects, R$_4$ and R$_5$ are each independently C$_{1-6}$alkyl, for example, C$_1$alkyl, C$_2$alkyl, C$_3$alkyl, C$_4$alkyl, C$_5$alkyl, or C$_6$alkyl.

In some of these aspects of formula II-B, R$_4$ and R$_5$, together with the nitrogen to which they are attached, form a heterocycloalkyl. Preferred heterocycloalkyl moieties include, for example, morpholinyl, piperazinyl, piperidinyl, pyrrolidinyl, azetidinyl, and aziridinyl.

Preferred compounds for formula II-B include, for example,

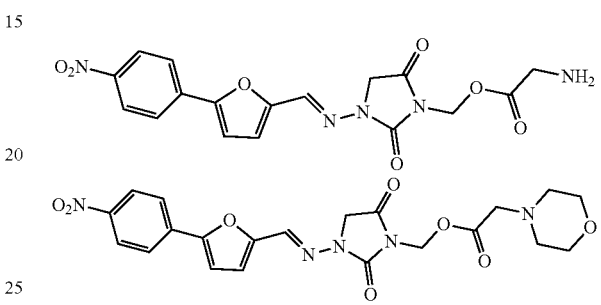

and pharmaceutically acceptable salts thereof.

In other aspects of formula II, R$_3$ is C(O)—Z—C(O)—OH and the compound of formula II is a compound of formula II-C

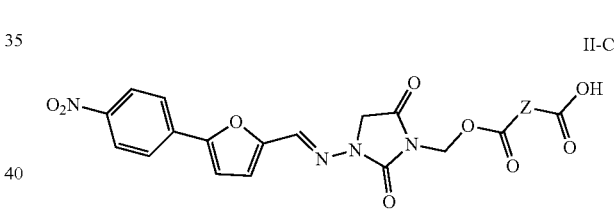

II-C wherein

Z is C$_{1-6}$alk;

or a pharmaceutically acceptable salt thereof.

In these aspects of formula II-C, Z can be C$_1$alk, C$_2$alk, C$_3$alk, C$_4$alk, C$_5$alk, or C$_6$alk. In some aspects, Z is C$_{1-2}$alk. In some aspects, Z is C$_1$alk. In some aspects, Z is C$_2$alk.

A preferred compound of formula II-C is

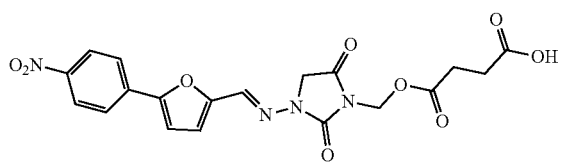 [SMILES: O=C(O)CCC(=O)OCN1C(=O)CN(/N=C/c2ccc(-c3ccc([N+](=O)[O-])cc3)o2)C1=O]

and pharmaceutically acceptable salts thereof.

In other aspects of formula II, R$_3$ is —C(O)—NH—Y—CH$_2$—OC(O)—Z—C(O)—OH and the compound of formula II is a compound of formula II-D

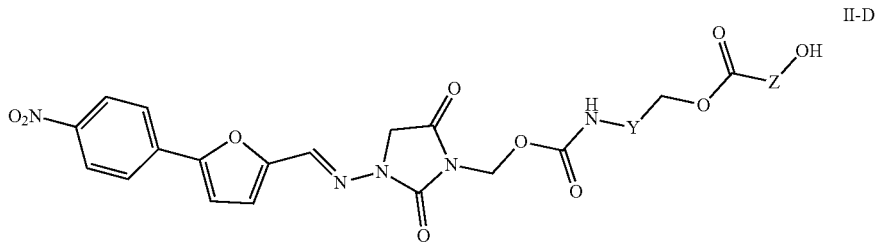

II-D wherein
Y is arylene; and
Z is $C_{1-6}$alk;
or a pharmaceutically acceptable salt thereof.

In these aspects of formula II-D, Y can be phenylene or naphthylene, preferably phenylene.

In these aspects of formula II-D, Z can be $C_1$alk, $C_2$alk, $C_3$alk, $C_4$alk, $C_5$alk, or $C_6$alk. In some aspects, Z is $C_{1-2}$alk. In some aspects, Z is $C_1$alk. In some aspects, Z is $C_2$alk.

A preferred compound of formula II-D is

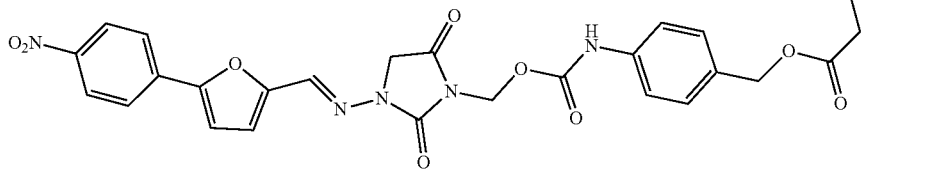

and pharmaceutically acceptable salts thereof.

In other aspects, $R_3$ is —C(O)—O—Y—CH$_2$—OC(O)—Z—C(O)—OH and the compound of formula II is a compound of formula II-E

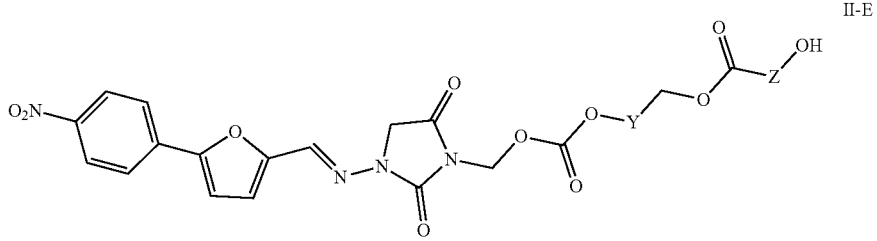

II-E wherein
Y is arylene; and
Z is $C_{1-6}$alk;
or a pharmaceutically acceptable salt thereof.

In these aspects of formula II-E, Y can be phenylene or naphthylene, preferably phenylene.

In these aspects of formula II-E, Z can be $C_1$alk, $C_2$alk, $C_3$alk, $C_4$alk, $C_5$alk, or $C_6$alk. In some aspects, Z is $C_{1-2}$alk. In some aspects, Z is $C_1$alk. In some aspects, Z is $C_2$alk.

Compounds of formula II, which includes compounds of formula II-A, II-B, II-C, II-D, and II-E can be present as pharmaceutically acceptable salts, where applicable. These salts include sodium salts. Potassium, lithium, calcium, and magnesium salts are also envisioned. Alternative salt forms include ammonium, choline, and tromethamine salts. Also within the scope of the disclosure are pharmaceutically acceptable organic salts of compounds of formula II.

Compounds of formula I and II, which includes compounds of formula I-A, I-B, II-A, II-B, II-C, II-D, and II-E and pharmaceutically acceptable salts thereof, can prepared as pharmaceutical compositions by combining the compound with a pharmaceutically acceptable excipient. In some embodiments, the one or more additional pharmaceutically acceptable excipients are selected from the group consisting of preservatives, antioxidants, or mixtures thereof. In yet further embodiments of the disclosure, the additional pharmaceutically acceptable excipient is a preservative such as, but not limited to, phenol, cresol, p-hydroxybenzoic ester, chlorobutanol, or mixtures thereof. In yet further embodiments of the disclosure, the additional pharmaceutically acceptable excipient is an antioxidant such as, but not limited to, ascorbic acid, sodium pyrosulfite, palmitic acid, butylated hydroxyanisole, butylated hydroxytoluene, tocopherols, or mixtures thereof.

Pharmaceutical compositions of the disclosure may be provided as suspensions. In other embodiments, the pharmaceutical compositions of the disclosure may be provided as solutions.

Pharmaceutical compositions of the disclosure can have the compound of the disclosure present at a concentration of about 1 mg/ml to about 400 mg/mL, for example, 1 mg/mL to about 200 mg/mL, 1 mg/mL to about 300 mg/mL, preferably 5 mg/mL to about 125 mg/mL, preferably at physiologic pH. In particular embodiments of the disclosure, a compound of the disclosure is present at a concentration equal to or greater than about 5 mg/mL. In further embodiments, a compound of the disclosure is present at a concentration of about 10 to 25 mg/mL. In still further embodiments, a compound of the disclosure is present at a concentration of about 1 mg/mL, 5 mg/mL, 10 mg/mL, 15 mg/mL, 20 mg/mL, 25 mg/mL, 30 mg/mL, 35 mg/mL, 40 mg/mL, 45 mg/mL, or 50 mg/mL. In still further embodiments, a compound of the disclosure is present at a concentration of about 125 mg/mL, 150 mg/mL, 175 mg/mL, 200 mg/mL, 225 mg/mL, 250 mg/mL, 275 mg/mL, 300 mg/mL, 325 mg/mL, 350 mg/mL, 375 mg/mL, or about 400 mg/mL.

In certain embodiments, a compound of the disclosure is present at a concentration equal to or greater than about 55 mg/mL. In further embodiments, a compound of the disclosure is present at a concentration of about 55 to 125 mg/mL. In particular embodiments, a compound of the disclosure is present at a concentration of about 75 mg/mL, 80 mg/mL, 85 mg/mL, 90 mg/mL, 95 mg/mL, 100 mg/mL, 105 mg/mL, 110 mg/mL, 115 mg/mL, 120 mg/mL or 125 mg/mL. In other embodiments, a compound of the disclosure is present at a concentration of about 75 mg/mL to 95 mg/mL, 80 mg/mL to 100 mg/mL, 90 mg/mL to 110 mg/ml, 95 mg/mL to 105 mg/mL, 95 mg/mL to 115 mg/mL, 100 mg/mL to 110 mg/mL, 110 mg/mL to 125 mg/mL, including all ranges and subranges there between.

In certain embodiments, pharmaceutical compositions of the disclosure may further comprise a stabilizer or two or more stabilizers. In still further embodiments of the disclosure, the stabilizer is selected from the group consisting of surfactants, polymers, cross-linked polymers, buffering agents, electrolytes, and non-electrolytes. In yet further embodiments of the disclosure, the composition comprises a combination of two or more stabilizers selected from the group consisting of surfactants, polymers, cross-linked polymers, buffering agents, electrolytes, and non-electrolytes. In yet further embodiments of the disclosure, the stabilizer is a surfactant such as, but not limited to, polyethylene oxide (PEO), a PEO derivative, polysorbate 80, polysorbate 20, poloxamer 188, polyethoxylated vegetable oils, lecithin, human serum albumin, and mixtures thereof. In particular embodiments of the disclosure, the stabilizer is a polymer, such as, but not limited to, a polyvinylpyrrolidone (such as, but not limited to povidone K12, povidone K17, and mixtures thereof), polyethylene glycol 3350, and mixtures thereof. In other embodiments of the disclosure, the stabilizer is an electrolyte such as, but not limited to, sodium chloride, calcium chloride, and mixtures thereof. In still other embodiments of the disclosure, the stabilizer is a non-electrolyte, such as, but not limited to, dextrose, glycerol, mannitol, or mixtures thereof. In other embodiments of the disclosure, the stabilizer is a cross-linked polymer such as, but not limited to, carboxymethylcellulose sodium (CMC). In some embodiments of the disclosure, the stabilizer is CMC 7LF, CMC 7MF, CMC 7HF, or mixtures thereof.

In further embodiments of the disclosure, combinations of non-electrolyte stabilizers and electrolyte stabilizers may be used. In some embodiments, the combination of stabilizers may comprise two or more non-electrolyte stabilizers. In other embodiments, the combination of stabilizers may comprise two or more electrolyte stabilizers. In further embodiments, the combination of stabilizers may comprise one or more non-electrolyte stabilizers and one or more electrolyte stabilizers. In yet further embodiments, the combination of stabilizers may comprise two or more of mannitol, dextrose, and sodium chloride.

In certain embodiments of the disclosure, combinations of surfactant stabilizers and polymer stabilizers may be used. In some embodiments, the combination of stabilizers may comprise two or more surfactant stabilizers. In other embodiments, the combination of stabilizers may comprise two or more polymer stabilizers. In further embodiments, the combination of stabilizers may comprise one or more surfactant stabilizers and one or more polymer stabilizers. In yet further embodiments, the combination of stabilizers may comprise two or more of polysorbate 80, polysorbate 20, and poloxamer 188. In still further embodiments, the combination of stabilizers may comprise one or more of polysorbate 80, polysorbate 20, and poloxamer 188 and one or more of povidone K12, povidone K17, and polyethylene glycol 3350.

In certain embodiments of the disclosure, the composition comprises about 0.2 mg/mL to about 75 mg/mL of the one or more stabilizers, and all ranges and subranges therebetween. In particular embodiments of the disclosure, the composition comprises about 0.2 to 0.7 mg/mL, 0.5 to 1 mg/mL, 1 to 5 mg/mL, 2 to 8 mg/mL, 5 to 6 mg/mL, 5 to 10 mg/mL, 8 to 12 mg/mL, 10 to 15 mg/mL, 15 to 20 mg/mL, 20 to 30 mg/mL, 30 to 40 mg/mL, 40 to 50 mg/mL, 45 to 55 mg/mL, 50 to 60 mg/mL, or 60 to 75 mg/mL of one or more stabilizers, and all ranges and subranges there between. In further embodiments of the disclosure, the composition comprises about 0.2 mg/mL, 0.5 mg/mL, 1 mg/mL, 2 mg/mL, 3 mg/mL, 4 mg/mL, 5 mg/mL, 5.5 mg/mL, 6 mg/mL, 7 mg/mL, 8 mg/mL, 9 mg/mL, 10 mg/mL, 12 mg/mL, 15 mg/mL, 17 mg/mL, 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, or 75 mg/mL of one or more stabilizers.

In particular embodiments of the disclosure, the composition further comprises one or more buffering agents, such as, but not limited to, $NaH_2PO_4.H_2O$, $NaH_2PO_4.2H_2O$, anhydrous $NaH_2PO_4$, sodium citrate, citric acid, Tris, sodium hydroxide, HCl, or mixtures thereof. In certain embodiments of the disclosure, the composition comprises about 1 mM to 20 mM of one or more buffering agents, and all ranges and subranges therebetween. In particular embodiments of the disclosure, the composition comprises about 1 to 2 mM, 1 to 3 mM, 1 to 5 mM, 2 to 8 mM, 5 to 6 mM, 5 to 10 mM, 8 to 12 mM, 10 to 15 mM, or 15 to 20 mM of one or more buffering agents, and all ranges and subranges therebetween. In further embodiments of the disclosure, the composition comprises about 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, or 20 mM of one or more buffering agents.

In certain embodiments of the disclosure, a pharmaceutical composition has a pH of from about 3-10, for example, 3, 4, 5, 6, 7, 8, 9, or 10. In further embodiments of the disclosure, the composition has a pH of from about 5-9. In further embodiments of the disclosure, the composition has a pH of from about 6 to 9. In further embodiments of the disclosure, the composition has a pH of from about 6 to 7. In further embodiments of the disclosure, the composition has a pH of from about 6 to 8.5. In further embodiments of the disclosure, the composition has a pH of from about 7 to 8.5. In further embodiments of the disclosure, the composition has a pH of from over 7 to 8.5. In certain embodiments of the disclosure, the composition has a pH of about 6.0 to 8.0. In particular embodiments of the disclosure, the composition has a pH of about 6.0 to 7.0, 6.5 to 7.0, 6.5 to 7.5, 6.7 to 7.2, 7.0 to 7.2, 7.0 to 7.5, 7.0 to 8.0 or 7.0 to 8.5

In certain embodiments of the disclosure, a pharmaceutical composition has an osmolarity from about 280 mOsm/L to about 310 mOsm/L, for example, about 280, 285, 290, 300, 305, or about 310 mOsm/L. In further embodiments of the disclosure, the composition has an osmolarity from about 290 mOsm/L to about 300 mOsm/L. In yet further embodiments of the disclosure, the composition has an osmolarity of about 290 mOsm/L. In some embodiments, the osmolarity may be selected through the use of appropriate amounts of one or more stabilizers that act as tonicifiers in a composition, such as, but not limited to, the non-electrolyte stabilizers and electrolyte stabilizers described herein. In some embodiments, the osmolarity may be selected through the use of appropriate amounts of one or more buffering agents that act as tonicifiers in a composition, such as, but not limited to, the buffering agents described herein.

Pharmaceutical compositions of the disclosure can be administered intravenously. Alternatively, pharmaceutical compositions of the disclosure can be administered intramuscularly. In other embodiments, pharmaceutical compositions of the disclosure are administered subcutaneously. Pharmaceutical compositions of the disclosure can also be administered orally. In other embodiments, pharmaceutical compositions of the disclosure are administered transmuscosally, for example via intranasal administration. In other embodiments, pharmaceutical compositions of the disclosure are administered intraosseously.

Compounds and pharmaceutical compositions of the disclosure can be used to treat disorders responsive to dantrolene. For example, subjects in need of treatment can be administered a therapeutically effective amount of a compound of the disclosure, or a salt thereof. In other aspects, subjects in need of treatment can be administered a therapeutically effective amount of a pharmaceutical composition of the disclosure, or a salt thereof. In other aspects, subjects in need of treatment can be exposed to a therapeutically effective amount of a compound of the disclosure, for example, a compound of formula I-A, I-B, II-A, II-B, II-C, II-D, II-E or a pharmaceutically acceptable salt thereof. For example, subjects in need of treatment can be exposed to a therapeutically effective amount of a compound of the disclosure, for example, a compound of formula II-A, or a pharmaceutically acceptable salt thereof.

Disorders responsive to dantrolene include, for example, malignant hyperthermia, chronic spasticity, exertional heat stroke, cardiac arrhythmias, tachycardia, atrial fibrillation, cardiac arrest, myocardial infarction, heart failure, myocardial injury, cardiomyopathy, central core disease, amyotrophic lateral sclerosis, rhabdomyolysis, Duchenne muscular dystrophy, ataxia, detrusor overactivity, overactive bladder, seizure, epilepsy, neuroleptic malignant syndrome, human stress disorder, Alzheimer's disease, Huntington's disease, multiple sclerosis, amyotrophic lateral sclerosis, Parkinson's disease, ischemia-reperfusion injury, neuronal reperfusion injury, hypoxia, cerebral aneurysm, subarachnoid hemorrhage, stroke, hyperthermia associated with drug abuse, or hyperthermia associated with drug overdose.

In preferred aspects, the compounds and/or pharmaceutical compositions of the disclosure are used to treat malignant hyperthermia in a subject.

In other aspects, the compounds and/or pharmaceutical compositions of the disclosure are used to treat chronic spasticity in a subject.

In other aspects, the compounds and/or pharmaceutical compositions of the disclosure are used to treat exertional heat stroke in a subject.

In other aspects, the compounds and/or pharmaceutical compositions of the disclosure are used to treat cardiac arrhythmias in a subject.

In other aspects, the compounds and/or pharmaceutical compositions of the disclosure are used to treat tachycardis in a subject.

In other aspects, the compounds and/or pharmaceutical compositions of the disclosure are used to treat atrial fibrillation in a subject.

In other aspects, the compounds and/or pharmaceutical compositions of the disclosure are used to treat cardia arrest in a subject.

In other aspects, the compounds and/or pharmaceutical compositions of the disclosure are used to treat myocardial infarction in a subject.

In other aspects, the compounds and/or pharmaceutical compositions of the disclosure are used to treat heart failure in a subject.

In other aspects, the compounds and/or pharmaceutical compositions of the disclosure are used to treat myocardial injury in a subject.

In other aspects, the compounds and/or pharmaceutical compositions of the disclosure are used to treat cardiomyopathy in a subject.

In other aspects, the compounds and/or pharmaceutical compositions of the disclosure are used to treat central core disease in a subject.

In other aspects, the compounds and/or pharmaceutical compositions of the disclosure are used to treat amyotrophic lateral sclerosis in a subject.

In other aspects, the compounds and/or pharmaceutical compositions of the disclosure are used to treat rhabdomyolysis in a subject.

In other aspects, the compounds and/or pharmaceutical compositions of the disclosure are used to treat Duchenne muscular dystrophy in a subject.

In other aspects, the compounds and/or pharmaceutical compositions of the disclosure are used to treat ataxia in a subject.

In other aspects, the compounds and/or pharmaceutical compositions of the disclosure are used to treat detrusor overactivity in a subject.

In other aspects, the compounds and/or pharmaceutical compositions of the disclosure are used to treat overactive bladder in a subject.

In other aspects, the compounds and/or pharmaceutical compositions of the disclosure are used to treat seizure in a subject.

In other aspects, the compounds and/or pharmaceutical compositions of the disclosure are used to treat epilepsy in a subject.

In other aspects, the compounds and/or pharmaceutical compositions of the disclosure are used to treat neuroleptic malignant syndrome in a subject.

In other aspects, the compounds and/or pharmaceutical compositions of the disclosure are used to treat human stress disorder in a subject.

In other aspects, the compounds and/or pharmaceutical compositions of the disclosure are used to treat Alzheimer's disease in a subject.

In other aspects, the compounds and/or pharmaceutical compositions of the disclosure are used to treat Huntington's disease in a subject.

In other aspects, the compounds and/or pharmaceutical compositions of the disclosure are used to treat multiple sclerosis in a subject.

In other aspects, the compounds and/or pharmaceutical compositions of the disclosure are used to treat Parkinson's disease in a subject.

In other aspects, the compounds and/or pharmaceutical compositions of the disclosure are used to treat ischemia-reperfusion injury in a subject.

In other aspects, the compounds and/or pharmaceutical compositions of the disclosure are used to treat neuronal reperfusion injury in a subject.

In other aspects, the compounds and/or pharmaceutical compositions of the disclosure are used to treat hypoxia in a subject.

In other aspects, the compounds and/or pharmaceutical compositions of the disclosure are used to treat cerebral aneurysm in a subject.

In other aspects, the compounds and/or pharmaceutical compositions of the disclosure are used to treat subarachnoid hemorrhage in a subject.

In other aspects, the compounds and/or pharmaceutical compositions of the disclosure are used to treat stroke in a subject.

In other aspects, the compounds and/or pharmaceutical compositions of the disclosure are used to treat hyperthermia associated with drug abuse (e.g., ecstasy (3,4-Methylenedioxymethamphetamine) abuse) in a subject.

In other aspects, the compounds and/or pharmaceutical compositions of the disclosure are used to treat hyperthermia associated with drug overdose (e.g., ecstasy (3,4-Methylenedioxymethamphetamine) overdose) in a subject.

In other aspects, the compounds and/or pharmaceutical compositions of the disclosure are used to treat acetylcholine accumulation in a subject. In other aspects, the compounds and/or pharmaceutical compositions of the disclosure are used to treat neurotoxic nerve agent exposure, for example, nerve gas exposure, (e.g., organophosphorus gases such as sarin, soman, and VX) in a subject. See, e.g., U.S. Provisional Application No. 62/554,049, filed Sep. 5, 2017. As used herein, "neurotoxic nerve agent" or "nerve agent" refers to compounds that affect the transmission of nerve impulses in the nervous system. Nerve agents are organophosphorus compounds, that is, they are of the formula $(R)_3P(O)$, wherein each R group can be the same or different. "G"-type nerve agents include O-pinacolyl methylphosphonofluoridate (soman, GD), ethyl N,N-dimethylphosphoramidocyanidate (tabun, GA), propan-2-yl methylphosphonofluoridate (sarin, GB), cyclohexyl methylphosphonofluoridate (cyclosarin, GF), and 2-(Dimethylamino)ethyl (GV). "V"-type nerve agents include O-cyclopentyl S-(2-diethylaminoethyl) methylphosphonothiolate (EA-3148), (S)-(ethyl {[2-(diethylamino)ethyl]sulfonyls} (ethyl)phosphonates) such as (S)-(ethyl {[2-(diethylamino) ethyl]sulfanyl}(ethyl)phosphinate) (VE), O,O-Diethyl S-[2-(diethylamino)ethyl] phosphorothioate (VG), S-[2-(Diethylamino)ethyl] O-ethyl methylphosphonothioate (VM), N,N-diethyl-2-(methyl-(2-methylpropoxy)phosphoryl)sulfanylethanamine (VR), and Ethyl ({2-[bis(propan-2-yl)amino]ethyl}sulfanyl)(methyl)phosphinate (VX). The methods described herein can be used to treat a subject exposed to one nerve agent. The methods described herein can also be used to treat a subject exposed to two or more nerve agents.

As used herein, the phrases, "resulting from exposure to a nerve agent" and "due to nerve agent exposure" refer to effects that are a direct consequence of nerve agent exposure, as well as to effects that are a secondary consequence of nerve agent exposure.

In some aspects, the disclosure is directed to methods of treating a subject exposed to a nerve agent with a pharmaceutical composition comprising an amount of a compound of Formula I as described herein, or a pharmaceutically acceptable salt thereof. For example, in some aspects, the described methods prevent neurologic damage secondary to nerve agent exposure. In other aspects, the described methods provide neuroprotective effects following nerve agent exposure. In other aspects, the described methods ameliorate brain tissue damage secondary to nerve agent exposure. In other aspects, the described methods ameliorate brain tissue damage secondary to status epilepticus secondary to nerve agent exposure. In other aspects, the described methods prevent neuronal necrosis due to nerve agent exposure. In other aspects, the described methods ameliorate neuronal necrosis due to nerve agent exposure. In other aspects, the described methods treat intracellular calcium overload due to nerve agent exposure. In other aspects, the described methods ameliorate intracellular calcium overload due to nerve agent exposure. In other aspects, the described methods prevent intracellular calcium overload due to nerve agent exposure.

The subjects described herein can be exposed to a nerve agent via inhalation. In other aspects, subjects are exposed to a nerve agent via transdermal transmission of the agent. In still other aspects, subjects are exposed to a nerve agent via consumption of a liquid or food that has been contaminated with a nerve agent. In other aspects, subjects are exposed to a nerve agent via subcutaneous, intravenous, or intramuscular administration of the agent to the subject.

In some aspects, the methods are directed to methods of protecting a subject from neural necrosis, after the subject has been exposed to a nerve agent. In these embodiments, a pharmaceutical composition comprising an amount of a compound of formula I or a pharmaceutically acceptable salt thereof, is administered to the subject after the subject has been exposed to a nerve agent. As used herein, "protection" from neural necrosis encompasses lessening the severity of the effects of the nerve agent or ameliorating the effect of the nerve agent or decreasing the neural damage resulting from the nerve agent exposure. In some aspects, "protection" from neural necrosis encompasses the prevention of neural necrosis in a subject that has been exposed to a nerve agent. That is, subjects that are "protected" from neural necrosis by administration of the compounds and compositions described herein perform better on neurobehavioral tests, as compared to nerve agent-exposed subjects that were not administered the described compounds or compositions.

In some embodiments, the entirety of the central nervous system of the subject is protected from neural necrosis. In some embodiments, the fronto-parietal cortex, the hippocampus, and/or the thalamus is protected from neural necrosis. In other aspects, the fronto-parietal cortex will be protected from neural necrosis. In other aspects, the hippocampus is protected from neural necrosis. In other embodiments, the thalamus is protected from neural necrosis.

The presence and extent of neural necrosis can be determined using methods known in the art, including neurobehavioral tests, radiological tests, and pathology evaluation.

The disclosure is also directed to methods of protecting a subject from a decrease in central nervous system function resulting from exposure to a nerve agent. These methods comprise administering to the subject a pharmaceutical composition comprising an amount of a compound of formula I or a pharmaceutically acceptable salt thereof, after the subject has been exposed to a nerve agent.

The disclosure is also directed to methods of protecting a subject from a central nervous system dysfunction resulting from exposure to a nerve agent. These methods comprise administering to the subject a pharmaceutical composition comprising an amount of a compound of formula I as described herein or a pharmaceutically acceptable salt thereof, after the subject has been exposed to a nerve agent.

The disclosure is also directed to methods of treating behavior changes in a subject resulting from exposure to a nerve agent. These methods comprise administering to the subject a pharmaceutical composition comprising an amount of a compound of formula I or a pharmaceutically acceptable salt thereof, after the subject has been exposed to a nerve agent.

As used herein, "protection" from a decrease in central nervous system function encompasses lessening the severity of the central nervous system effects of the nerve agent or ameliorating the central nervous system effects of the nerve agent or decreasing the central nervous system effects of the nerve agent. That is, subjects that are "protected" from a decrease in central nervous system function by administration of the described compounds of formula I-containing compositions, perform better on neurobehavioral tests, as compared to nerve agent-exposed subjects that were not administered the described compositions.

The disclosure is also directed to methods of treating nerve agent-induced seizures in a subject that has been exposed to a nerve agent. In some aspects, the seizures treated are status epilepticus (SE). These methods comprising administering to the subject a pharmaceutical composition comprising an amount of a compound of formula I or II or a pharmaceutically acceptable salt thereof. As used herein, treatment of nerve agent-induced seizures results in a reduction in the severity or duration of the seizures. In other aspects, the treatment results in a reduction in both the severity and duration of the seizure.

The amount of the compound of formula I or II, or a pharmaceutically acceptable salt thereof, that is effective to treat the subject according to any of the described methods should be determined by a practitioner skilled in the art. The therapeutically effective amount can be the amount needed to treat the subject in a single dose. Alternatively, the therapeutically effective amount can be the cumulative amount of dantrolene needed to treat the subject over a chronic course of treatment.

In those embodiments wherein the subject is human, the effective amount of the compound of formula I or II is an amount of compound equivalent to 1 mg/kg to 100 mg/kg of dantrolene, administered in one or more doses. In other aspects, the effective amount of the compound of formula I or II is equivalent to 1 mg/kg to about 90 mg/kg of dantrolene. In other aspects, the effective amount of the compound of formula I or II is equivalent to 1 mg/kg to about 80 mg/kg of dantrolene. In other aspects, the effective amount of the compound of formula I or II is equivalent to 1 mg/kg to about 70 mg/kg of dantrolene. In other aspects, the effective amount of the compound of formula I or II is equivalent to 1 mg/kg to about 60 mg/kg of dantrolene. In other aspects, the effective amount of the compound of formula I or II is equivalent to 1 mg/kg to about 50 mg/kg of dantrolene. In other aspects, the effective amount of the compound of formula I or II is 1 mg/kg to about 40 mg/kg of dantrolene. In other aspects, the effective amount of the compound of formula I or II is equivalent to 1 mg/kg to about 30 mg/kg of dantrolene. In other aspects, the effective amount of the compound of formula I or II is equivalent to 1 mg/kg to about 20 mg/kg of dantrolene. In other aspects, the effective amount of the compound of formula I or II is equivalent to about 5 mg/kg to about 30 mg/kg of dantrolene. In other aspects, the effective amount of the compound of formula I or II is equivalent to about 10 mg/kg to about 30 mg/kg of dantrolene. In other aspects, the effective amount of the compound of formula I or II is equivalent to equivalent to about 15 mg/kg to about 30 mg/kg of dantrolene. In other aspects, the effective amount of the compound of formula I or II is equivalent to about 20 mg/kg to about 30 mg/kg of dantrolene. In other aspects, the effective amount of the compound of formula I or II is equivalent to about 5 mg/kg to about 20 mg/kg of dantrolene. In other aspects, the effective amount of the compound of formula I or II is equivalent to about 5 mg/kg to about 15 mg/kg of dantrolene. In other aspects, the effective amount of the compound of formula I or II is equivalent to about 5 mg/kg to about 10 mg/kg of dantrolene. In other aspects, the effective amount of the compound of formula I or II is equivalent to about 10 mg/kg to about 20 mg/kg of dantrolene. In other aspects, the effective amount of the compound of formula I or II is equivalent to about 2 mg/kg to about 10 mg/kg, preferably from about 2 mg/kg to about 6 mg/kg, of dantrolene. In other aspects, the effective amount of the compound of formula I or II is equivalent to about 15 mg/kg to about 20 mg/kg of dantrolene. In other aspects, the effective amount of the compound of formula I or II is equivalent to 10 mg/kg to 100 mg/kg of dantrolene. In other aspects, the effective amount of the compound of formula I or II is equivalent to 20 mg/kg to 100 mg/kg of dantrolene. In other aspects, the effective amount of the compound of formula I or II is equivalent to 30 mg/kg to 100 mg/kg of dantrolene. In other aspects, the effective amount of the compound of formula I or II is equivalent to 40 mg/kg to 100 mg/kg of dantrolene. In other aspects, the effective amount of the compound of formula I or II is equivalent to 50 mg/kg to 100 mg/kg of dantrolene. In other aspects, the effective amount of the compound of formula I or II is equivalent to equivalent to 50 mg/kg to 75 mg/kg of dantrolene. In other aspects, the effective amount of the compound of formula I or II is equivalent to 25 mg/kg to 75 mg/kg of dantrolene. In some aspects, the effective amount of the compound of formula I or II is about equivalent to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or about 34 mg/kg of dantrolene. In some aspects, the effective amount of the compound of formula I or II for treating a human subject is equivalent to about 35, 40, 45, 50, 55, 60, 65, 70, 75, 80, 85, 90, 95, or about 100 mg/kg of dantrolene. In other aspects, the effective amount of the compound of formula I or II is equivalent to about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100 mg/kg of dantrolene.

In some aspects of the disclosure, the timing of the administration of the pharmaceutical composition comprising the compound of formula I or II or a pharmaceutically acceptable salt thereof, to the subject, after exposure to a nerve agent, can affect the amount of neural necrosis protection conferred to the subject.

In some aspects of the disclosure, the timing of the administration of the pharmaceutical composition comprising the compound of formula I or II or a pharmaceutically acceptable salt thereof, to the subject, after exposure to a nerve agent, can affect the amount of decrease in central nervous system function conferred to the subject.

In some aspects of the disclosure, the timing of the administration of the pharmaceutical composition comprising the compound of formula I or II or a pharmaceutically acceptable salt thereof, to the subject, after exposure to a nerve agent can affect the treatment of nerve agent-induced seizures in the subject.

Regarding the timing of the administration of the pharmaceutical composition comprising the compound of formula I or II, or a pharmaceutically acceptable salt thereof, in some aspects, the pharmaceutical composition comprising the compound of formula I or II, or a pharmaceutically acceptable salt thereof, at least one dose is administered to the subject 24 hours or less after the subject has been exposed to the nerve agent. In some aspects, the pharmaceutical composition comprising the compound of formula I, or a pharmaceutically acceptable salt thereof, at least one dose is administered to the subject 20 hours or less after the subject has been exposed to the nerve agent. In some aspects, the pharmaceutical composition comprising the compound of formula or II I, or a pharmaceutically acceptable salt thereof, at least one dose is administered to the subject 16 hours or less after the subject has been exposed to the nerve agent. In some aspects, the pharmaceutical composition comprising the compound of formula I or II, or a pharmaceutically acceptable salt thereof, at least one dose is administered to the subject 12 hours or less after the subject has been exposed to the nerve agent. In some aspects, the pharmaceutical composition comprising the compound of formula I or II, or a pharmaceutically acceptable salt thereof, at least one dose is administered to the subject 8 hours or less after the subject has been exposed to the nerve agent. In some aspects, the pharmaceutical composition comprising the compound of formula I or II, or a pharmaceutically acceptable salt thereof, at least one dose is administered to the subject 4 hours or less after the subject has been exposed to the nerve agent. In some aspects, the pharmaceutical composition comprising the compound of formula I or II, or a pharmaceutically acceptable salt thereof, at least one dose is administered to the subject 2 hours or less after the subject has been exposed to the nerve agent. In some aspects, the pharmaceutical composition comprising the compound of formula I or II, or a pharmaceutically acceptable salt thereof, at least one dose is administered to the subject 1 hour or less after the subject has been exposed to the nerve agent. In some aspects, the pharmaceutical composition comprising the compound of formula or III, or a pharmaceutically acceptable salt thereof, i at least one dose s administered to the subject within about 1, 2, 3, 4, 5, 6, 7, 8, 9, 10, 11, 12, 13, 14, 15, 16, 17, 18, 19, 20, 21, 22, 23, or within about 24 hours after the subject has been exposed to a nerve agent.

While in some aspects, the pharmaceutical composition comprising the compound of formula I or II, or a pharmaceutically acceptable salt thereof, can deliver the effective amount of the compound of formula I or II to the nerve agent-exposed subject in one dose. In other aspects, two or more doses of the pharmaceutical composition may be needed to deliver the effective amount of the compound of formula I or II to the nerve agent-exposed subject. For example, 2, 3, 4, 5, 6, 7, 8, 9, or 10 doses of the pharmaceutical composition may be needed to deliver the effective amount of the compound of formula I or II to the nerve agent-exposed subject. These additional dosages can be administered substantially concurrently with the first dose. In other aspects, the additional dosages are separated in time from the first dose. In those aspects wherein 3 or more doses are administered, each dose can be separated in time from the administration of any other dose. Dose separations can be 1 or more hours apart, for example, 1, 2, 3, 4, 5, 6, 7, 8, 9, 10, 11, 12, 13, 14, 15, 16, 17, 18, 19, 20, 21, 22, 23, or 24 hours apart. In other aspects, dose separations can be 1 or more days apart.

According to the disclosure, the administration of the compound of formula I or II to the nerve agent-exposed subject is an adjunct therapy for nerve agent exposure. Subjects exposed to a nerve agent can also be administered one or more nerve agent antidotes. One class of antidotes for nerve agent-exposure is acetylcholinesterase reactivators, for example asoxime chloride (HI-6). Another class of antidotes for nerve agent-exposure is reverse antagonist of acetylcholine receptors, for example, atropine methyl nitrate. Subjects exposed to nerve agents may also be administered anti-seizure medication. Exemplary anti-seizure medications include aldehydes (e.g., paraldehyde), aromatic allylic alcohols (e.g., stiripentol), benzodiazepines (e.g., clobazam, clonazepam, clorazepate, diazepam, midazolam, lorazepam, nitrazepam, temazepam, nimetazepam), barbiturates (e.g., phenobarbital, methylphenobarbital, barbexaclone), bromides (e.g., potassium bromide), carbamates (e.g., felbamate), carboxamides (e.g., carbamazepine, oxcarbazepine, eslicarbazepine acetate), fatty acids (e.g., valproic acid, sodium valproate, divalproex sodium, vigabatrin, progabide, tiagabine), topiramate, GABA analogs (e.g., gabapentin, pregabalin), hydantoins (e.g., ethotoin, phenytoin, mephenytoin, fosphenytoin), oxazolidinediones (e.g., paramethadione, trimethadione, ethadione), propionates (e.g., beclamide), pyrimidinediones (e.g., primidone), pyrrolidines (e.g., brivaracetam, levitiracetam, seletracetam), succinimides (e.g., ethosuximide, phensuximide, mesuximide), sulfonamides (e.g., acetazolamide, sultiame, methazolamide, zonisamide), triazines (e.g., lamotrigine), ureas (e.g., pheneturide, phenacemide), valproylamides (e.g., valpromide, valnoctamide), perampanel, and combinations thereof. In some aspects, the anti-seizure medication is a benzodiazepine, for example, midazolam. In other aspects, the anti-seizure medication is a barbiturate. In still other aspects, the anti-seizure medication is a hydantoin. In some aspects, the anti-seizure medication is paraldehyde. In other aspects, the anti-seizure medication is potassium bromide. In some aspects, the anti-seizure medication is a fatty acid. In other aspects, the anti-seizure medication is topiramate.

In those aspects wherein the nerve agent-exposed subject is administered an antidote, the compound of formula I or II is administered after the antidote has been administered. For example, the compound of formula I or II can be administered after the administration of the acetylcholinesterase reactivator and/or after the administration of the reverse antagonist of acetylcholine receptors.

In those aspects wherein the nerve agent-exposed subject is administered an anti-seizure medication, the compound of formula I or II can be administered concurrently with the administration of the anti-seizure medication. The compound of formula I or II can be administered substantially currently with the administration of the anti-seizure medication, as well, for example, within about 5 minutes of the anti-seizure medication administration. In other embodiments, the compound of formula I or II is administered before the anti-seizure medication is administered. In other embodiments, the compound of formula I or II is administered after the anti-seizure medication is administered.

The pharmaceutical composition comprising the compound of formula I or II, or a pharmaceutically acceptable salt thereof can be administered intravenously. In other aspects, the pharmaceutical composition comprising the compound of formula I or II, or a pharmaceutically acceptable salt thereof can be administered transdermally. In other aspects, the pharmaceutical composition comprising the compound of formula I or II, or a pharmaceutically acceptable salt thereof can be administered intramuscularly. In other aspects, the pharmaceutical composition comprising the compound of formula I or II, or a pharmaceutically acceptable salt thereof can be administered intraosseously. In other aspects, the pharmaceutical composition comprising the compound of formula I or II, or a pharmaceutically acceptable salt thereof can be administered subcutaneously.

Preferred pharmaceutical compositions for use in the described methods include the compound of formula I or II, or a pharmaceutically acceptable salt thereof, and one or more pharmaceutically acceptable excipients. Preferred pharmaceutical compositions comprise the compound of formula I or II or a pharmaceutically acceptable salt thereof, mannitol, a polysorbate (e.g., polysorbate 80), a povidone (e.g. povidone K12), an optional pH adjustor (e.g. NaOH or HCl), and water.

According to the disclosure, administration of a compound and/or pharmaceutical composition as disclosed herein will produce a substantially equivalent AUC in the subject, as compared to the administration of a reference-listed dantrolene product such as RYANODEX®. In other aspects, administration of a compound and/or pharmaceutical composition as disclosed herein will produce a substantially equivalent AUC in the subject, as compared a comparative composition. For example, in some aspects, upon administration to a subject, the 90% confidence intervals (CI) of the relative mean $AUC_{(0-t)}$ and $AUC_{(0-\infty)}$ of dantrolene of a disclosed pharmaceutical composition will be within 80% to 125% (e.g., 80%, 85%, 90%, 95%, 100%, 105%, 110%, 115%, 120%, or 125%) of the relative mean $AUC_{(0-t)}$ and $AUC_{(0-\infty)}$, respectively, of dantrolene upon administration of a reference listed dantrolene product, for example, RYANODEX®. In some aspects, upon administration to a subject, the 90% confidence intervals (CI) of the relative mean $AUC_{(0-t)}$ and $AUC_{(0-\infty)}$ of dantrolene of a disclosed pharmaceutical composition will be within 80% to 125% (e.g., 80%, 85%, 90%, 95%, 100%, 105%, 110%, 115%, 120%, or 125%) of the relative mean $AUC_{(0-t)}$ and $AUC_{(0-\infty)}$, respectively, of dantrolene upon administration of a comparative product.

The following examples are provided to illustrate some of the concepts described within this disclosure. While each example is considered to provide specific individual embodiments of disclosure, none of the Examples should be considered to limit the more general embodiments described herein. In the following examples, efforts have been made to ensure accuracy with respect to numbers used (e.g. amounts, temperature, etc.) but some experimental error and deviation should be accounted for.

EXAMPLES

Example 1

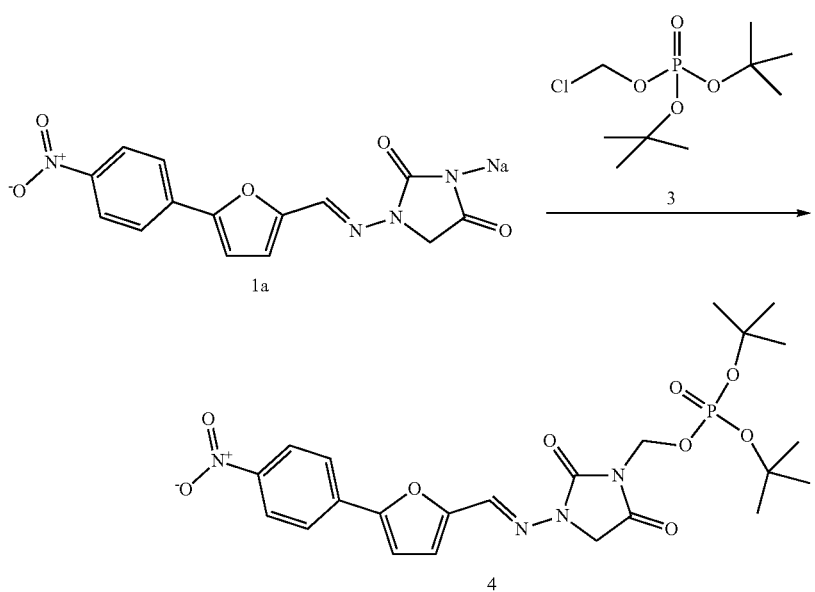

Sodium dantrolene (1 eq.) was dissolved in anhydrous dimethylformamide. Reagent 3 (1 eq) was added and the reaction mixture was stirred at 60° C. under nitrogen. After 4 h, another equivalent of reagent 3 was added and the reaction was stirred at 60° C. overnight. Then the reaction was diluted with ethyl acetate and washed twice with saturated sodium chloride. The layers were separated. The organic layers were dried over sodium sulfate and concentrated in vacuo. The crude product was purified using silica gel chromatography. The desired product was isolated in 90-95% purity. $^1$H NMR was consistent with that predicted for the desired product.

Example 1, Method A 1a was dried with $P_2O_5$ overnight. To a mixture of 1a (500 mg, 1.48 mmol) in DMF (10 mL) was added 3 (0.84 mL, 3.72 mmol) followed by NaI (245 mg, 1.63 mmol) at 0° C. The resultant mixture was stirred at room temperature for 64 h. The mixture was diluted with EtOAc (30 mL) and brine (20 mL). The organic layer was separated, washed with water (2×15 mL), dried over anhydrous Na$_2$SO$_4$, filtered, and evaporated. The crude residue was purified by flash chromatography (twice), eluting with 0-10% MeOH/CH$_2$Cl$_2$ to afford the desired compound 4 (355 mg, 45%) as a yellow solid.

Example 1, Method B: 1a was dried with P$_2$O$_5$ overnight. To a mixture of 1a (8.0 g, 23.8 mmol) in DMF (160 mL) was added 3 (6.5 mL, 28.79 mmol) followed by NaI (4.28 g, 28.55 mmol) at room temperature. The resultant mixture was stirred at room temperature for 40 h. The mixture was diluted with EtOAc (250 mL) and brine (60 mL). The organic layer was separated, washed with water (2×75 mL), dried over anhydrous Na$_2$SO$_4$, filtered, and evaporated. The residue was triturated with CH$_2$Cl$_2$-hexanes to give a yellow solid (~7 g). This solid was purified by flash chromatography (twice, deactivated SiO$_2$), eluting with 0-10% MeOH/CH$_2$Cl$_2$ to afford the desired compound 4 (1.92 g, 15%) as a yellow solid.

Example 2

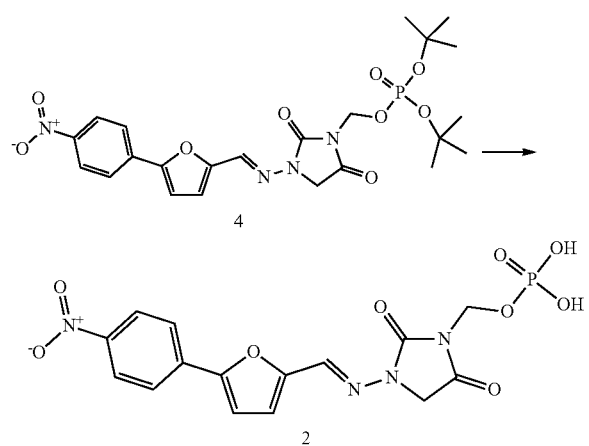

A sample of compound 4 was treated with 1 ml of 9/1 mixture of trifluoroacetic acid/water for 20-30 min at ambient temperature. The excess TFA was removed immediately using high vacuum and the resulting solid was collected by filtration, washed with water (5 ml) and air dried. The starting material, reaction mixture and final product were analyzed by LC/MS to determine if 2 reverts to dantrolene during the deprotection conditions. No reversion of 2 to dantrolene was observed. The $^1$H NMR of the product was consistent with that predicted for the desired product.

Example 2, Method A: To a mixture of 4 (886 mg, 1.65 mmol) in CH$_2$Cl$_2$ (9 mL) was added TFA (9 mL). The resultant mixture was stirred at room temperature for 3 h. The solvent was evaporated on a rotary evaporator to dryness. The resulting residue was triturated with hexanes for 1 h and the yellow solid was filtered and dried to yield the desired compound 2 (660 mg, 94%).

Example 3

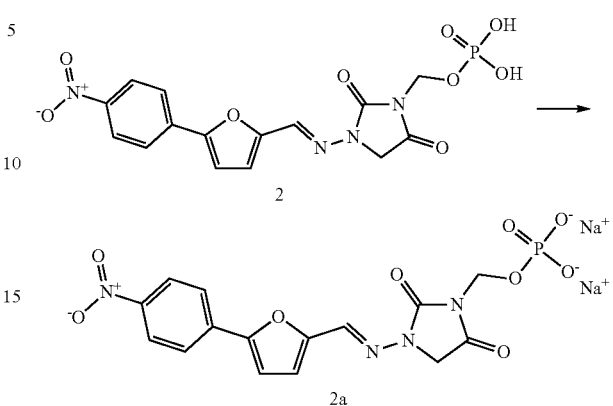

50 mg of 2 was mixed with 3 ml methanol (complete dissolution) and applied to 1 g of Na+ ion exchange column. The compound was eluted with methanol and after lyophilization gave 18 mg (36% recovery) of an orange solid. This material was dissolved in water and carefully titrated to pH 8.5 by the addition of small aliquots of 0.1 M NaOH, with stirring. The solution was then lyophilized to yield the orange solid, compound 2a. LC/MS of the sample before and after lyophilization was identical, which indicated no reversion to dantrolene occurred during the ion exchange. $^1$H NMR of the product was consistent with that predicted for the desired product.

Example 3, Method A: To a stirred suspension of 2 (500 mg, 1.17 mmol) in water (63 mL, HPLC grade) was added 0.1 N NaOH (23.6 mL, 2.34 mmol) at room temperature in 650 µL aliquots immediately followed by a quick vortex until the pH reached 8.5. The solution was filtered, and the filtrate was lyophilized overnight to give the title compound 2a (530 mg, 96%) as a yellow solid. MS (CI) m/z=424.9 [M]$^+$. $^1$H NMR (300 MHz, D$_2$O): δ 8.08 (d, J=8.8 Hz, 2H), 7.72 (d, J=8.8 Hz, 2H), 7.59 (s, 1H), 6.98 (d, J=3.6 Hz, 1H), 6.86 (d, J=3.6 Hz, 1H), 5.19 (d, J=6.0 Hz, 2H), 4.32 (s, 2H).

Example 4. Conversion of 2a to Dantrolene by Alkaline Phosphatase at 25° C.

Incubation with Alkaline Phosphatase

Prodrug 2a was incubated with purified alkaline phosphatase at 25° C. The final reaction mixture contained approximately 20 µg/mL prodrug and 50 µU/µL alkaline phosphatase (from calf intestine, Sigma #11097075001) in 1×PBS, pH 7.4. A control mixture containing 20 µg/mL prodrug without enzyme in 1×PBS pH 7.4 was also prepared. The enzyme reaction mixture was stored at 25° C. and 10 µL aliquots were injected and analyzed by HPLC at 0.9 h, 3.2 h, 5.5 h, 7.7 h, and 19.9 h. The control mixture was also stored at 25° C. and 10 µL aliquots were injected for analysis by HPLC at 1.5 h, 3.8 h, 6.6 h, 8.3 h, and 20.4 h.

Analysis of Samples by HPLC

Figure 2:
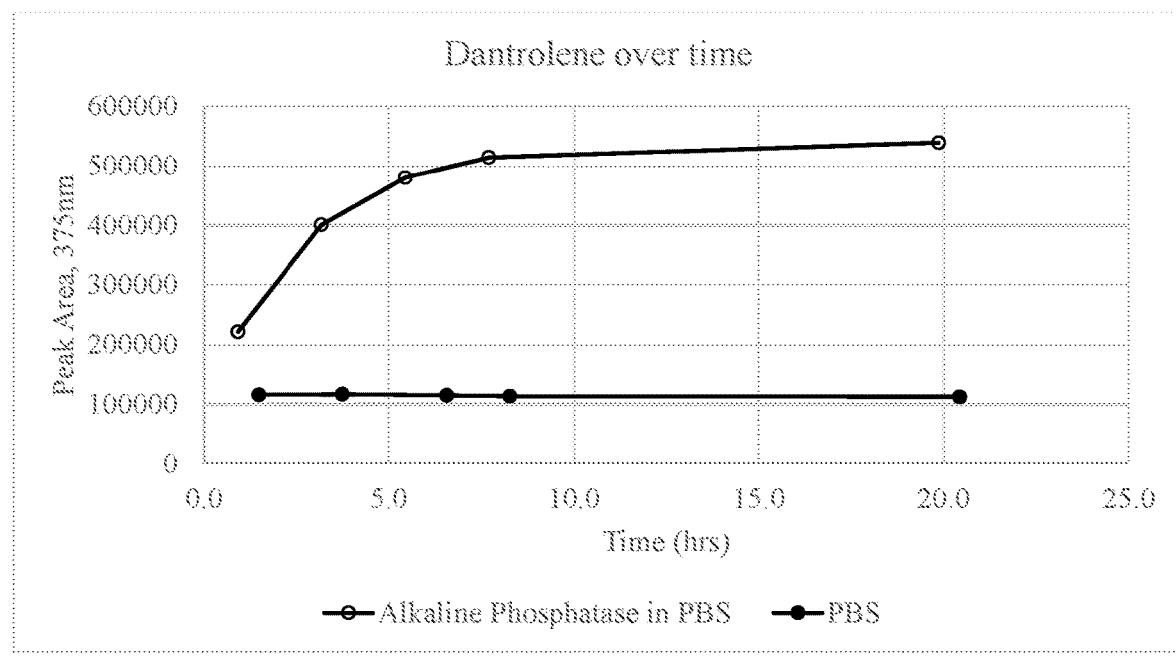
FIG. 2 depicts peak area over time for the conversion of a prodrug of the disclosure (2a) to dantrolene by alkaline phosphatase at 25° C.

Analysis was performed using a Waters 2695 Alliance System equipped with a PDA detector and a Restek Ultra C18 column (5 um, 250×4.6 mm) maintained at 25° C. Samples were analyzed using a gradient method with mobile phase A containing acetonitrile and mobile phase B containing 33:67 Acetonitrile:Phosphate buffer pH 6.9. The column was equilibrated with 100% mobile phase B and then held at this composition for 19 min. Then mobile phase A was increased to 55% over 5 min. The column was washed with 55% A for 2 min, returned to 100% B over 2 min, and then re-equilibrated with 100% B over 5 min for a total run time of 33 min. A 10 uL sample was injected and the analytes were detected by UV at 375 nm. The prodrug eluted at approximately 3.1 minutes and dantrolene eluted at approximately 15.4 minutes. Changes in peak area were monitored over time to determine conversion of the prodrug to dantrolene. The plots of peak area over time are shown in FIG. 1 and FIG. 2.

Example 5. Conversion of 2a to Dantrolene in Rat Plasma at 22° C.

Incubation with Plasma

An in vitro experiment was conducted by adding 40 μL of approximately 10 mg/mL 2a dissolved in DMF to 360 μL of previously frozen rat plasma from male Sprague Dawley rats at 22° C. The spiked plasma was stored at 22° C. and 50 μL aliquots were taken at 25 min, 3 h, and 20 h post-spike. The aliquots were immediately treated with 50 μL acetonitrile and mixed by vortexing followed by centrifugation at 4000 rpm for 5 min at 25° C. 50 μL supernatant was diluted 50-fold in 33:67 Acetonitrile:Phosphate buffer pH 6.9 and transferred to a glass vial for analysis by HPLC.

Analysis of Samples by HPLC

Figure 3:
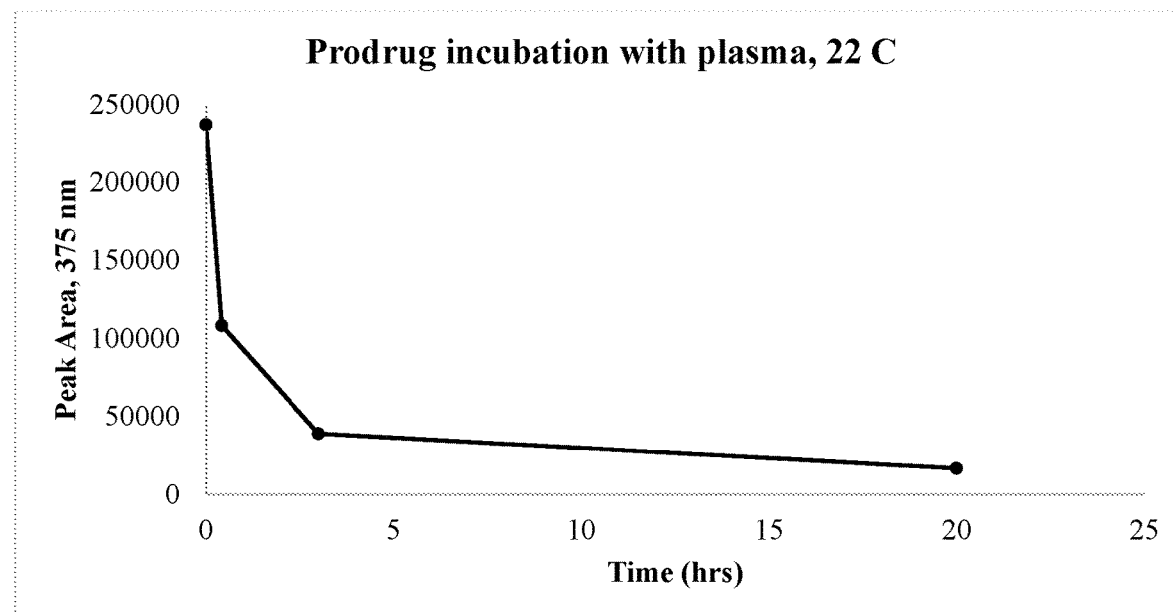
FIG. 3 depicts peak area over time for the conversion of a prodrug of the disclosure to dantrolene by rat plasma at 22° C.

Analysis was performed using a Waters 2695 Alliance System equipped with a PDA detector and a Restek Ultra C18 column (5 um, 250×4.6 mm) maintained at 25° C. Samples were analyzed using a gradient method with mobile phase A containing acetonitrile and mobile phase B containing 33:67 Acetonitrile:Phosphate buffer pH 6.9. The column was equilibrated with 100% mobile phase B and then held at this composition for 19 min. Then mobile phase A was increased to 55% over 5 min. The column was washed with 55% A for 2 min, returned to 100% B over 2 min, and then re-equilibrated with 100% B over 5 min for a total run time of 33 min. A 10 uL sample was injected and the analytes were detected by UV at 375 nm. The prodrug eluted at approximately 3.1 minutes and dantrolene eluted at approximately 15.4 minutes. Changes in peak area were monitored over time to determine conversion of the prodrug to dantrolene. See FIG. 3.

Example 6. Conversion of 2a to Dantrolene in Plasma at 37° C.

Incubation with Plasma

An in vitro experiment was conducted by adding 60 μL of approximately 10 mg/mL prodrug dissolved in DMF to 690 μL of previously frozen rat plasma from male Sprague Dawley rats at 37° C. The spiked plasma was stored at 37° C. and 50 μL aliquots were taken at 5, 10 min, 20 min, 30 min, 40 min, 50 min, 60 min, 100 min, 2.5 h, 3.5 h, 4 h, 5 h, and 6.5 h post-spike. The aliquots were immediately treated with 50 μL acetonitrile and mixed by vortexing followed by centrifugation at 4000 rpm for 5 min at 25° C. 50 μL supernatant was transferred to a glass vial for analysis by HPLC.

Analysis of Samples by HPLC

Figure 4:
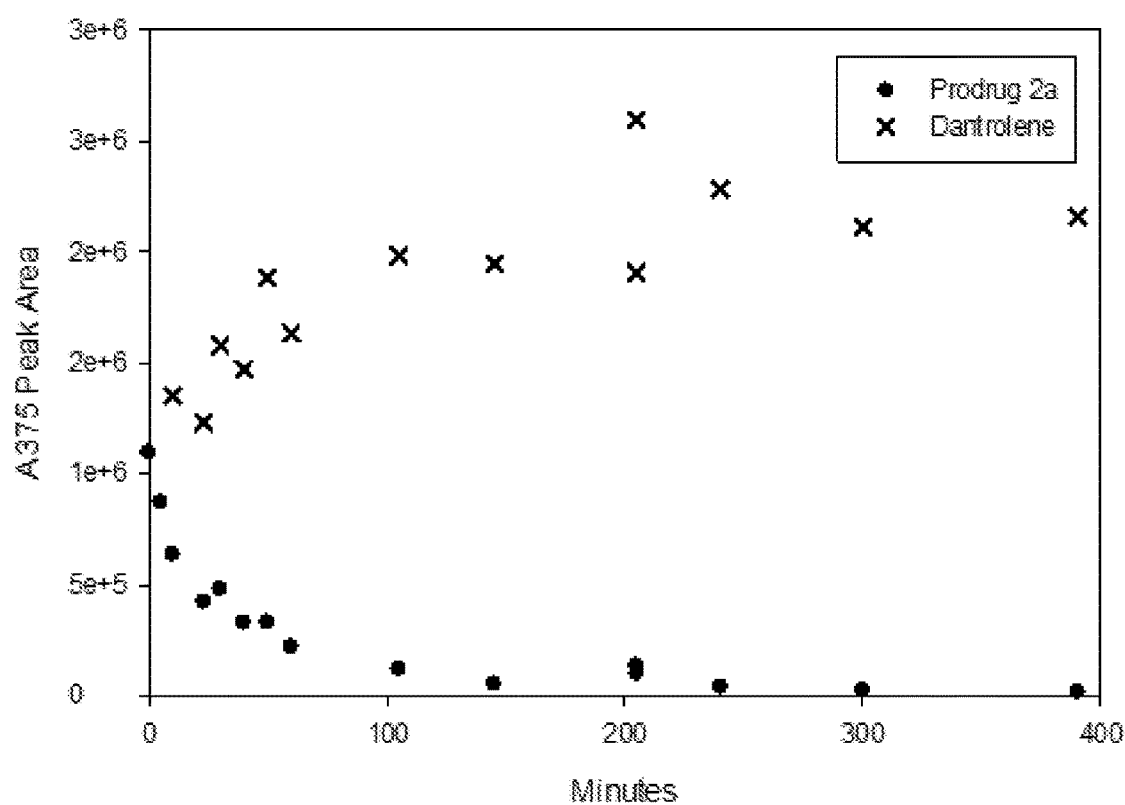
FIG. 4 depicts peak area over time for the conversion of a prodrug of the disclosure to dantrolene by rat plasma at 37° C.

Analysis was performed using a Waters 2695 Alliance System equipped with a PDA detector and a Restek Ultra C18 column (5 um, 250×4.6 mm) maintained at 25° C. Samples were analyzed using a gradient method with mobile phase A containing 0.1% trifluoroacetic acid in water and mobile phase B containing 0.1% trifluoroacetic acid in acetonitrile at a flowrate of 1.0 mL/min. The column was equilibrated with 67% mobile phase A/33% mobile phase B and then held at this composition for 19 min. Then mobile phase B was increased to 70% over 5 min. The column was washed with 70% B for 2 min, returned to 33% B over 2 min, and then re-equilibrated with 33% B over 15 min for a total run time of 47 min. A 5 uL sample was injected and the analytes were detected by UV at 375 nm. The prodrug eluted at approximately 6.5 minutes and dantrolene eluted at approximately 18.5 minutes. Changes in peak area were monitored over time to determine conversion of the prodrug to dantrolene. The plot of prodrug peak area over time is shown in FIG. 4.

Example 7. Bioavailability of Dantrolene after Administration of 2a to Rats

Methods

Compound 2a is formulated at 8 mg/mL in 5% aqueous mannitol (as a tonicity modifier), at pH 8.0. The formulation is administered IV, SC, or IM to cannulated Harlan Sprague Dawley rats (3 rats/group) from Envigo RMS, Inc. (Indianapolis, Ind.). Each group receives 7.5 mg/kg of 2a, which is equal to 5 mg/kg dantrolene equivalents (DE). Whole blood (0.1 mL) is collected via a jugular vein catheter at 0, 0.033 (IV only), 0.083, 0.167, 0.33, 0.66, 1, 3, 6, and 9 hours. Immediately after collection, the 0.1 mL of whole blood is added to 0.3 mL of acetonitrile to quench the prodrug bioconversion reaction. Samples are then placed on wet ice until centrifugation to remove precipitate. The precipitated whole blood matrix is analyzed for 2a, dantrolene, and the metabolite 5-OH dantrolene using a Phenomenex Synergi 4 μm Polar RP 80 Å, 75×2 mm column on a Waters Acquity UPLC system attached to an Applied Biosystems/MDS Sciex API 6500 LC/MS/MS system. Samples are quantified based on standard curves prepared with each analyte in the precipitated whole blood matrix.

Similarly, plasma concentration of dantrolene over time are measured after the administration of Ryanodex intravenously to rats at a dose of 5 mg kg$^{-1}$. Because Ryanodex is the 3.5 hydrate of dantrolene sodium, this is equivalent to a 3.9 mg kg$^{-1}$ dose of dantrolene on a molar basis, (i.e., 3.9 mg kg$^{-1}$ dantrolene equivalents (DE)).

Area Under the Curve (AUC) is calculated using the trapezoidal rule by SigmaPlot 12.5 software.

Results

Administration of 2a to rats by IV, IM, and SC routes will result in rapid appearance of dantrolene in the blood.

Example 8. Bioavailability of Dantrolene after Administration of Compounds of the Disclosure to Rats Methods Compounds of the disclosure are formulated in 5% aqueous mannitol (as a tonicity modifier). The formulation is administered IV, SC, or IM to cannulated Harlan Sprague Dawley rats (3 rats/group) from Envigo RMS, Inc. (Indianapolis, Ind.). Each group receives an amount equivalent to 5 mg/kg dantrolene equivalents (DE). Whole blood (0.1 mL) is collected via a jugular vein catheter at 0, 0.033 (IV only), 0.083, 0.167, 0.33, 0.66, 1, 3, 6, and 9 hours. Immediately after collection, the 0.1 mL of whole blood is added to 0.3 mL of acetonitrile to quench the prodrug bioconversion reaction. Samples are then placed on wet ice until centrifugation to remove precipitate. The precipitated whole blood matrix is analyzed for parent pro-drug, dantrolene, and the metabolite 5-OH dantrolene using a Phenomenex Synergi 4 µm Polar RP 80 Å, 75×2 mm column on a Waters Acquity UPLC system attached to an Applied Biosystems/MDS Sciex API 6500 LC/MS/MS system. Samples are quantified based on standard curves prepared with each analyte in the precipitated whole blood matrix.

Similarly, plasma concentration of dantrolene over time are measured after the administration of Ryanodex intravenously to rats at a dose of 5 mg kg$^{-1}$. Because Ryanodex is the 3.5 hydrate of dantrolene sodium, this is equivalent to a 3.9 mg kg$^{-1}$ dose of dantrolene on a molar basis, (i.e., 3.9 mg kg$^{-1}$ dantrolene equivalents (DE)).

Area Under the Curve (AUC) is calculated using the trapezoidal rule by SigmaPlot 12.5 software.

Results

Administration of compounds of the disclosure to rats by IV, IM, and SC routes will result in rapid appearance of dantrolene in the blood.

Example 9

Study Overview

The study object is to determine whether a compound of the disclosure (for example, compound 2a) has neuroprotective effects in a survival model in mammals, for example, dogs, pigs, rabbits, rodents (e.g., rats, mice, guinea pig), and primates (e.g., monkey, chimpanzee). One exemplary model is a GD (soman) survival model in rats.

Single doses of the compound of a compound of the disclosure will be administered following the onset of nerve agent-induced seizures. For example, single doses of the compound equivalent to 1 mg/mg to 30 mg/kg of dantrolene (e.g., 10 mg/kg or 30 mg/kg) are administered. Administration of the compound of the disclosure can be intravenously, subcutaneously, intramuscularly, transdermally, intraosseously. For example, the dose can be administered intravenously.

Survival can be facilitated by treatment with a nerve agent antidote. For example, asoxime chloride (HI-6) can be administered before nerve agent exposure, e.g., thirty minutes before subcutaneous (SQ) soman injection, atropine methyl nitrate one minute after SQ soman injection, and midazolam twenty minutes after the onset of soman-induced seizures that attain a Racine score of at least 3.

Controls include one group of untreated (naïve) animals and another group that will receive sterile water after the onset of nerve agent-induced seizures (e.g., 50 minutes after the onset of nerve agent-induced seizures).

A series of neurobehavioral tests are carried out over a period of time, for example, approximately 28 days following single-dose nerve agent exposure. On day the day after the testing time period, (e.g., day 29), all animal are sacrificed under anesthesia, for example, via exsanguination and intracardiac perfusion. Brain is collected from each animal for microscopic neuropathology examination, and heart is collected from each animal for possible pathology examination.

Materials

Soman (GD)—diluted with 0.9% Sodium Chloride. Soman is an organophosphorus nerve agent that deactivates acetylcholine esterase (AChE) by forming an adduct with the enzyme.

Chemical Name: Pinacolyl methyl phosphonofluoridate
    Formula: $C_7H_{16}FO_2P$
    Molecular Weight: 182.17
    MRIGlobal Lot #: GD090415-DOC-1
    Primary Standard ID: 13972-49-3
    Purity: 100%
    Storage Conditions: <4° C.

HI-6: Chemical Name: [(E)-[1-[(4-carbamoylpyridin-1-ium-1-yl)methoxymethyl]pyridin-2-ylidene]methyl]-oxoazanium;methanesulfonate (asoxime chloride)

Structure:

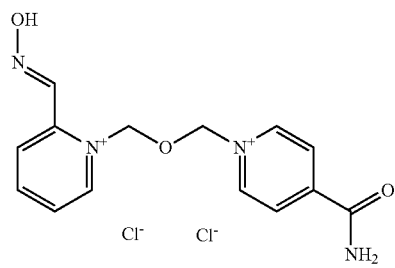 [SMILES: NC(=O)c1cc[n+](COC[n+]2ccccc2/C=N/O)cc1 ; [Cl-] ; [Cl-]]

Formula: $C_{14}H_{16}Cl_2N_4O_3$
Molecular Weight: 359.207

Atropine methyl nitrate: Chemical Name: (8,8-dimethyl-8-azoniabicyclo[3.2.1]octan-3-yl) 3-hydroxy-2-phenylpropanoate;nitrate Structure:

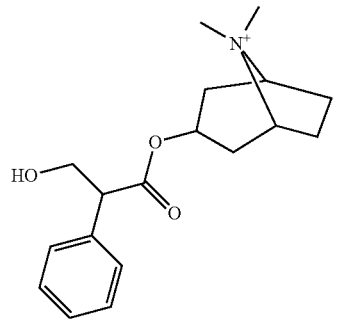 [SMILES: C[N+]1(C)C2CCC1CC(OC(=O)C(CO)c1ccccc1)C2]

Formula: $C_{18}H_{26}N_2O_6$
Molecular Weight: 366.414

Midazolam: Chemical Name: 8-chloro-6-(2-fluorophenyl)-1-methyl-4H-imidazo[1,5-a][1,4]benzodiazepin Structure:

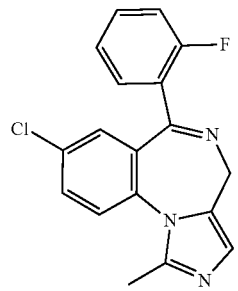 [SMILES: Cc1ncc2n1-c1ccc(Cl)cc1C(c1ccccc1F)=NC2]

Formula: $C_{18}H_{13}ClFN_3$
Molecular Weight: 325.771

Doses

HI-6, soman, atropine methyl nitrate, and midazolam:

Single doses of HI-6 (IP, 125 mg/kg); soman (SC, 154 µg/kg, 1.4× LD$_{50}$), atropine methyl nitrate (IM, 2 mg/kg); and midazolam (IM, 2 mg/kg) can be selected. This regimen is expected to cause convulsions that achieve a Racine score of at least 3 and an acceptable number of survivors for follow-up study.

Compounds of the Disclosure:

any compound of the disclosure, or a pharmaceutically acceptable salt thereof, as described herein may be administered. A preferred compound is compound 2a.

Dose Preparation

In those experiments using GD, GD is prepared in ice cold 0.9% Sodium Chloride according to SOP MRI-5821 "Preparation of Standards and Samples from Research Development and Testing Evaluation (RDTE) Dilute Solutions".

Racine Scale
1=immobilization & staring
2=head-nodding, "wet dog shakes'
3=forelimb clonus
4=bilateral forelimb clonus
5=bilateral forelimb clonus, rearing and loss of balance Neurobehavioral Tests Brain areas damaged by soman exposure can include the hippocampus and entorhinal, frontal, and parietal cortices. These areas contain structures and neural circuits for learning, memory formation, information processing, and other cognitive processes. To evaluate the potential neuroprotective effects of the compound of the disclosure, animal are evaluated using a series of behavioral tests that require learning, memory, sensory motor integration, and adaptive responses. Examples of such tests include: 1) Sucrose Preference Test and 2) Forced Swim Test.

Sucrose Preference Test

The Sucrose Preference Test (SPT) utilizes the natural inclination of rats to prefer sugar water over regular water. It is an established test to measure pleasure seeking behavior (hedonia) or lack of it (anhedonia) and requires animals to adapt to change in left vs. right placement of bottles containing tap water and 1% sucrose water.

Rats are housed individually with ad libitum access to food and water (single water bottle in each cage) before the SPT. For the acclimation portion of the SPT, 2 water bottles are introduced into each rat's home cage for 5-6 days. The water bottles were fitted with sipper tubes that minimize leakage and were weighed approximately every 24 hours. Following the acclimation phase, one water bottle is filled with approximately 200 mL of 1% sucrose solution, and the other water bottle with approximately 200 mL of tap water. Twenty-four hours later, the amount of fluid remaining in each bottle is recorded. The L/R placement of the bottles is then switched, and the amount of fluid remaining in each bottle is again recorded twenty-four hours later. The amount (mL) of sucrose solution consumed is expressed as a percent of the total volume of fluid consumed (sucrose water plus water) over each of the two 24-hour periods and compared across groups and days.

Forced Swim Test

The Forced Swim Test (FST) was developed in the late 1970s by Porsolt as a quick way to screen for efficacy of antidepressant drugs in rodents. The increased immobility that occurs towards the end of the 5-minute FST in untreated ("normal") rodents was interpreted to reflect "behavioral despair", and its reversal with antidepressant drugs correlated with the antidepressant efficacy of these agents in people. However, the construct validity of this test has come under question for many reasons, including: 1) acute effects of antidepressants are tested in FST whereas in clinically depressed patients, the drugs require 4-6 weeks for clinical improvement; 2) the dependent variable in the FST is the animal's acute response to the test and not a characteristic of the animal; and 3) the interpretation of floating behavior as 'behavioral despair' is anthropomorphic. It is now believed that the progressive immobility seen in untreated rats reflects an adaptive response to the acute stress of being placed in a container with no possibility of escape.

In the FST, swimming activity and immobility are measured in a glass cylindrical chamber (46 cm H×30 cm D) filled with water (30 cm height, 25° C.). Thermometers are used to ensure that the water temperature is a constant 24-26° C. for all animals. Two swimming sessions are carried out, one as an initial 15 min 'pre-test,' followed 24 hours later by a second 5 min 'test.' Test sessions are video recorded. Time spent actively swimming and time spent immobile is scored for each minute of the FST.

Neuropathology

The 7 brain sections from each animal are evaluated microscopically using a 6-point semi-quantitative scoring system. Microscopic lesions are graded on a 6-point scale:
0=normal
1=1-5 cells affected per 40× microscopic field
2=6-20 cells affected per 40× microscopic field
3=21-50 cells affected per 40× microscopic field
4=50%-80% of cells affected per 40× microscopic field
5=>80% of cells affected per 40× microscopic field Example 10. Preparation of 2b

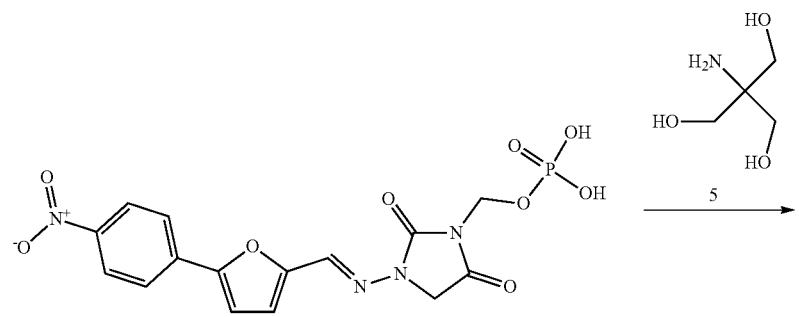

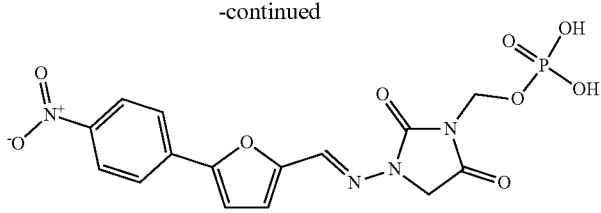
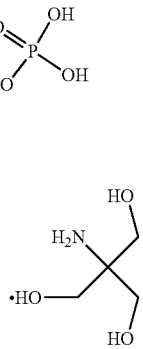

2b

To a stirred suspension of 2 (100 mg, 0.23 mmol) in water (12 mL, HPLC grade) was added Tris (5, 57 mg, 0.47 mmol) dissolved in water (5 mL) dropwise at room temperature. The pH of the final solution was 6.6. The solution was filtered, and the filtrate was lyophilized overnight to give the title compound 2b (150 mg, 95%) as a yellow solid. MS (CI) m/z=424.9 [M]+. $^1$H NMR (300 MHz, DMSO-$d_6$): δ 8.24 (m, 2H), 7.93 (m, 2H), 7.73 (m, 1H), 7.12 (m, 1H), 6.97 (m, 1H), 5.20 (m, 2H), 4.40 (m, 2H), 3.63 (m, 15H).

Example 11

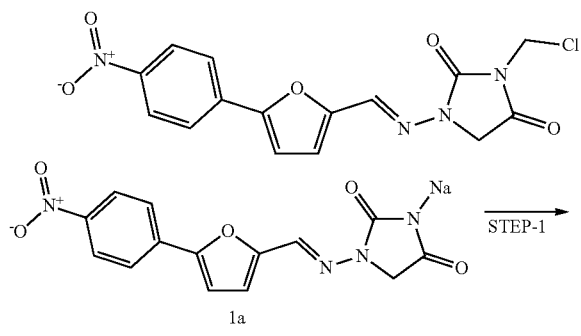

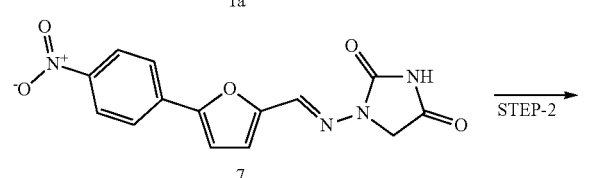

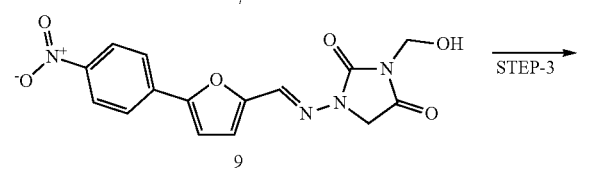

STEP 1: 1a was dried with $P_2O_5$ overnight. To a mixture of 1a (1.0 g, 2.97 mmol) in DMF (20 mL) was added glacial acetic acid (340 μL, 5.95 mmol) at room temperature. The mixture was stirred overnight at room temperature. The mixture was poured onto crushed ice, the solid was filtered and washed with water. The resultant wet solid was dried over anhydrous $P_2O_5$ overnight to get the desired compound 7 (920 mg, 98%) as a yellow solid.

STEP 2: To a suspension of 7 (1.35 g, 4.29 mmol) in water (45 mL) was added formalin (4.35 mL, 57.45 mmol, 37% formaldehyde in water) followed by $K_2CO_3$ (51 mg, 0.37 mmol). The mixture was stirred at room temperature for 24 h. The reaction mixture was filtered, and the yellow solid was washed with 3% aqueous formaldehyde and air dried for 24 h to give the desired compound 9 (1.2 g, 82%).

STEP 3: To a solution of 9 (615 mg, 1.78 mmol) in DMF:Acetone (40 mL, 15:25 mL) was added $PCl_3$ (1.2 mL, 13.71 mmol) slowly at 0° C. The reaction mixture was stirred for 10 min at 0° C. and 2 h at room temperature. Then the mixture was poured onto crushed ice, and the resulting yellow solid was filtered, washed with water (3×50 mL) and dried over $P_2O_5$ under vacuo for 16 h to give the desired compound 6 (600 mg, 92%). $^1$H NMR (300 MHz, DMSO-$d_6$): δ 8.33 (d, J=8.5 Hz, 2H), 8.03 (d, J=8.8 Hz, 2H), 7.87 (s, 1H), 7.48 (d, J=3.3 Hz, 1H), 7.11 (d, J=3.6 Hz, 1H), 5.42 (s, 2H), 4.53 (s, 2H).

Example 12

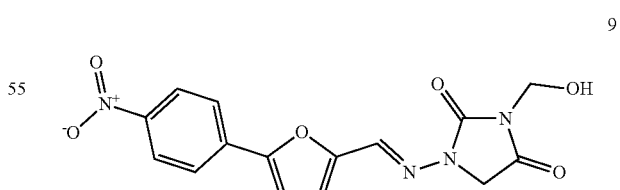

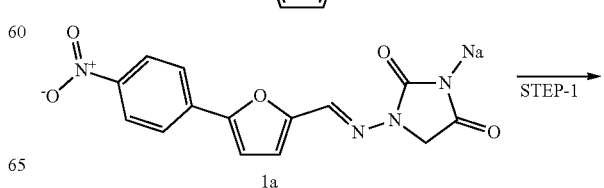

-continued

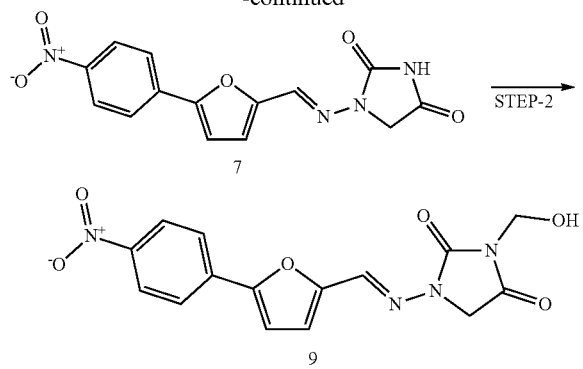

STEP 1: 1a was dried with P₂O₅ overnight. To a mixture of 1a (1.0 g, 2.97 mmol) in DMF (20 mL) was added glacial acetic acid (340 μL, 5.95 mmol) at room temperature. The reaction mixture was stirred overnight at room temperature. The mixture was poured onto crushed ice, the resulting solid was filtered and washed with water. The wet solid was dried over anhydrous P₂O₅ overnight to get the desired compound 7 (920 mg, 98%) as a yellow solid.

STEP 2: To a suspension of 7 (90 mg, 0.28 mmol) in water (2.6 mL) was added formalin (0.29 mL, 3.83 mmol, 37% formaldehyde in water) followed by K₂CO₃ (3.4 mg, 0.02 mmol). The mixture was stirred at room temperature for 24 h. The reaction mixture was filtered, and the yellow solid was washed with 3% aqueous formaldehyde and air dried for 24 h to give the desired compound 9 (86 mg, 88%). MS (CI) m/z=343 [M]⁻. ¹H NMR (300 MHz, DMSO-d₆): δ 8.32 (d, J=9.0 Hz, 2H), 8.03 (d, J=9.1 Hz, 2H), 7.83 (s, 1H), 7.47 (d, J=3.6 Hz, 1H), 7.08 (d, J=3.6 Hz, 1H), 6.52 (t, 1H), 4.85 (d, J=7.1 Hz, 2H), 4.45 (s, 2H).

Example 13

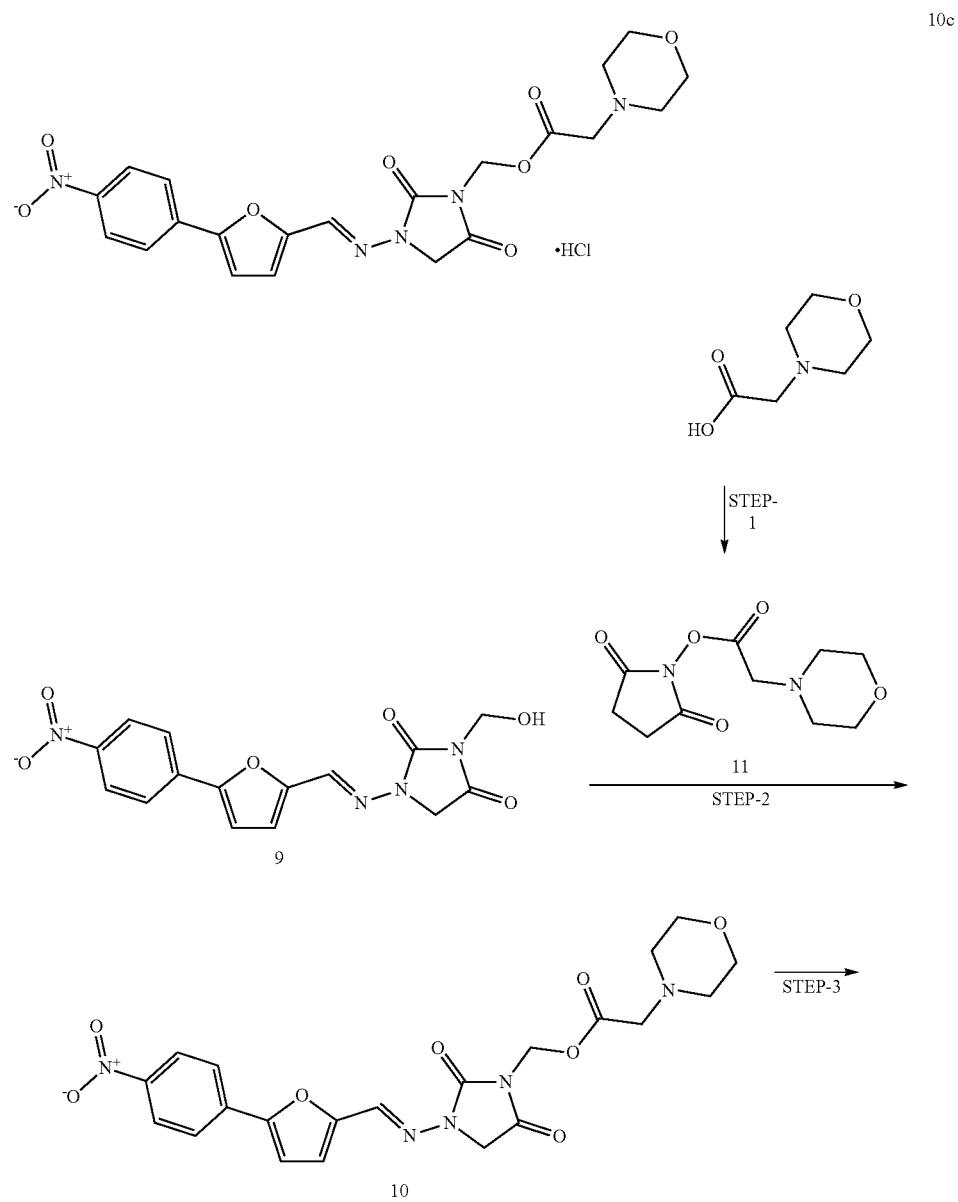

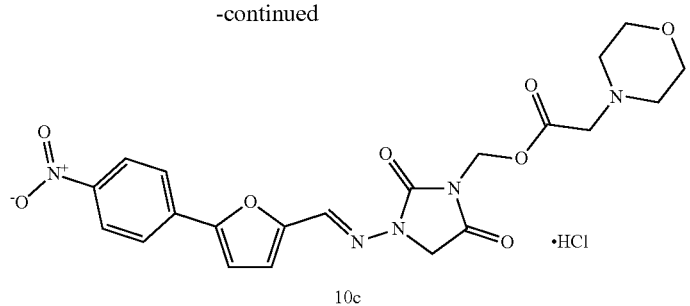

10c

STEP 1: Anhydrous DMF (0.8 mL, 10.33 mmol) was dissolved in anhydrous tetrahydrofuran (13 mL). This solution was added dropwise to a stirred solution of thionyl chloride (0.75 mL, 10.33 mmol) dissolved in tetrahydrofuran (9 mL) and cooled in an ice bath. After complete addition and 30 minutes on ice, the ice bath was removed and solid N-hydroxysuccinimide (832 mg, 7.23 mmol) was added (which completely dissolved) immediately followed by addition of solid pre-powdered morpholine acetic acid (1.0 g, 6.88 mmol). The morpholine acetic acid dissolved slowly giving a homogeneous solution that rapidly became cloudy. The reaction was left vigorously stirring overnight at room temperature. The white solid was washed with tetrahydrofuran and dried under vacuum, to yield the desired compound 11 (1.6 g, 96%) as a white solid.

STEP 2: To a solution of 9 (660 mg, 1.92 mmol) and 11 (928 mg, 3.83 mmol) in anhydrous DMF (12 mL) was added triethylamine (0.39 mL, 2.8 mmol). The resulting mixture was stirred overnight at 60° C. The reaction mixture was cooled to room temperature and purified by reverse phase column chromatography using acetonitrile-water as eluent. The column fractions were analyzed by HPLC and the fractions containing product were lyophilized to get the crude compound with 50% purity. This crude product was again purified by preparative HPLC using acetonitrile-water. The lyophilization of pure fractions gave the title compound 10 (100 mg, 10%) as a yellow solid.

STEP 3: To a stirred solution of 10 (75 mg, 0.16 mmol) in anhydrous 1,4-dixoane (4 mL) was added HCl (0.3 mL, 4N in 1,4-Dioxane) at room temperature and the resultant mixture stirred for 2 h. The solvents were evaporated on a rotary evaporator to dryness. The resulting residue was dissolved in water and lyophilized overnight to yield 10c (75 mg, 94%).

MS (CI) m/z=472.1 [M]$^+$. $^1$H NMR (300 MHz, DMSO-d$_6$): δ 8.33 (d, J=8.8 Hz, 2H), 8.03 (d, J=9.1 Hz, 2H), 7.89 (s, 1H), 7.49 (d, J=3.6 Hz, 1H), 7.11 (d, J=4.1 Hz, 1H), 5.60 (s, 2H), 4.54 (s, 2H), 3.32-3.81 (m, 10H). $^1$H NMR (300 MHz, D$_2$O): δ 8.17 (d, J=8.5 Hz, 2H), 7.81 (d, J=8.8 Hz, 2H), 7.60 (s, 1H), 6.93-7.02 (m, 1H), 6.88-6.92 (m, 1H), 5.73 (s, 2H), 4.39 (s, 2H), 4.26 (s, 2H), 3.90-4.09 (m, 4H), 3.30-3.52 (m, 4H).

Example 14

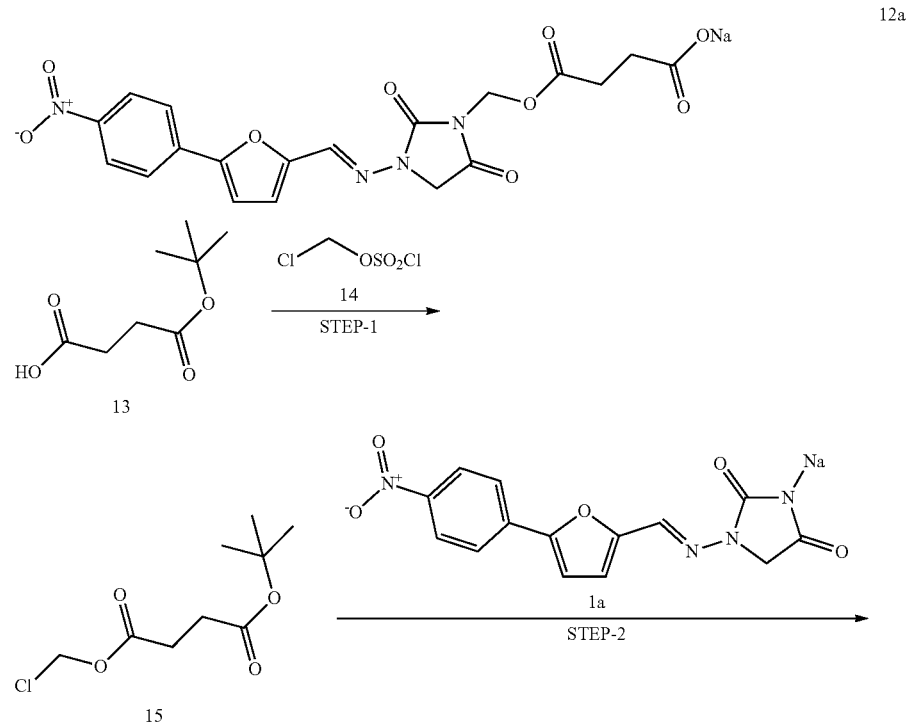

-continued

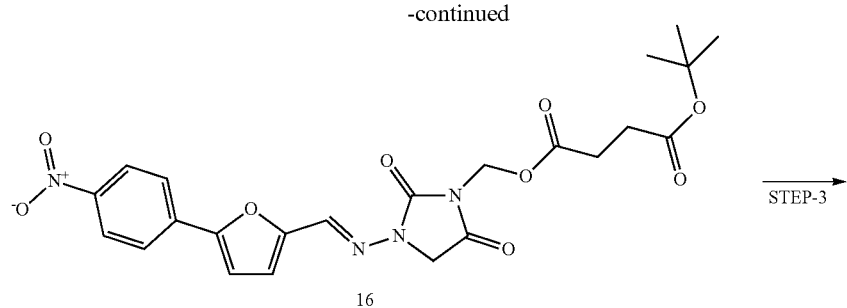

16

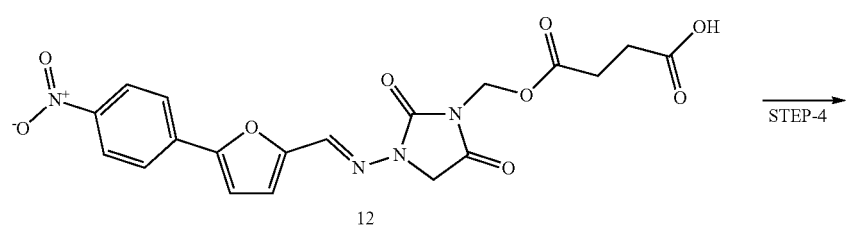

12

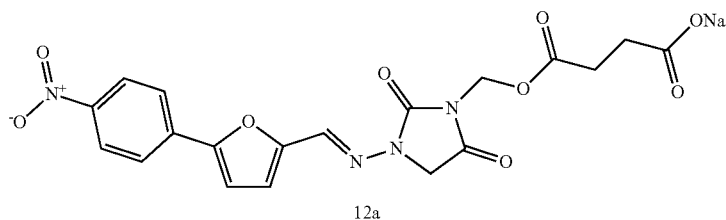

12a

STEP 1: To a mixture of K$_2$CO$_3$ (4.0 g, 28.94 mmol) and TBAHSO$_4$ (240 mg, 0.70 mmol) in water (8 mL) was added 13 (2.0 g, 11.48 mmol) in CH$_2$Cl$_2$ (8 mL) at 0° C. The resultant mixture was stirred for 20 min at 0° C. before adding 14 (1.3 mL, 12.85 mmol) and again stirred for 3 h. The organic layer was separated and washed with water (2×5 mL) and saturated aqueous brine (5 mL), The CH$_2$Cl$_2$ layer was dried over anhydrous Na$_2$SO$_4$, filtered and concentrated in vacuo. The crude residue was purified by flash chromatography eluting with 0-100% EtOAc/hexanes to get the desired compound 15 (2.2 g, 86%) as a colorless gum.

STEP 2: 1a was dried with P$_2$O$_5$ overnight. To a mixture of 15 (2.2 g, 9.87 mmol) in DMF (35 mL) was added 1a (1.66 g, 4.93 mmol) at room temperature. The resultant mixture was stirred at room temperature for 20 h. The mixture was diluted with EtOAc (50 mL) and washed with water (2×25 mL) and saturated aqueous brine (15 mL). The EtOAc layer was dried over anhydrous Na$_2$SO$_4$, filtered, and evaporated under vacuo. The crude residue was purified by flash chromatography eluting with 0-100% EtOAc/CH$_2$Cl$_2$ (twice) followed by trituration with CH$_2$Cl$_2$-hexanes to get the desired compound 16 (500 mg, 20%) as a yellow solid.

STEP 3: To a mixture of 16 (340 mg, 0.68 mmol) in CH$_2$Cl$_2$ (18 mL) was added TFA (1.8 mL). The resultant mixture was stirred overnight at room temperature. The solvents were evaporated on a rotary evaporator to dryness. The resulting residue was triturated with hexanes for 1 h and the yellow solid was filtered and dried to yield the desired compound 12 (300 mg, 99%).

STEP 4: To a stirred suspension of 6 (260 mg, 0.58 mmol) in water (36 ml, HPLC grade) was added 0.1 N NaOH (5.85 mL, 0.58 mmol) at room temperature in 400 aliquots immediately followed by a quick vortex. The pH of the final solution was 6.73. The solution was filtered, and the filtrate was lyophilized overnight to give the title compound 12a (150 mg, 55%) as a yellow solid. MS (CI) m/z=445.1 [M]$^+$. $^1$H NMR (300 MHz, DMSO-d$_6$): δ 8.34 (d, J=8.8 Hz, 2H), 8.04 (d, J=8.8 Hz, 2H), 7.87 (s, 1H), 7.49 (d, J=3.6 Hz, 1H), 7.11 (d, J=3.8 Hz, 1H), 5.43 (s, 2H), 4.51 (s, 2H), 2.40 (m, 2H), 2.15 (m, 2H).

Example 15
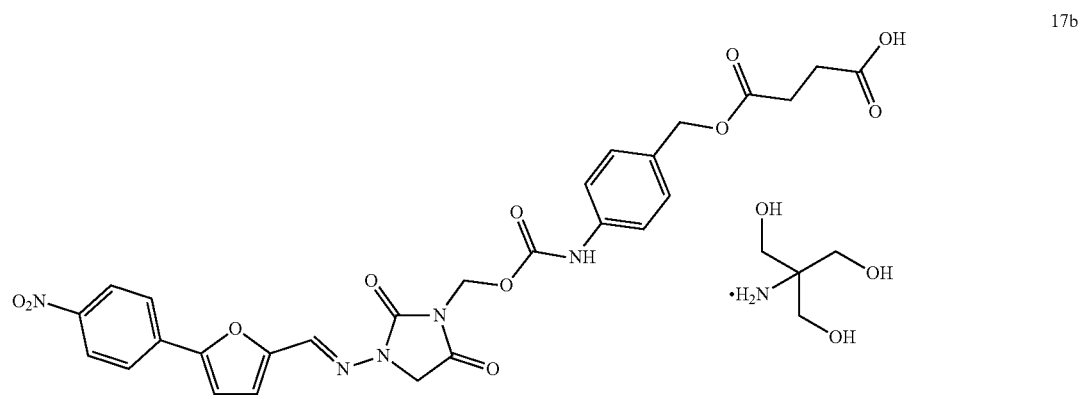
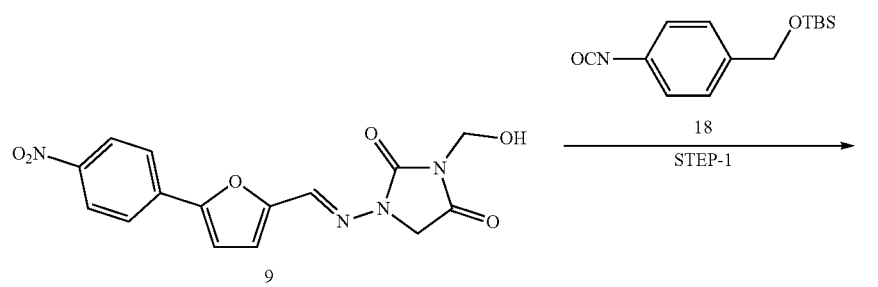
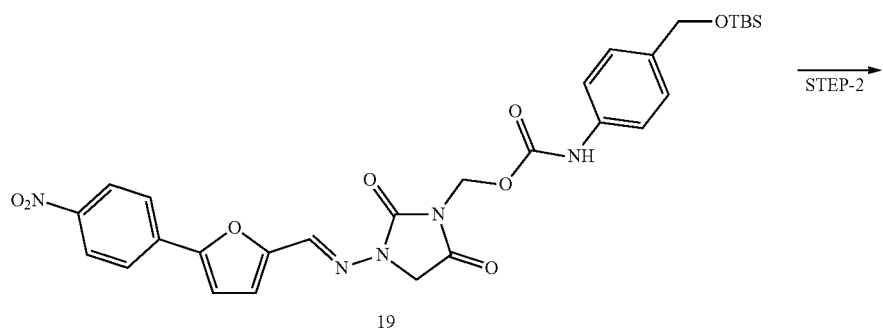
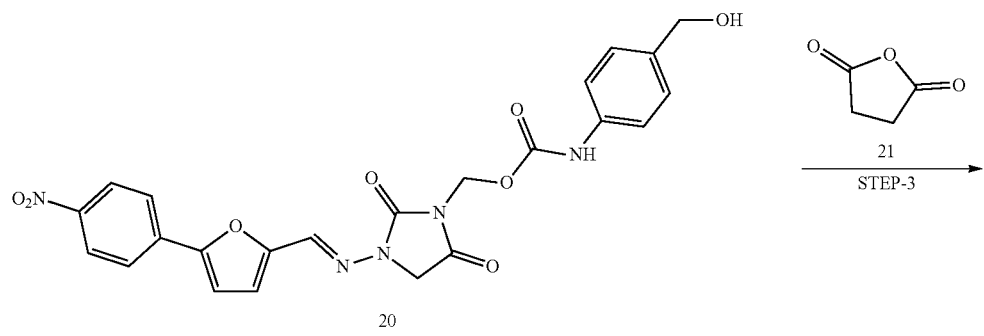

-continued

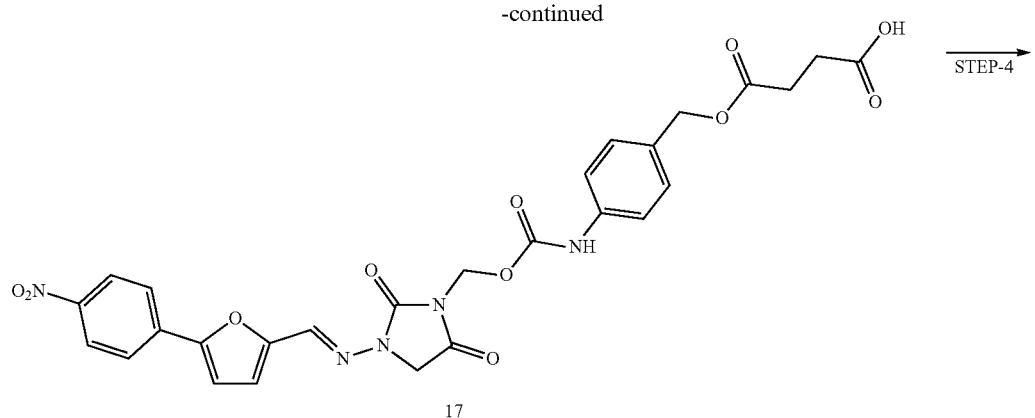

17

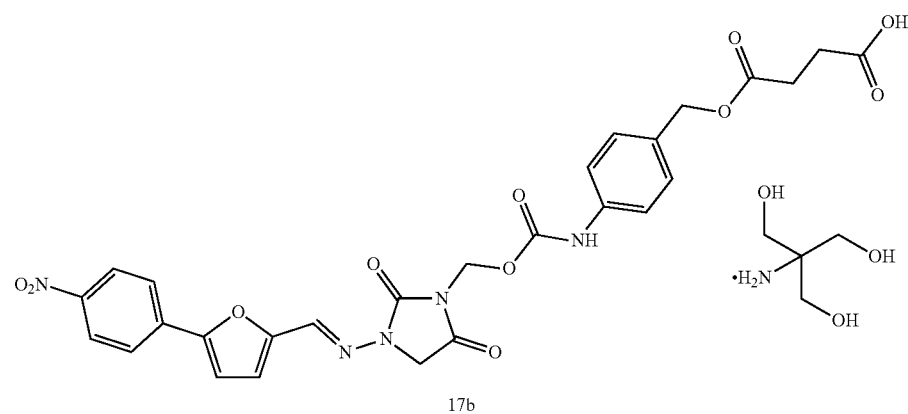

17b

STEP 1: To a solution of compound 9 (500 mg, 1.45 mmol) in anhydrous DMF (10 mL) was added compound 18 (488 mg, 1.85 mmol) in DMF (2 mL) followed by TEA (0.3 mL, 2.2 mmol). The resultant mixture was stirred for 16 h at room temperature. The mixture was diluted with EtOAc (50 mL), washed with water (2×15 mL). The organic layer was dried over anhydrous $Na_2SO_4$, filtered and evaporated to dryness. The crude product was purified twice by flash chromatography eluting with 0-10% MeOH/$CH_2Cl_2$ to obtain the desired compound 19 (350 g, 40%) as a yellow solid.

STEP 2: To a solution of compound 19 (200 mg, 0.32 mmol) in MeOH:1,4-Dioxane (1:1, 6 mL) was added p-toluenesulfonic acid monohydrate (63 mg, 0.32 mmol). The clear solution was stirred for 16 h at room temperature. The solvents were evaporated on a rotary evaporator to dryness. The residue was purified by flash chromatography eluting with 0-10% MeOH/$CH_2Cl_2$ to obtain the desired compound 20 (125 g, 77%) as a yellow solid.

STEP 3: To a solution of compound 20 (120 mg, 0.24 mmol) and compound 21 (26.4 mg, 0.26 mmol) in m-xylene: 1,4-dioxane (1:1, 16 mL) was added p-toluenesulfonic acid monohydrate (15 mg, 0.07 mmol) and 4 Å molecular sieves (100 mg). The resultant mixture was refluxed for 16 h. The reaction mixture was cooled to room temperature, diluted with 1,4-dioxane (30 mL) and filtered. The filtrate was evaporated, and the crude residue was purified twice by flash chromatography eluting with 0-10% MeOH/$CH_2Cl_2$ to get the desired compound 17 (16 mg, 11%) as a yellow solid.

STEP 4: To a stirred suspension of 17 (5 mg, 8.4 μmol) in water (3 mL, HPLC grade) was added 0.1 N Tris (90 μL, 8.9 μmol) dropwise at room temperature. The mixture was stirred at room temperature for 3 h. The solution was filtered, and the filtrate was lyophilized overnight to give the title compound 17b (6 mg, 100%) as a yellow solid. MS (CI) m/z=594.1 $[M]^+$. $^1$H NMR (300 MHz, DMSO-$d_6$): δ 9.96 (brs, 1H), 8.34 (d, J=8.8 Hz, 2H), 8.05 (d, J=8.5 Hz, 2H), 7.89 (s, 1H), 7.5 (d, J=3.2 Hz, 1H), 7.46 (d, J=8.8 Hz, 2H), 7.29 (d, J=8.5 Hz, 2H), 7.12 (d, J=3.5 Hz, 1H), 5.57 (s, 2H), 4.99 (s, 2H), 4.55 (s, 2H), 3.23-3.32 (m, 9H), 2.33-2.36 (m, 4H).

Example 16

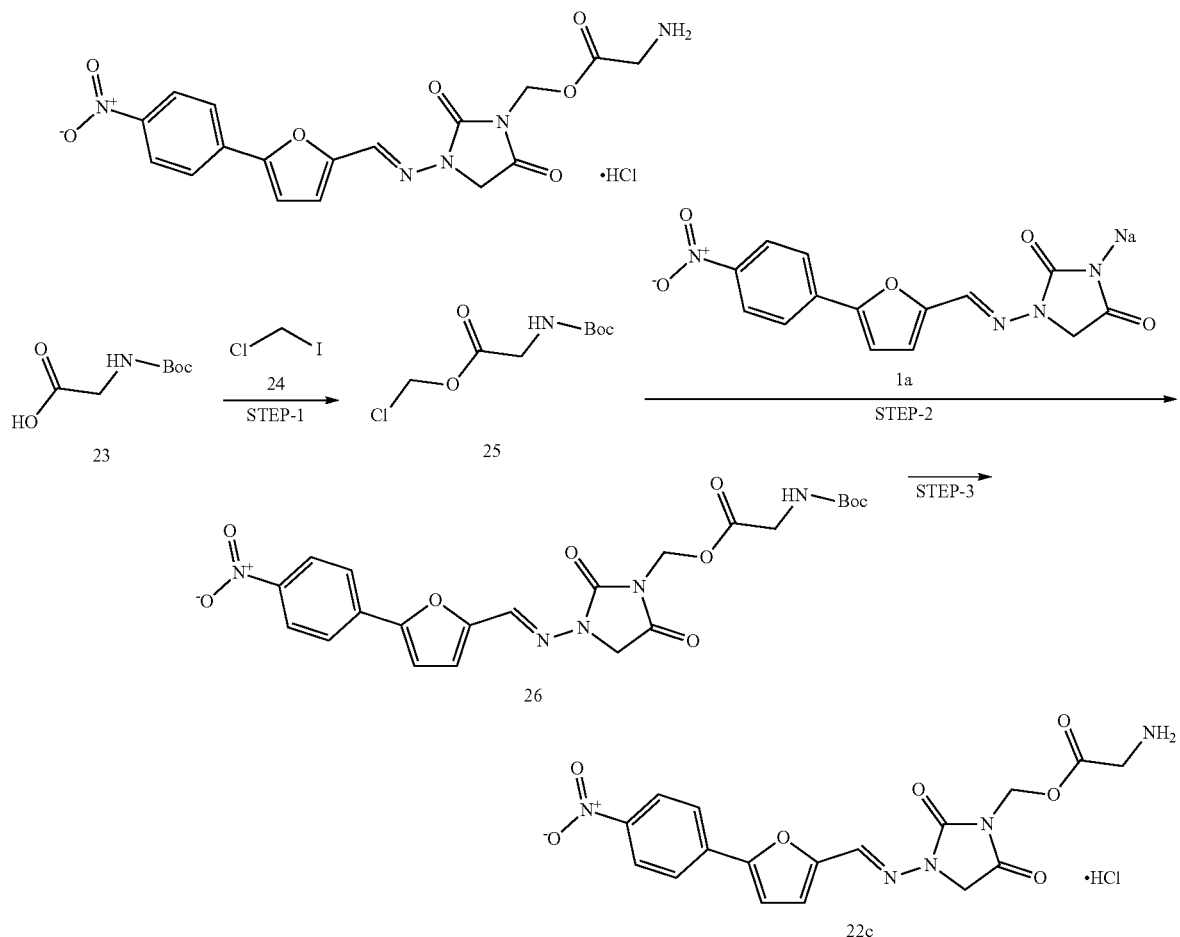

STEP 1: To a mixture of 23 (2.5 g, 14.28 mmol) in DMF (30 mL) was added triethylamine (3.47 mL, 24.93 mmol) followed by 24 (3.92 mL, 53.9 mmol) at room temperature. The resultant mixture was stirred at room temperature for 40 h. The mixture was diluted with EtOAc (100 mL) and water (50 mL). The EtOAc layer was washed with water (2×25 mL), 5% NaHCO$_3$ (25 mL), and saturated aqueous brine (15 mL). The EtOAc layer was dried over anhydrous Na$_2$SO$_4$ and concentrated in vacuo. The crude residue was purified by flash chromatography eluting with 0-100% EtOAc/hexanes to get the desired compound 25 (657 mg, 21%) as a colorless oil.

STEP 2: 1a was dried with P$_2$O$_5$ overnight. To a mixture of 1a (647 mg, 1.92 mmol) in DMF (12 mL) was added 25 (647 mg, 2.89 mmol) at room temperature. The resultant mixture was stirred at room temperature for 110 h. The mixture was diluted with EtOAc (40 mL), washed with water (2×15 mL), and saturated aqueous brine (15 mL). The EtOAc layer was dried over anhydrous Na$_2$SO$_4$, filtered, and evaporated under vacuo. The crude residue was purified by flash chromatography eluting with 0-100% EtOAc/CH$_2$Cl$_2$ to get the desired compound 26 (260 mg, 27%) as a yellow solid.

STEP 3: To a stirred solution of 26 (210 mg, 0.41 mmol) in anhydrous 1,4-dixoane (4 mL) was added HCl (4 mL, 4N in 1,4-Dioxane) at room temperature and the resultant mixture was stirred overnight. The solvents were evaporated on a rotary evaporator to dryness. The resulting residue was triturated with hexanes for 1 h and the yellow solid was filtered and dried to yield the title compound 22c (153 mg, 83%). MS (CI) m/z=402.1 [M]$^+$. $^1$H NMR (300 MHz, DMSO-d$_6$): δ 8.47 (brs, 3H), 8.34 (d, J=8.8 Hz, 2H), 8.04 (d, J=8.8 Hz, 2H), 7.91 (s, 1H), 7.50 (d, J=3.6 Hz, 1H), 7.12 (d, J=3.6 Hz, 1H), 5.61 (s, 2H), 4.56 (s, 2H), 3.85 (s, 2H).

Example 17. General UPLC Materials and Methods

LC-MS analysis was performed using an Agilent 1290 Infinity II Ultra Performance Liquid Chromatography system equipped with an Agilent Zorbax Eclipse Plus C18 column (2.1×50 mm, 1.8 μm). Elution was monitored at 210 nm and 385 nm using a diode array detector. Mobile phase A was water with 0.1% (v/v) trifluoroacetic acid, and mobile phase B was acetonitrile with 0.1% trifluoroacetic acid. For each sample, 10 μL was injected, and elution was performed using a linear gradient that began at 25% B and increased to 43% B over 4 minutes at a flow rate of 0.5 mL/min. The liquid chromatography system was coupled to an Agilent 6420 Triple Quadrupole mass spectrometer.

HPLC Standard Curves for Concentration Measurement

Approximately 1 mg of the compound of interest was weighed and dissolved to 1 mg/mL using 25% acetonitrile (in water v/v). A 10-fold dilution using 25% Acetonitrile of the prodrug was prepared to afford a 100 µg/mL solution. A series of 2-fold dilutions using 25% Acetonitrile were performed to obtain 50, 25, 12.5, and 6.25 µg/mL solutions. For each sample 10 µL was analyzed using the equipment and gradient described in the General UPLC Materials and Methods section. A standard curve for the concentration was generated by manually integrating the 385 nm chromatograms and plotting peak area as a function of concentration.

Pharmacokinetics Analysis

At each time point, 400 µL of blood was collected into a K2EDTA tube, and then placed on ice before centrifugation. After centrifugation, 100 µL of plasma was combined with 300 µL of acetonitrile before centrifugation to remove precipitated material. The samples were analyzed using the gradient in the General UPLC materials and methods section. A dantrolene standard curve was created for each experiment by dissolving 3.8 mg of dantrium in 14.9 mL of 50% methanol (v/v) in water. The dantrium was diluted into the supernatant of 1:3 precipitated rat blood:acetonitrile to generate the samples for the standard curve. The standard curve ranged from 5000 to 5 ng/mL. Dantrolene was monitored absorbance at 385 nm using the diode array detector and the multiple-reaction monitoring functionality of the mass spectrometer.

Compound 2a Reconversion in Plasma and Pharmacokinetics

Figure 5:
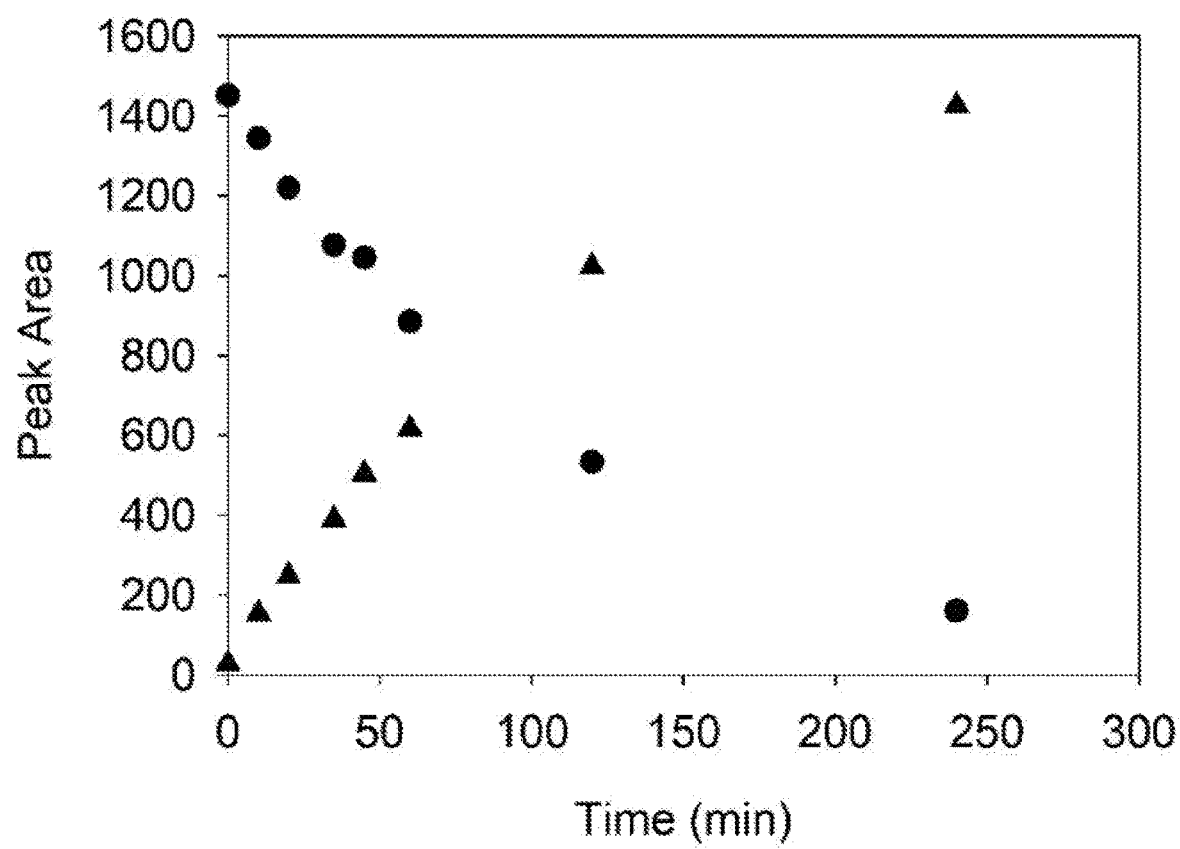
FIG. 5 depicts conversion of Compound 2a to dantrolene in rat plasma. Rat plasma was incubated with 100 μg/mL Compound 2a at 37° C. The area under the prodrug and dantrolene peaks in the 385 nm chromatograms are plotted against reaction time. Circles are the prodrug. Triangles are dantrolene.

To measure the conversion of Compound 2a to dantrolene in rat plasma, 1 mg of Compound 2a was dissolved to 1 mg/mL in water. A 100 µL aliquot of Compound 2a was combined with 900 µL plasma taken from Sprague Dawley rats. The plasma reaction was then placed in a 37° C. water bath. The initial concentration of Compound 2a in the plasma was 100 µg/mL. An initial sample was prepared by immediately removing 100 µL from the plasma reaction and mixed it with 100 µL of acetonitrile to quench the reaction, which caused precipitation. The insoluble material was pelleted by centrifugation at 15000 rpm for 5 minutes at 25° C. A sample for LC-MS analysis was prepared by combining 75 µL of the supernatant with 75 µL of water. The LC-MS analysis was performed by injecting 10 µL, and the samples were eluted using the equipment and gradient described in the General UPLC Materials and Methods Section. Additional samples were prepared after 10, 30, 45, 60, 120, 180, and 240 minutes. The loss of test compound and increase in dantrolene were quantified by manual integration of peaks in the 385 nm chromatograms (FIG. 5). The half-life of Compound 2a under these conditions was obtained by fitting an exponential function to the data. The half-life of Compound 2a was 82 minutes. A negative control where phosphate-buffered saline was used in place of rat plasma was also performed, and no conversion was observed.

Figure 6:
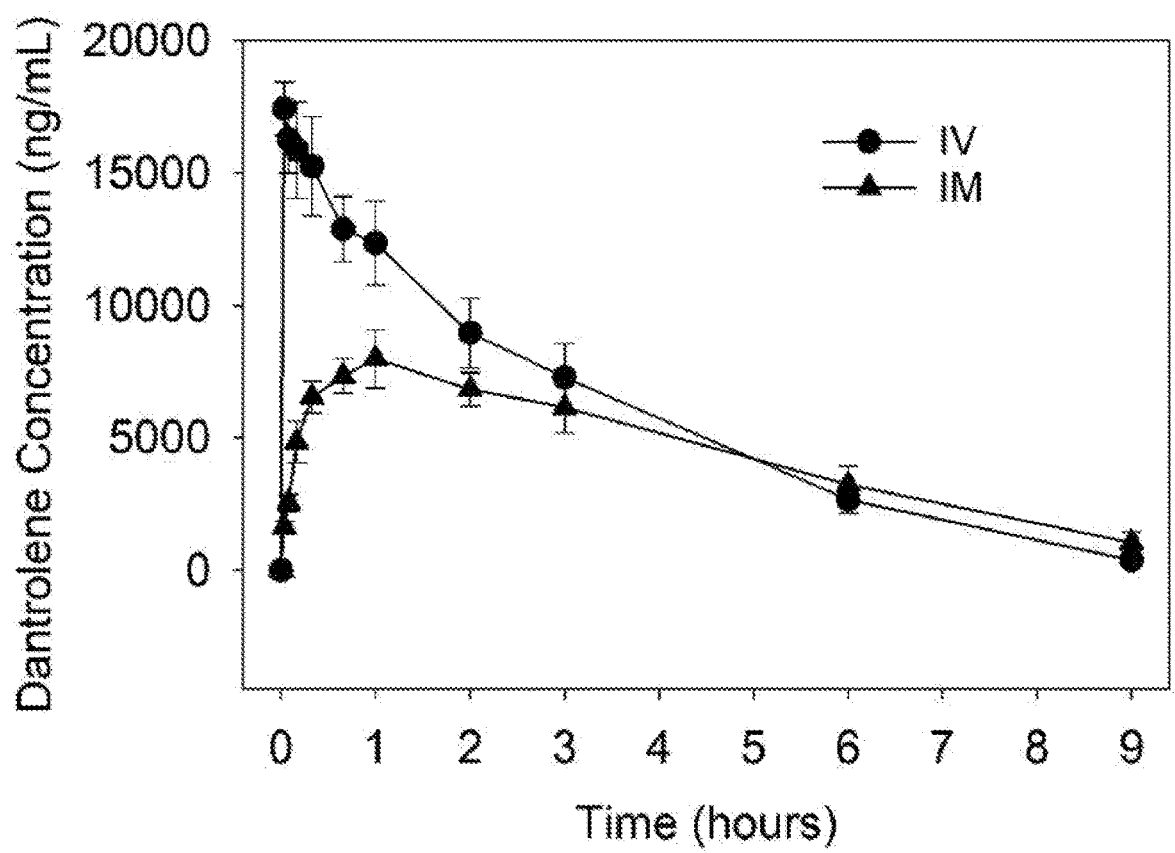
FIG. 6 depicts average concentration of dantrolene in rat plasma from animals dosed with 7.5 mg/kg prodrug 2a (n=5±SEM (standard error of the mean)). Quantification by absorbance at 385 nm.

The plasma pharmacokinetics of dantrolene following the administration of Compound 2a in live rats was assayed by dosing vein-cannulated Sprague-Dawley rats, and analyzing the plasma for dantrolene using LC-MS (FIG. 6 and Table 1). The dosing, sample collection, and analysis were performed by MPI Research. Intravenous doses were administered through the jugular-vein cannula. Intramuscular doses were administered by injecting half of the dose into the large muscle mass of the left hind limb and the other half of the dose into the right hind limb. There were five rats in each test group. Compound 2a was dissolved to 8 mg/mL in sterile-filtered aqueous 5% mannitol (w/v) to afford a dose level of 7.5 mg/kg and a dose volume of 0.94 mL/kg. Plasma was collected before administration and at 0.033, 0.083, 0.167, and 0.33, 0.66, 1, 2, 3, 6, 9 hours after administration.

In each experiment, only trace amounts of 2a was observed after administration of the compound by IV, IM, or SC routes. Consequently, only the concentration of dantrolene was followed for pharmacokinetic measurement.

TABLE 1

Plasma bioavailability of dantrolene after administration of Compound 2a via intravenous and intramuscular routes

| Administration Route | AUC (ng*hr/mL) | AUC (µg*hr/ml) | % Bioavailability |
|---|---|---|---|
| IV | 52148 | 5.2148 | 100 |
| IM | 40565 | 4.0565 | 77.8 |

Figure 7:
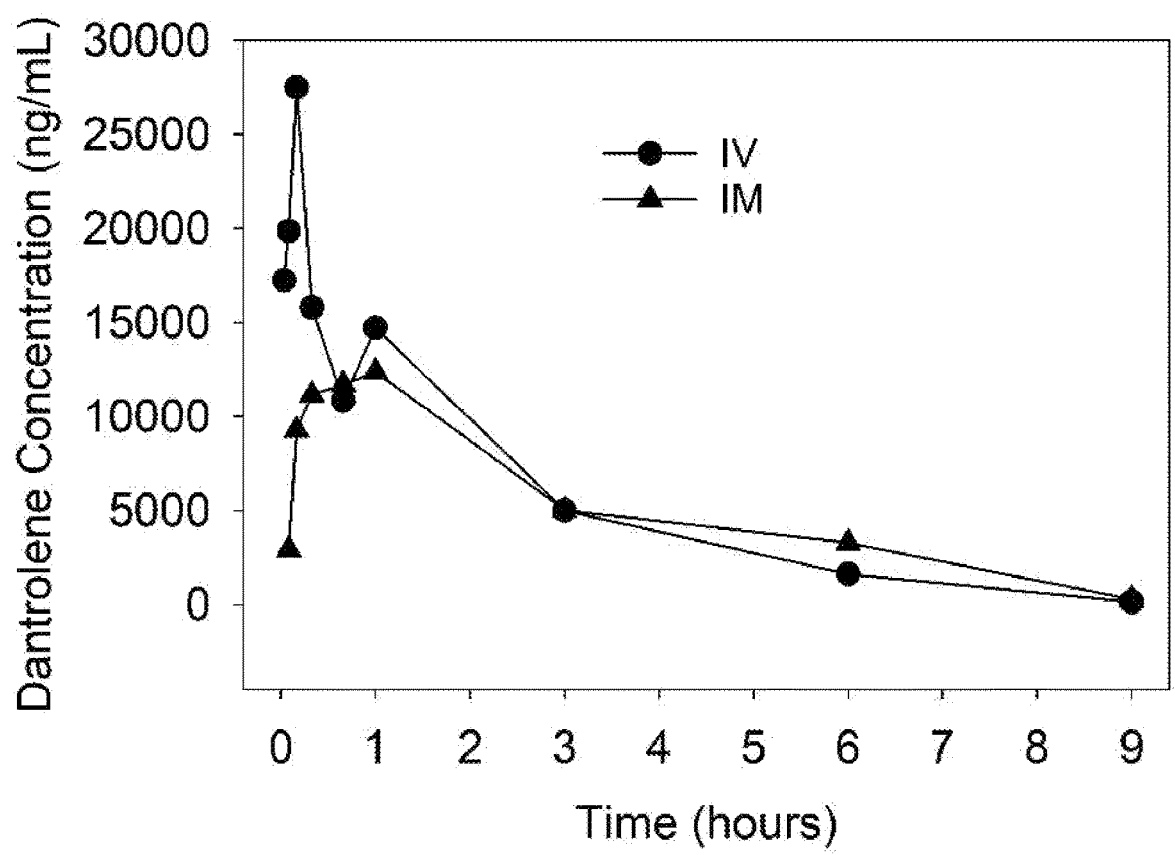
FIG. 7 depicts average concentration of dantrolene in rat whole blood from animals dosed with 7.5 mg/kg prodrug 2a (n=3). Quantification by absorbance at 385 nm.

In a second analysis, the whole-blood pharmacokinetics of Compound 2a in live rats was performed (FIG. 7 and Table 2). Each test group included three rats. Compound 2a was dissolved to 8 mg/mL in sterile-filtered aqueous 5% mannitol (w/v) to afford a dose level of 7.5 mg/kg and a dose volume of 0.94 mL/kg. Blood was collected before administration, 0.033, 0.083, 0.167, and 0.33, 0.66, 1, 2, 3, 6, 9 hours after administration. Whole blood samples were diluted 4-fold into acetonitrile and centrifuged to remove precipitate.

TABLE 2

Whole-blood bioavailability of dantrolene after administration of Compound 2a via intravenous and intramuscular routes

| Administration Route | AUC (ng*hr/mL) | AUC (µg*hr/ml) | % Bioavailability |
|---|---|---|---|
| IV | 47528 | 4.7528 | 100 |
| IM | 45297 | 4.5297 | 95.3 |

Figure 8:
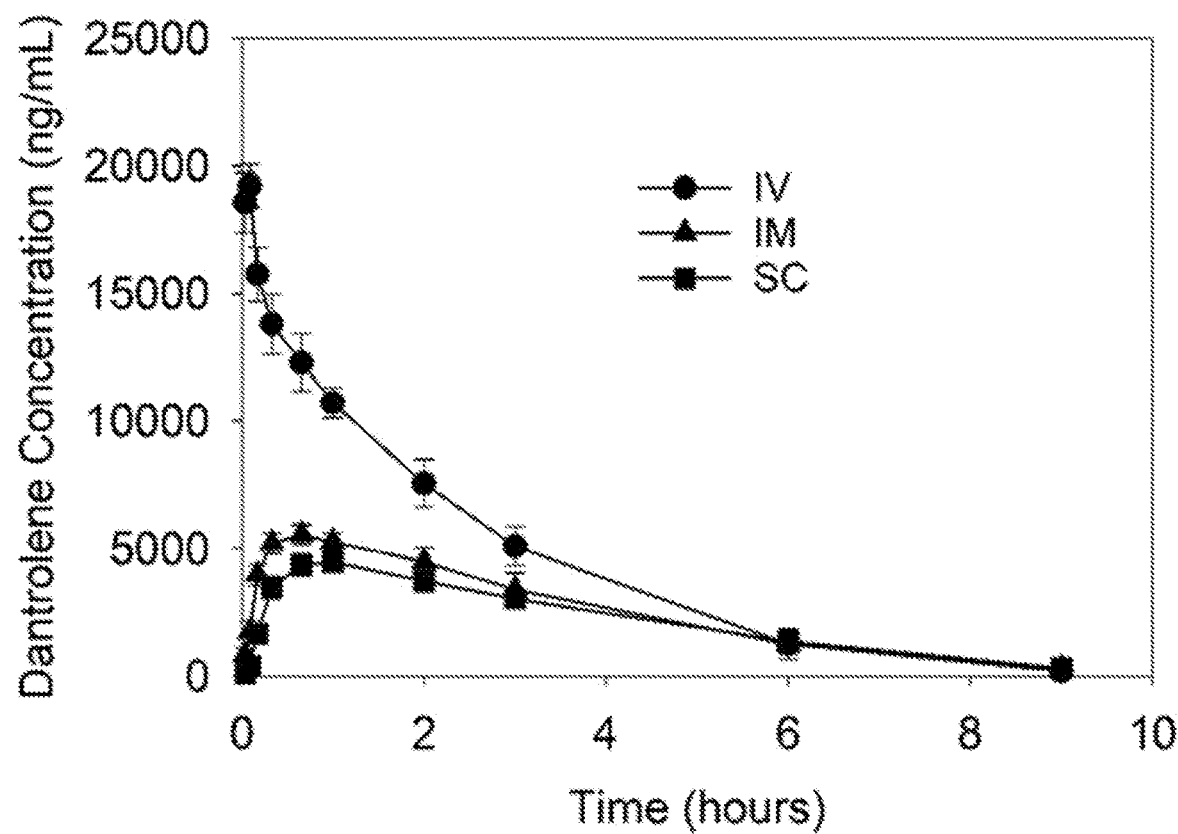
FIG. 8 depicts average concentration of dantrolene in rat plasma from animals dosed with 7.5 mg/kg prodrug 2a (n=5±SEM). Quantification by absorbance at 385 nm.
Figure 9:
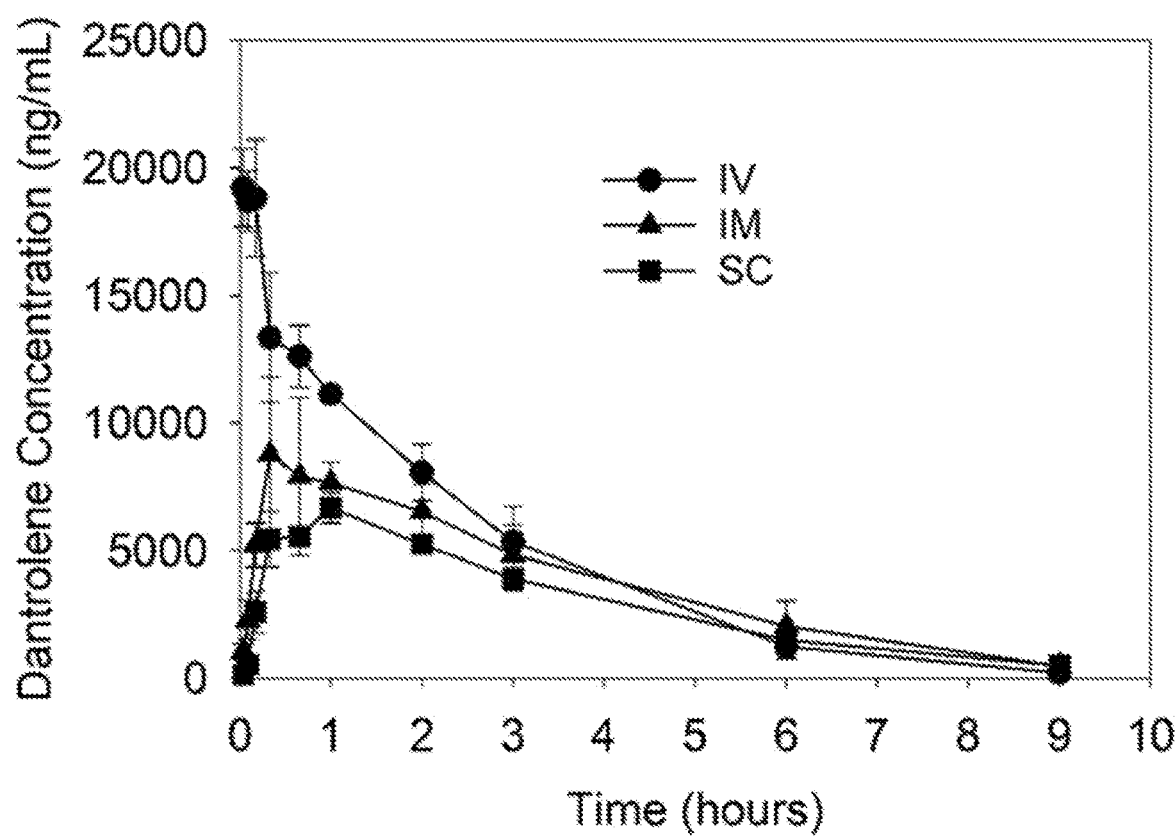
FIG. 9 depicts average concentration of dantrolene in rat whole blood from animals dosed with 7.5 mg/kg prodrug 2a (n=5±SEM). Quantification by absorbance at 385 nm.

Another pharmacokinetic analysis of Compound 2a in live rats was performed (FIGS. 8 and 9 Table 3). Each test group had five rats. Compound 2a was dissolved to 8 mg/mL in sterile-filtered aqueous 5% mannitol (w/v) to afford a dose level of 7.5 mg/kg and a dose volume of 0.94 mL/kg. Blood was collected before administration and at 0.033, 0.083, 0.167, and 0.33, 0.66, 1, 2, 3, 6, 9 hours after administration. Blood samples were diluted 4-fold into acetonitrile and centrifuged to remove precipitate. Plasma samples were obtained by placing blood into $K_2EDTA$ tubes and then centrifuging. The resultant plasma was then aspirated and diluted 4-fold into acetonitrile before another round of centrifuging to remove precipitated material.

TABLE 3

Bioavailability of dantrolene following administration of Compound 2a via intravenous, intramuscular, and subcutaneous routes

| Administration Route | AUC (ng*hr/mL) | AUC (µg*hr/ml) | % Bioavailability |
|---|---|---|---|
| IV [a] | 41906 | 4.1906 | 100 |
| IM [a] | 33861 | 3.3861 | 80.8 |
| SC [a] | 26388 | 2.6388 | 64.0 |
| IV [b] | 40298 | 4.0298 | 100 |
| IM [b] | 22857 | 2.2857 | 56.7 |
| SC [b] | 20019 | 2.0019 | 49.7 |

[a] Analysis of whole blood
[b] Analysis of plasma

Compound 2b Reconversion in Plasma and Pharmacokinetics

Figure 10:
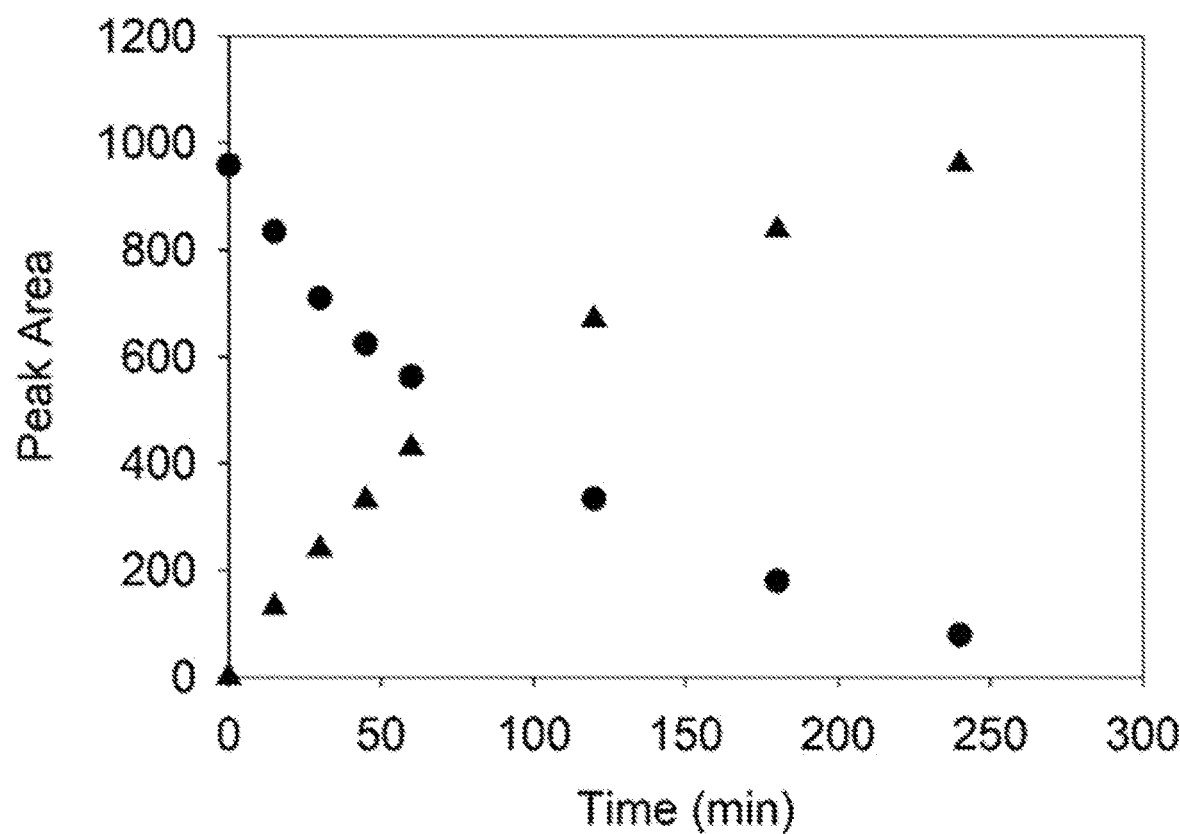
FIG. 10 depicts conversion of Compound 2b to dantrolene in rat plasma. Rat plasma was incubated with 100 μg/mL Compound 2b at 37° C. The area under the prodrug and dantrolene peaks in the 385 nm chromatograms are plotted against reaction time. Circles are the prodrug. Triangles are dantrolene.

To measure the conversion of Compound 2b to dantrolene in rat plasma, 1 mg of Compound 2b was dissolved to 1 mg/mL in water. A 100 µL aliquot of Compound 2b was combined with 900 µL of plasma taken Sprague Dawley rats. The plasma reaction was then placed in a 37° C. water bath. The initial concentration of Compound 2b in the plasma was 100 µg/mL. An initial sample was prepared by immediately removing 100 µL from the plasma reaction and mixing with 100 µL of acetonitrile to quench the reaction, which caused precipitation. The insoluble material was pelleted by centrifugation at 15000 rpm for 5 minutes at 25° C. A sample for LC-MS analysis was prepared by combining 75 µL of the supernatant with 75 µL of water. The LC-MS analysis was performed by injecting 10 µL, and the samples were eluted using the equipment and gradient described in the General UPLC Materials and Methods Section. Additional samples were prepared after 15, 30, 45, 60, 120, 180, and 240 minutes. The loss of Compound 2 and increase in dantrolene were quantified by manual integration of peaks in the 385 nm chromatograms (FIG. 10). The half-life of Compound 2b under these conditions was obtained by fitting an exponential function to the data. The half-life of Compound 2b was 77 minutes. A negative control where phosphate-buffered saline was used in place of rat plasma was also performed, and no conversion was observed.

Figure 11:
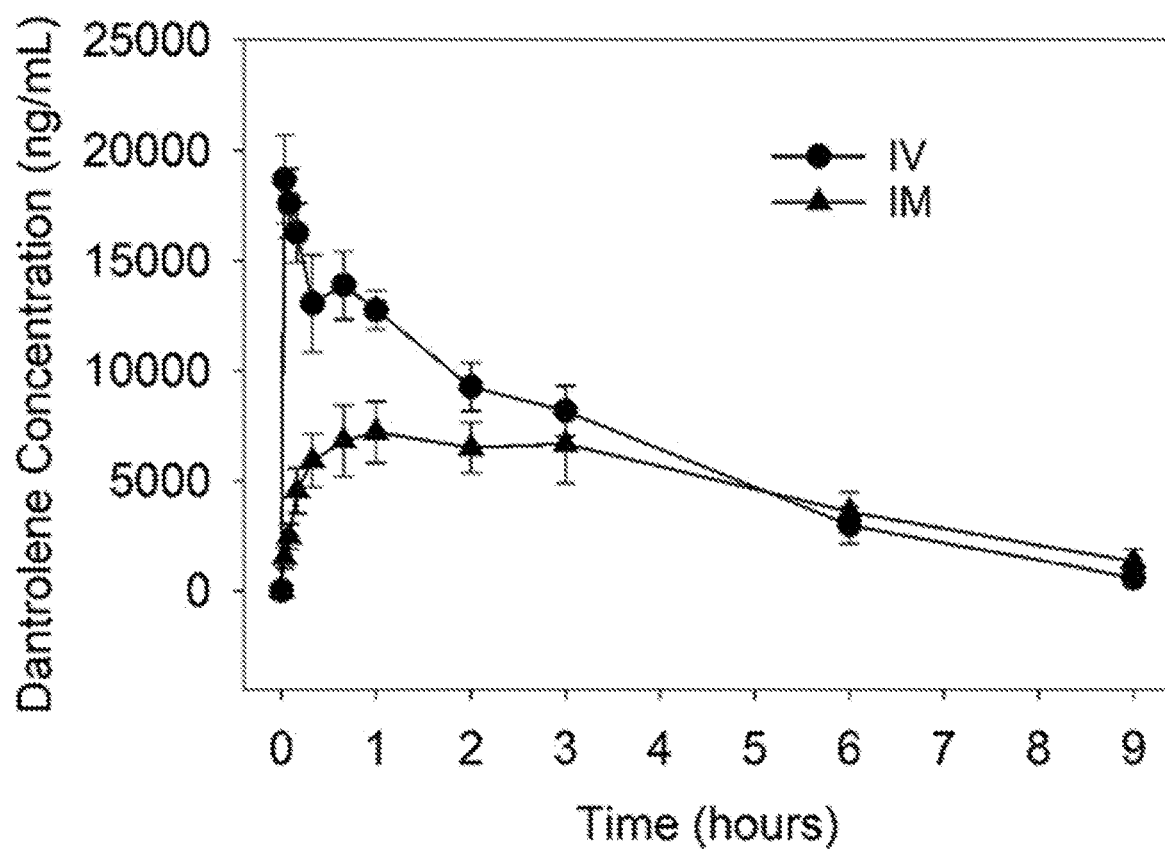
FIG. 11 depicts average concentration of dantrolene in rat plasma from animals dosed with 10.6 mg/kg of 2b (n=5±SEM). Quantification by absorbance at 385 nm.

The pharmacokinetics of dantrolene after administration of Compound 2b to live rats was assayed by dosing vein-cannulated Sprague-Dawley rats, and analyzing the blood for dantrolene using LC-MS (FIG. 11 and Table 4). The dosing, sample collection, and analysis were performed by MPI Research. Intravenous doses were administered through the jugular-vein cannula. Intramuscular doses were administered by injecting half of the dose into the large muscle mass of the left hind limb and the other half of the dose into the right hind limb. There were five rats in each test group. Compound 2b was dissolved to 11.4 mg/mL in sterile-filtered aqueous 5% mannitol (w/v) to afford a dose level of 10.6 mg/kg and a dose volume of 0.94 mL/kg. Plasma was collected before administration and at 0.033, 0.083, 0.167, and 0.33, 0.66, 1, 2, 3, 6, 9 hours after administration.

TABLE 4

Plasma bioavailability of dantrolene after administration of Compound 2b via intravenous and intramuscular routes.

| Administration Route | AUC (ng*hr/mL) | AUC (µg*hr/ml) | % Bioavailability |
|---|---|---|---|
| IV | 55748 | 5.5749 | 100 |
| IM | 41947 | 4.1947 | 75.2 |

Example 18. Compound 10c Reconversion in Plasma

Figure 12:
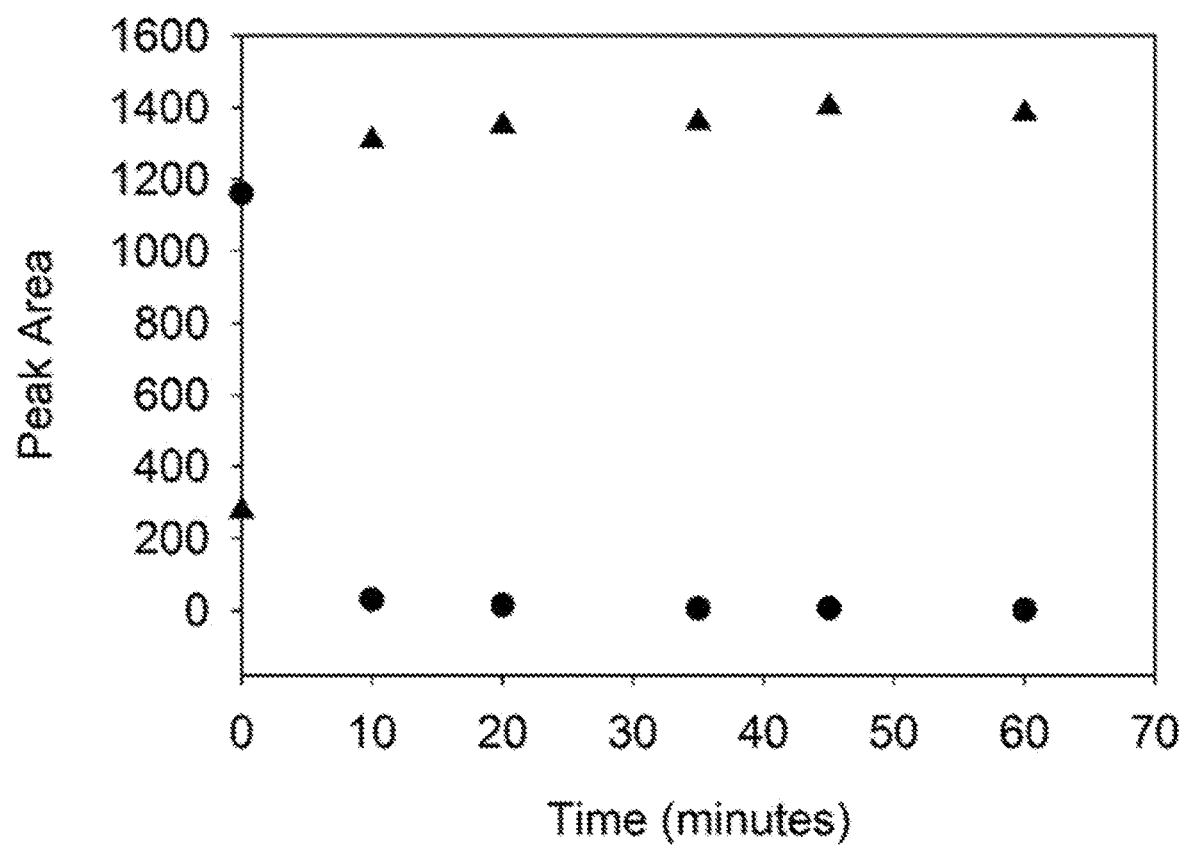
FIG. 12 depicts conversion of 10c to dantrolene in rat plasma. Rat plasma was incubated with 100 μg/mL Compound 10c at 37° C. The area under the prodrug and dantrolene peaks in the 385 nm chromatograms are plotted against reaction time. Circles are the prodrug. Triangles are dantrolene.

To measure the conversion of 10c to dantrolene in rat plasma, 0.9 mg of 10c was dissolved to 1 mg/mL in water. A 100 µL aliquot of 10c was combined with plasma taken Sprague Dawley rats. The plasma reaction was then placed in a 37° C. water bath. The initial concentration of 10c in the plasma was 100 µL/mL. An initial sample was prepared by immediately removing 100 µL from the plasma reaction and mixed it with 100 µL of acetonitrile to quench the reaction, which caused precipitation. The insoluble material was pelleted by centrifugation at 15000 rpm for 5 minutes at 25° C. A sample for LC-MS analysis was prepared by combining 75 µL of the supernatant with 75 µL of water. The LC-MS analysis was performed by injecting 10 µL, and the samples were eluted using the equipment and gradient described in the General UPLC Materials and Methods Section. Additional samples were prepared after 10, 20, 35, 45, and 60 minutes. The loss of 10c and increase in dantrolene were quantified by manual integration of peaks in the 385 nm chromatograms. The half-life of 10c under these conditions was obtained by fitting an exponential function to the data. Within the first 10 minutes of incubation with plasma 10c had been fully converted to dantrolene. The half-life was estimated to be 1.9 min. A negative control where phosphate-buffered saline was used in place of rat plasma was also performed, and slow conversion to dantrolene was observed. The half-life of 10c in phosphate-buffered saline was 294 minutes. See FIG. 12.

Example 19. Compound 12a Plasma Conversion and Pharmacokinetics

Figure 13:
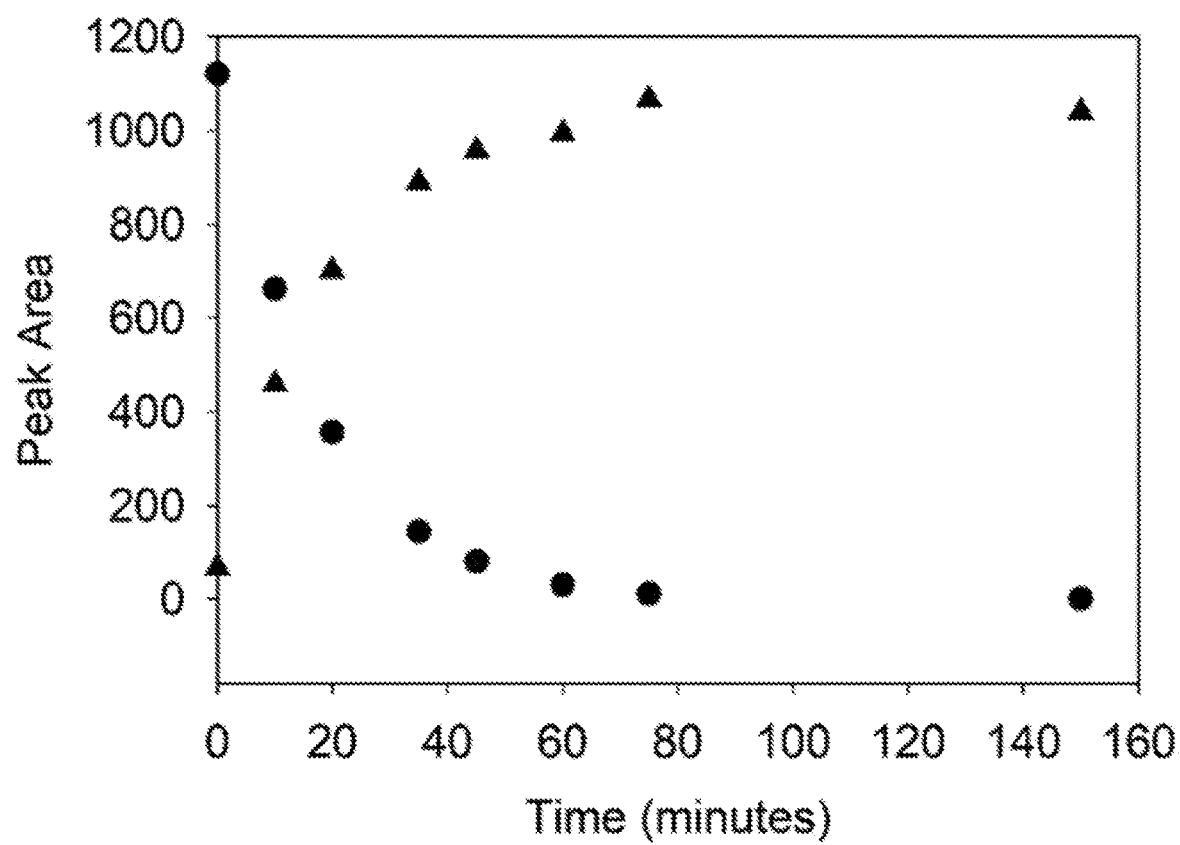
FIG. 13 depicts conversion of 12a to dantrolene in rat plasma. Rat plasma was incubated with 100 μg/mL 12a at 37° C. The area under the prodrug and dantrolene peaks in the 385 nm chromatograms are plotted against reaction time. Circles are the prodrug. Triangles are dantrolene.

To measure the conversion of 12a to dantrolene in rat plasma, a 1 mg/mL solution of 12a was prepared in water. A 100 µL aliquot of 12a was combined with plasma taken from Sprague Dawley rats. The plasma reaction was then placed in a 37° C. water bath. The initial concentration of 12a in the plasma was 100 µg/mL. An initial sample was prepared by immediately removing 100 µL from the plasma reaction and mixed it with 100 µL of acetonitrile to quench the reaction, which caused precipitation. The insoluble material was pelleted by centrifugation at 15000 rpm for 5 minutes at 25° C. A sample for LC-MS analysis was prepared by combining 75 µL of the supernatant with 75 µL of water. The LC-MS analysis was performed by injecting 10 µL, and the samples were eluted using the equipment and gradient described in the General UPLC Materials and Methods Section. Additional samples were prepared after 10, 20, 35, 45, 60, 75, and 150 minutes. The loss of 12a and increase in dantrolene were quantified by manual integration of peaks in the 385 nm chromatograms (FIG. 13). The half-life of 12a under these conditions was obtained by fitting an exponential function to the data. The half-life was calculated to be 12.2 min. A negative control where phosphate-buffered saline was used in place of rat plasma was also performed, the half-life was greater than 150 minutes.

Figure 14:
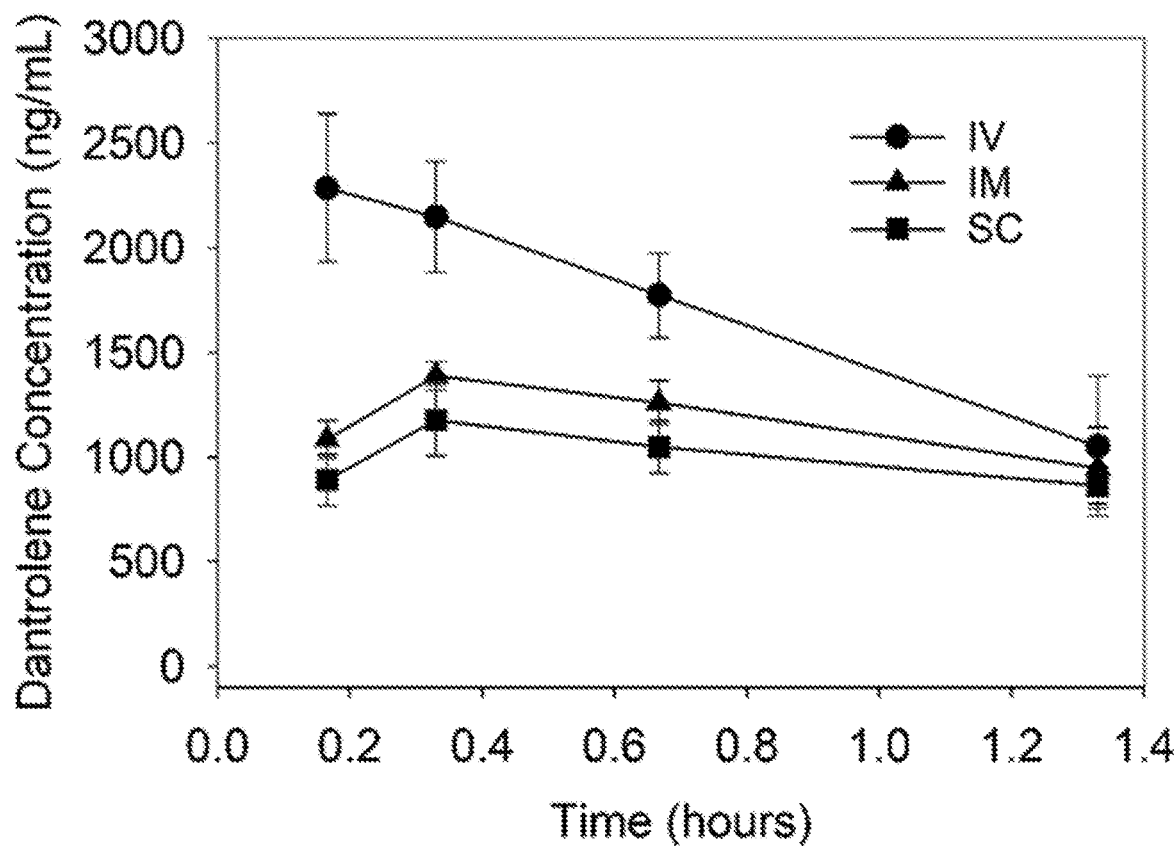
FIG. 14 depicts average concentration of dantrolene in whole blood from animals dosed with 4 mg/kg prodrug 12a (n=3±SEM). Quantification by absorbance at 385 nm.

The pharmacokinetic properties of 12a were assayed in the same manner as 22c except that compound was dissolved to 5 mg/mL in 5% mannitol to afford dose level 4 mg/kg and dose volume of 0.8 mL/kg (FIG. 14)

Example 20. Compound 17b Plasma Conversion

To generate a standard curve for calculating the concentration of 17b we dissolved 1 mg of compound in 200 µL of dimethylformamide to obtain a 5 mg/mL solution. The 5 mg/mL solution was diluted 5-fold into water and it was then centrifuged at 15000 rpm, 25° C., 5 min. The supernatant was used to make a 10-fold dilution into 25% acetonitrile in water to afford a 100 µg/mL solution. A series of 2-fold dilutions using 25% acetonitrile were performed to obtain 50, 25, 12.5, and 6.25 µg/mL solutions. These solutions were analyzed as described in the General UPLC Materials and Methods section except that the gradient was extended to end at 90% acetonitrile after 14.4 minutes.

To measure the conversion of 17b to dantrolene in rat plasma, a 1 mg/mL solution of 17b was prepared in water.

Figure 15:
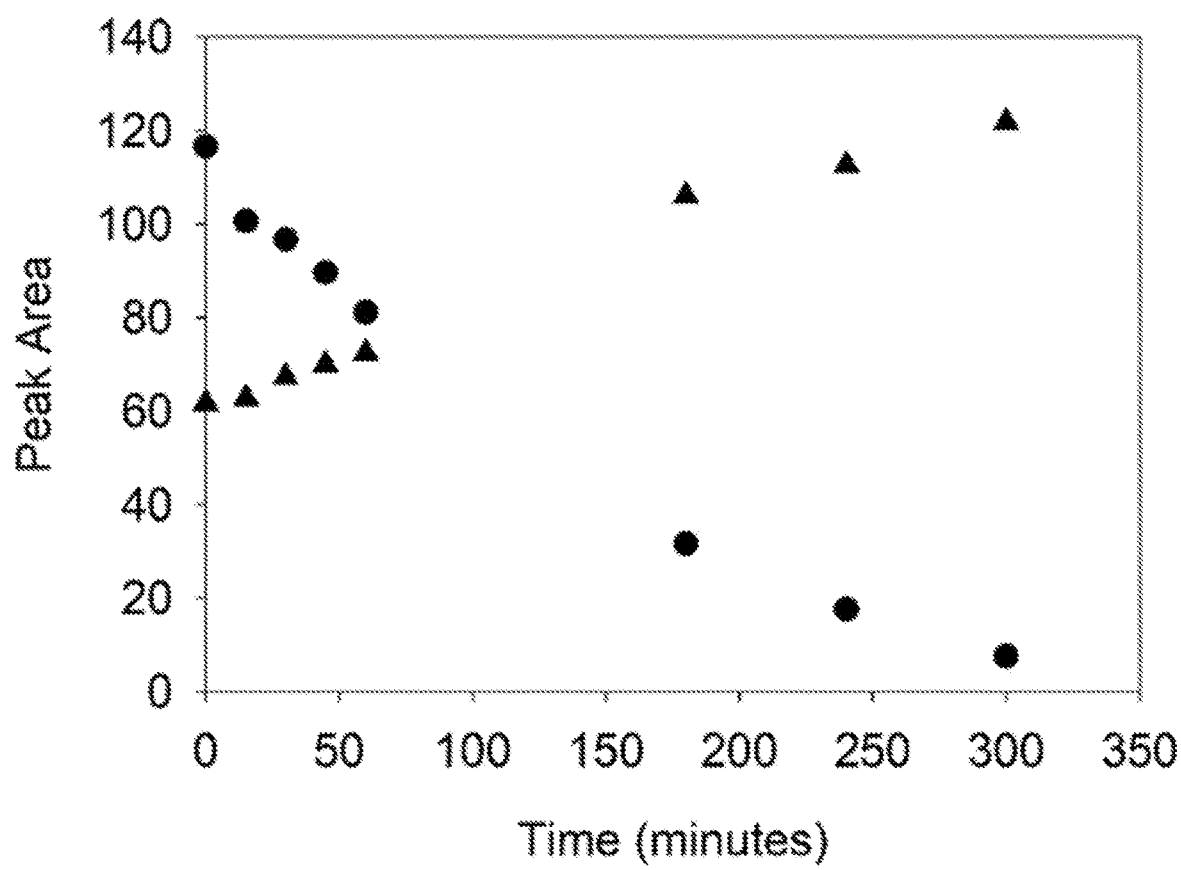
FIG. 15 depicts conversion version of 17b to dantrolene in rat plasma. Rat plasma was incubated with 100 μg/mL 17b at 37° C. The area under the prodrug and dantrolene peaks in the 385 nm chromatograms are plotted against reaction time. Circles are the prodrug. Triangles are dantrolene.

A 100 µL aliquot of 17b was combined with 900 µL plasma taken from Sprague Dawley rats. The plasma reaction was then placed in a 37° C. water bath. The initial concentration of 17b in the plasma was 100 µg/mL. An initial sample was prepared by immediately removing 100 µL from the plasma reaction and mixed it with 100 µL of acetonitrile to quench the reaction, which caused precipitation. The insoluble material was pelleted by centrifugation at 15000 rpm for 5 minutes at 25° C. A sample for LC-MS analysis was prepared by combining 75 µL of the supernatant with 75 µL of water. The LC-MS analysis was performed by injecting 10 µL, and the samples were eluted using the equipment described in the General UPLC Materials and Methods Section and the extended method described in the preceding paragraph. Additional samples were prepared after 15, 30, 45, 60, 180, 240 and 300 minutes. The loss of 17b and increase in dantrolene were quantified by manual integration of peaks in the 385 nm chromatograms (FIG. 15). The half-life of 17b under these conditions was obtained by fitting an exponential function to the data. The half-life was calculated to be 94.5 min. A negative control where phosphate-buffered saline was used in place of rat plasma was also performed, the half-life was estimated to be 447 minutes.

Example 21. Compound 22c Plasma Conversion and Pharmacokinetics

Figure 16:
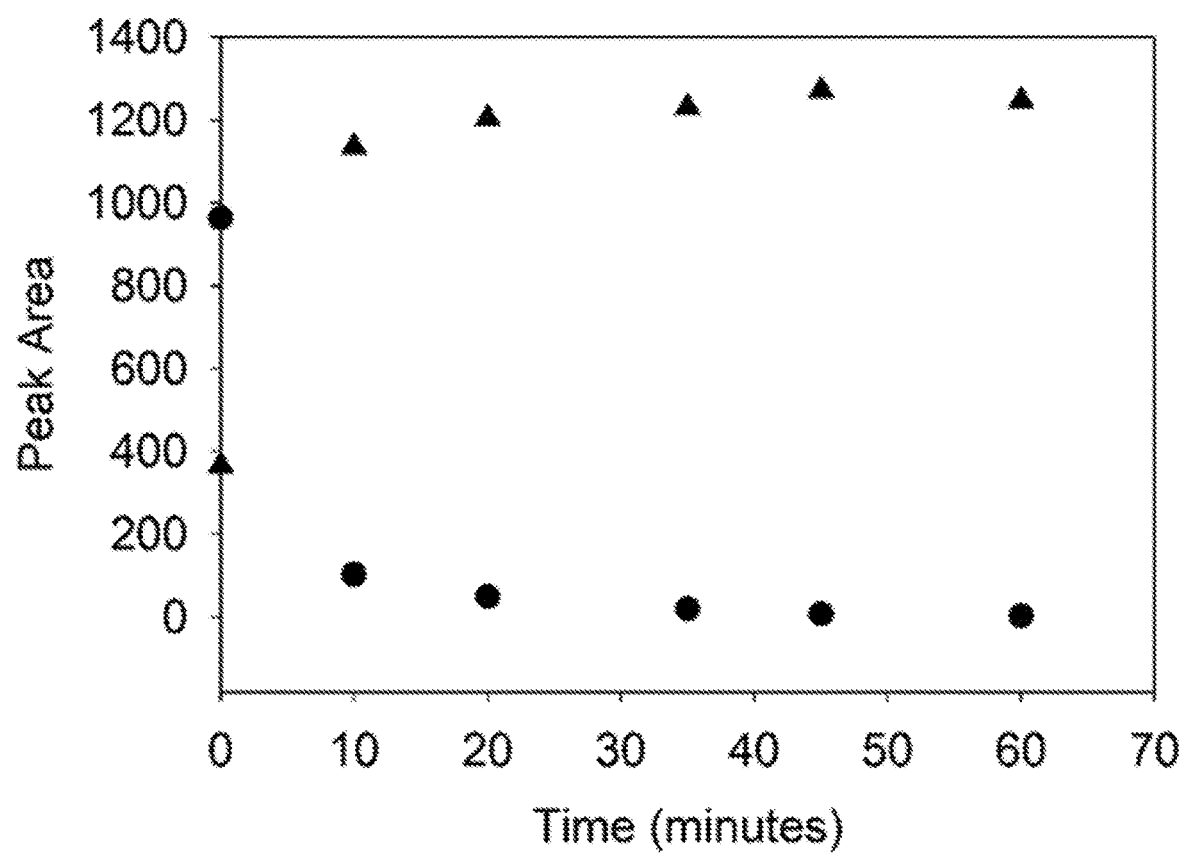
FIG. 16 depicts conversion of 22c to dantrolene in rat plasma. Rat plasma was incubated with 100 μg/mL 22c at 37° C. The area under the prodrug and dantrolene peaks in the 385 nm chromatograms are plotted against reaction time. Circles are the prodrug. Triangles are dantrolene.

To measure the conversion of 22c to dantrolene in rat plasma, a 1 mg/mL solution of 22c was prepared in water. A 100 µL aliquot of 22c was combined with 900 µL plasma taken from Sprague Dawley rats. The plasma reaction was then placed in a 37° C. water bath. The initial concentration of 22c in the plasma was 100 µg/mL. An initial sample was prepared by immediately removing 100 µL from the plasma reaction and mixed it with 100 µL of acetonitrile to quench the reaction, which caused precipitation. The insoluble material was pelleted by centrifugation at 15000 rpm for 5 minutes at 25° C. A sample for LC-MS analysis was prepared by combining 75 µL of the supernatant with 75 µL of water. The LC-MS analysis was performed by injecting 10 µL, and the samples were eluted using the equipment and gradient described in the General UPLC Materials and Methods Section. Additional samples were prepared after 10, 20, 35, 45, 60, 75, and 150 minutes. The loss of 22c and increase in dantrolene were quantified by manual integration of peaks in the 385 nm chromatograms (FIG. 16). The half-life of 22c under these conditions was obtained by fitting an exponential function to the data. Within the first 10 minutes of incubation with plasma 22c had been fully converted to dantrolene. The half-life was estimated to be 3.2 min. A negative control where phosphate-buffered saline was used in place of rat plasma was also performed, and 85% reconversion was observed after 150 minutes.

Figure 17:
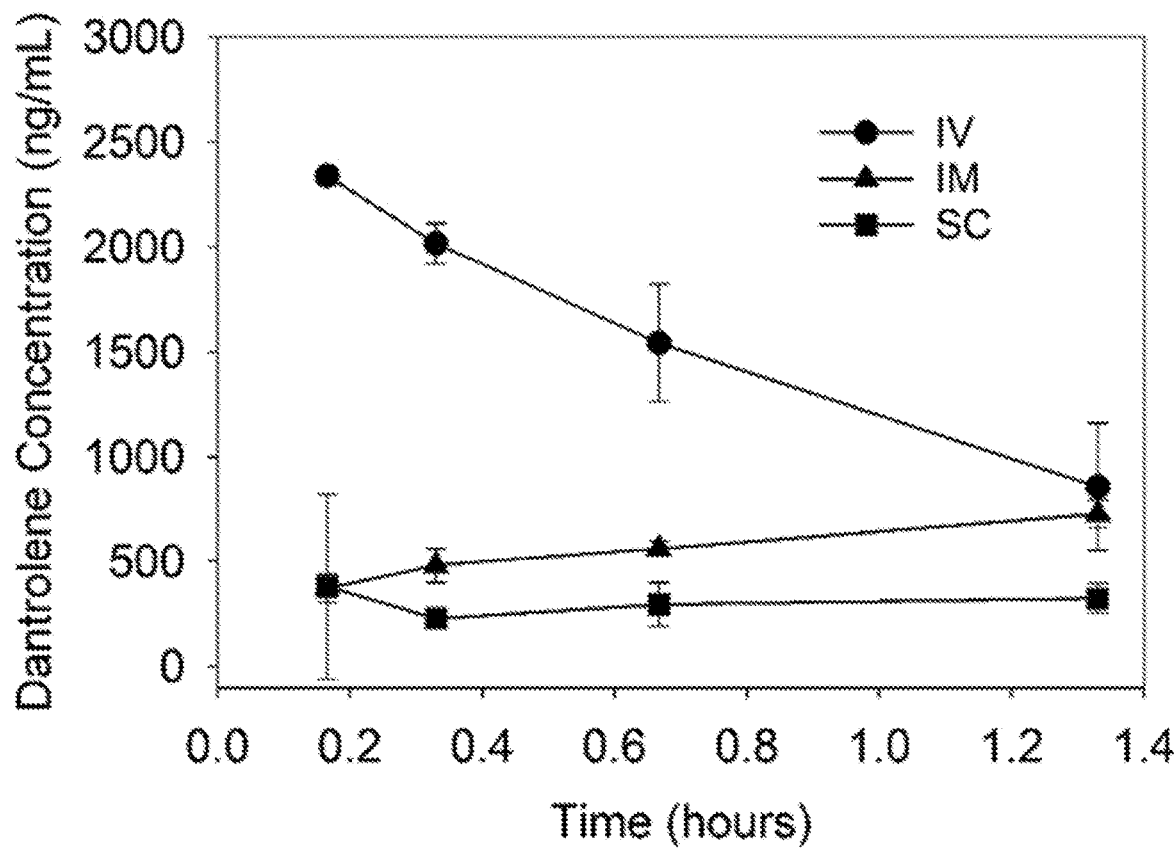
FIG. 17 depicts average concentration of dantrolene in whole blood from animals dosed with 4 mg/kg prodrug 22c (n=3±SEM). Quantification by absorbance at 385 nm.

The pharmacokinetics of 22c in live rats was assayed by dosing vein-cannulated Sprague-Dawley rats, and analyzing the blood for dantrolene using LC-MS (FIG. 17). Intravenous doses were administered through the jugular-vein cannula. Subcutaneous does were administered by injection between the skin and underlying layers of tissue in the left hind limb of each animal. Intramuscular doses were administered by injecting half of the dose into the large muscle mass of the left hind limb and the other half of the dose into the right hind limb. There were three rats in each test group. 22c was dissolved to 3 mg/mL in sterile-filtered aqueous 5% mannitol (w/v) with 10% DMSO to afford a dose level of 4 mg/kg and a dose volume of 1.33 mL/kg. Blood was collected before administration and 0.167, 0.33, 0.66, and 1.33 hours after administration. At each time point, 100 µL of blood was collected into a vial charged with 300 µL of acetonitrile. The blood samples were centrifuged to pellet any insoluble material. The supernatants were flash frozen and stored on dry ice. The samples were analyzed using the methods in the General UPLC Materials and Methods and Pharmacokinetics Analysis sections.

What is claimed:
1. A compound of formula I

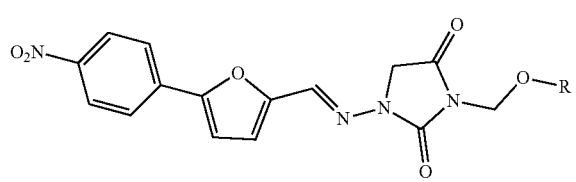

wherein R is
—P(O)(OH)$_2$ or —P(O)(OR$_1$)(OR$_2$);
R$_1$ is H, —C$_{1-26}$alkyl, aryl, C$_{1-6}$alkC(O)O—C$_{1-26}$alkyl, —C$_1$alkOC(O)C$_{1-26}$alkyl, or C$_1$alkOC(O)OC$_{1-26}$alkyl; and
R$_2$ is —C$_{1-26}$alkyl, aryl, C$_{1-6}$alkC(O)O—C$_{1-26}$alkyl, —C$_1$alkOC(O)C$_{1-26}$alkyl, or C$_1$alkOC(O)OC$_{1-26}$alkyl;
or a pharmaceutically acceptable salt thereof.

2. The compound of claim 1, wherein R is —P(O)(OH)$_2$.

3. The compound of claim 1, wherein R is P(O)(OR$_1$)(OR$_2$).

4. The compound of claim 3, wherein R$_1$ is H.

5. The compound of claim 3, wherein R$_1$ is —C$_{1-26}$alkyl.

6. The compound of claim 3, wherein R$_1$ is aryl.

7. The compound of claim 3, wherein R$_1$ is C$_{1-6}$alkC(O)O—C$_{1-26}$alkyl.

8. The compound of claim 3, wherein R$_1$ is —C$_1$alkOC(O)C$_{1-26}$alkyl.

9. The compound of claim 3, wherein R$_1$ is C$_1$alkOC(O)OC$_{1-26}$alkyl.

10. The compound of claim 4, wherein R$_2$ is —C$_{1-26}$alkyl, aryl.

11. The compound of claim 4, wherein R$_2$ is C$_{1-6}$alkC(O)O—C$_{1-26}$alkyl.

12. The compound of claim 4, wherein R$_2$ is —C$_1$alkOC(O)C$_{1-26}$alkyl.

13. The compound of claim 4, wherein R$_2$ is C$_1$alkOC(O)OC$_{1-26}$alkyl.

14. The compound of claim 1, in the form of a pharmaceutically acceptable salt.

15. A pharmaceutical composition comprising a compound of claim 1, or a pharmaceutical salt thereof, and a pharmaceutically acceptable excipient.

16. A method of treating a disorder responsive to dantrolene in a subject comprising administering to the subject a therapeutically effective amount of a compound of claim 1, or a pharmaceutically acceptable salt thereof;

wherein the disorder is selected from malignant hyperthermia, chronic spasticity, exertional heat stroke, cardiac arrhythmias, tachycardia, atrial fibrillation, cardiac arrest, myocardial infarction, heart failure, myocardial injury, cardiomyopathy, central core disease, amyotrophic lateral sclerosis, rhabdomyolysis, Duchenne muscular dystrophy, ataxia, detrusor overactivity, overactive bladder, seizure, epilepsy, neuroleptic malignant syndrome, human stress disorder, Alzheimer's disease, Huntington's disease, multiple sclerosis, Parkinson's disease, ischemia-reperfusion injury, neuronal reperfusion injury, hypoxia, cerebral aneurysm, subarachnoid hemorrhage, stroke, hyperthermia associated with drug abuse, hyperthermia associated with drug overdose, nerve agent exposure, nerve gas exposure, or acetylcholine accumulation.

17. The method of claim 16, wherein the administration is intravenous administration.

18. The method of claim 16, wherein the administration is intramuscular administration.

19. The method of claim 16, wherein the administration is oral administration.

20. The method of claim 16, wherein the administration is subcutaneous.

21. The method of claim 16, wherein the administration is intranasal.

22. The method of claim 16, wherein the administration is intraosseous.

23. A compound of formula II-A

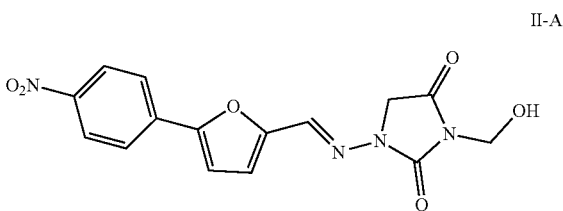 [SMILES: O=C1CN(/N=C/c2ccc(-c3ccc([N+](=O)[O-])cc3)o2)C(=O)N1CO]

or a pharmaceutically acceptable salt thereof.

24. The compound of claim 23, wherein the compound of formula II-A is

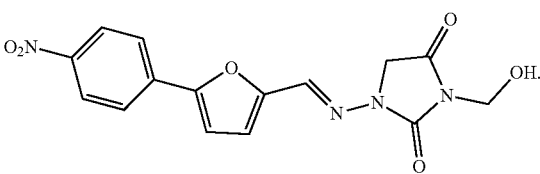 [SMILES: O=C1CN(/N=C/c2ccc(-c3ccc([N+](=O)[O-])cc3)o2)C(=O)N1CO]

* * * * *